(12) United States Patent
Alder et al.

(10) Patent No.: US 12,138,195 B2
(45) Date of Patent: Nov. 12, 2024

(54) FLUID COLLECTION ASSEMBLIES INCLUDING ONE OR MORE LEAK PREVENTION FEATURES

(71) Applicant: PureWick Corporation, El Cajon, CA (US)

(72) Inventors: Larry Dean Alder, Newborn, GA (US); Nathaniel Barnes, Covington, GA (US); Caitlin Bowles, Atlanta, GA (US); Patrick Hudson Chancy, Dunwoody, GA (US); Jingkuang Chen, Rochester, NY (US); Juan Alejandro Saavedra Cisneros, Loganville, GA (US); Brandt Davis, Milford, OH (US); Kyle Daw, Smyrna, GA (US); Rodrigo Fernandez, Loganville, GA (US); Joseph Filbrun, Cincinnati, OH (US); Jeff Edward Franklin, Hamilton, OH (US); Claire Gloeckner, Lilburn, GA (US); Ginger Hiett, Covington, GA (US); Hannah Hinesley, Monticello, GA (US); Ping Huang, Libertyville, GA (US); James David Hughett, Conyers, GA (US); Melissa Young Joyner, Stone Mountain, GA (US); Kevin Michael Knollman, West Chester, OH (US); Kuilin Lai, Watkinsville, GA (US); Michael Lambert, Cincinnati, OH (US); Henri Madigan, Monroe, GA (US); Hassana Salifu, Roswell, GA (US); Misty Savage, Mansfield, GA (US); Michelle Schnell, Hamilton, OH (US); David Simiele, Roswell, GA (US); Michelle Tourchak, Alpharetta, GA (US); Kyra Wesner, Roswell, GA (US); Mackenzie Wier, Chardon, OH (US); Wanfei Yang, Decatur, GA (US); Kelsey Leeke Melbourne, Atlanta, GA (US); Jenny McKinnon, Covington, GA (US)

(73) Assignee: PureWick Corporation, Covington, GA (US)

( * ) Notice: Subject to any disclaimer, the term of this patent is extended or adjusted under 35 U.S.C. 154(b) by 0 days.

(21) Appl. No.: 17/662,700

(22) Filed: May 10, 2022

(65) Prior Publication Data
US 2022/0265462 A1 Aug. 25, 2022

Related U.S. Application Data

(63) Continuation of application No. PCT/US2021/026607, filed on Apr. 9, 2021.
(Continued)

(51) Int. Cl.
*A61F 5/453* (2006.01)
*A61F 5/44* (2006.01)
*A61F 5/455* (2006.01)

(52) U.S. Cl.
CPC ............ *A61F 5/453* (2013.01); *A61F 5/4404* (2013.01); *A61F 5/455* (2013.01)

(58) Field of Classification Search
CPC ...... A61B 10/007; A61F 5/4404; A61F 5/453; A61F 5/455; A61M 1/0023
See application file for complete search history.

(56) References Cited

U.S. PATENT DOCUMENTS 737,443 A 8/1903 Mooers
1,032,841 A 7/1912 Koenig
(Continued)

FOREIGN PATENT DOCUMENTS

AU 2018216821 A1 8/2019
AU 2021299304 A1 2/2023
(Continued)

OTHER PUBLICATIONS

US 9,908,683 B2, 03/2018, Sandhausen et al. (withdrawn)
(Continued)

*Primary Examiner* — Guy K Townsend
(74) *Attorney, Agent, or Firm* — Dorsey & Whitney LLP

(57) ABSTRACT

An example fluid collection assembly includes a fluid impermeable barrier defining at least one opening, a chamber in
(Continued)

fluid communication with the at least one opening, and at least one fluid outlet. The fluid collection assembly also includes at least one porous material (e.g., at least one wicking material) disposed in the chamber. The fluid collection assembly also includes at least one conduit attached to the fluid outlet. Further, the fluid collection assembly includes one or more leak prevention features.

20 Claims, 12 Drawing Sheets

Related U.S. Application Data

(60) Provisional application No. 63/008,112, filed on Apr. 10, 2020.

(56) References Cited

U.S. PATENT DOCUMENTS

| | | |
|---|---|---|
| 1,178,644 A | 4/1916 | Johnson |
| 1,742,080 A | 12/1929 | Jones |
| 1,979,899 A | 11/1934 | Obrien et al. |
| 2,241,010 A | 5/1941 | Chipley |
| 2,262,772 A | 11/1941 | Peder |
| 2,326,881 A | 8/1943 | Packer |
| 2,379,346 A | 6/1945 | Farrell |
| 2,485,555 A | 10/1949 | Bester |
| 2,613,670 A | 10/1952 | Edward |
| 2,616,426 A | 11/1952 | Adele |
| 2,644,234 A | 7/1953 | Earl |
| 2,648,335 A | 8/1953 | Chambers |
| 2,859,786 A | 11/1958 | Tupper |
| 2,944,551 A | 7/1960 | Carl |
| 2,968,046 A * | 1/1961 | Duke ............... A61G 9/006 604/149 |
| 2,971,512 A | 2/1961 | Reinhardt |
| 3,032,038 A | 5/1962 | Swinn |
| 3,077,883 A | 2/1963 | Hill |
| 3,087,938 A | 4/1963 | Hans et al. |
| 3,169,528 A | 2/1965 | Knox et al. |
| 3,171,506 A | 3/1965 | Therkel |
| 3,194,238 A | 7/1965 | Breece |
| 3,198,994 A | 8/1965 | Hildebrandt et al. |
| 3,221,742 A | 12/1965 | Egon |
| 3,312,221 A | 4/1967 | Overment |
| 3,312,981 A | 4/1967 | McGuire et al. |
| 3,349,768 A | 10/1967 | Keane |
| 3,362,590 A | 1/1968 | Gene |
| 3,366,116 A | 1/1968 | Huck |
| 3,398,848 A | 8/1968 | Donovan |
| 3,400,717 A | 9/1968 | Bruce et al. |
| 3,406,688 A | 10/1968 | Bruce |
| 3,424,163 A * | 1/1969 | Gravdahl .......... A61F 13/51121 604/377 |
| 3,425,471 A | 2/1969 | Yates |
| 3,511,241 A | 5/1970 | Lee |
| 3,512,185 A * | 5/1970 | Ellis ................. A61F 5/455 4/144.3 |
| 3,520,300 A | 7/1970 | Flower |
| 3,528,423 A | 9/1970 | Lee |
| 3,613,123 A * | 10/1971 | Langstrom ......... A61F 5/4401 4/144.1 |
| 3,648,700 A | 3/1972 | Warner |
| 3,651,810 A | 3/1972 | Ormerod |
| 3,661,155 A | 5/1972 | Lindan |
| 3,683,918 A | 8/1972 | Pizzella |
| 3,699,815 A | 10/1972 | Holbrook |
| 3,726,277 A | 4/1973 | Hirschman |
| 3,742,952 A | 7/1973 | Magers et al. |
| 3,757,355 A | 9/1973 | Allen et al. |
| 3,788,324 A | 1/1974 | Lim |
| 3,843,016 A | 10/1974 | Bornhorst et al. |
| 3,863,638 A | 2/1975 | Rogers et al. |
| 3,863,798 A | 2/1975 | Kurihara et al. |
| 3,864,759 A | 2/1975 | Horiuchi |
| 3,881,486 A | 5/1975 | Fenton |
| 3,881,489 A | 5/1975 | Hartwell |
| 3,915,189 A | 10/1975 | Holbrook et al. |
| 3,998,228 A | 12/1976 | Poidomani |
| 3,999,550 A | 12/1976 | Martin |
| 4,015,604 A | 4/1977 | Csillag |
| 4,020,843 A | 5/1977 | Kanall |
| 4,022,213 A | 5/1977 | Stein |
| 4,027,776 A | 6/1977 | Douglas |
| 4,064,962 A | 12/1977 | Hunt |
| 4,116,197 A | 9/1978 | Bermingham |
| 4,180,178 A | 12/1979 | Turner |
| 4,187,953 A | 2/1980 | Turner |
| 4,194,508 A | 3/1980 | Anderson |
| 4,200,102 A * | 4/1980 | Duhamel ............. A61F 5/451 604/353 |
| 4,202,058 A | 5/1980 | Anderson |
| 4,203,503 A | 5/1980 | Bertotti et al. |
| 4,209,076 A | 6/1980 | Bertotti et al. |
| 4,233,025 A | 11/1980 | Larson et al. |
| 4,233,978 A | 11/1980 | Hickey |
| 4,246,901 A | 1/1981 | Frosch et al. |
| 4,253,542 A | 3/1981 | Ruspa et al. |
| 4,257,418 A * | 3/1981 | Hessner ............. A61F 5/4401 604/397 |
| 4,270,539 A * | 6/1981 | Frosch ............... A61F 5/455 604/347 |
| 4,281,655 A | 8/1981 | Terauchi |
| 4,292,916 A | 10/1981 | Bradley et al. |
| 4,330,239 A | 5/1982 | Gannaway |
| 4,352,356 A | 10/1982 | Tong |
| 4,360,933 A | 11/1982 | Kimura et al. |
| 4,365,363 A | 12/1982 | Windauer |
| 4,375,841 A | 3/1983 | Vielbig |
| 4,387,726 A | 6/1983 | Denard |
| 4,425,130 A | 1/1984 | Desmarais |
| 4,446,986 A | 5/1984 | Bowen et al. |
| 4,453,938 A | 6/1984 | Brendling |
| 4,457,314 A | 7/1984 | Knowles |
| 4,476,879 A | 10/1984 | Jackson |
| 4,526,688 A | 7/1985 | Schmidt et al. |
| 4,528,703 A | 7/1985 | Kraus |
| D280,438 S | 9/1985 | Wendt |
| 4,551,141 A | 11/1985 | McNeil |
| 4,553,968 A | 11/1985 | Komis |
| 4,581,026 A | 4/1986 | Schneider |
| 4,589,516 A | 5/1986 | Inoue et al. |
| 4,601,716 A | 7/1986 | Smith |
| 4,610,675 A | 9/1986 | Triunfol |
| 4,620,333 A | 11/1986 | Ritter |
| 4,626,250 A | 12/1986 | Schneider |
| 4,627,846 A | 12/1986 | Ternstroem |
| 4,631,061 A * | 12/1986 | Martin ............... A61F 5/451 604/323 |
| 4,650,477 A | 3/1987 | Johnson |
| 4,655,754 A | 4/1987 | Richmond et al. |
| 4,656,675 A | 4/1987 | Fajnsztajn |
| 4,681,570 A | 7/1987 | Dalton |
| 4,681,577 A | 7/1987 | Stern et al. |
| 4,692,160 A | 9/1987 | Nussbaumer |
| 4,707,864 A | 11/1987 | Ikematsu et al. |
| 4,713,065 A | 12/1987 | Koot |
| 4,713,066 A | 12/1987 | Komis |
| 4,723,953 A | 2/1988 | Pratt et al. |
| 4,735,841 A | 4/1988 | Sourdet |
| 4,743,236 A | 5/1988 | Manschot |
| 4,747,166 A * | 5/1988 | Kuntz ................ A61F 5/455 4/144.1 |
| 4,752,944 A | 6/1988 | Conrads et al. |
| 4,769,215 A | 9/1988 | Ehrenkranz |
| 4,771,484 A | 9/1988 | Mozell |
| 4,772,280 A | 9/1988 | Rooyakkers |
| 4,790,830 A | 12/1988 | Hamacher |
| 4,790,835 A | 12/1988 | Elias |
| 4,791,686 A | 12/1988 | Taniguchi et al. |
| 4,795,449 A * | 1/1989 | Schneider ........... A61F 5/4405 604/326 |
| 4,798,603 A | 1/1989 | Meyer et al. |

(56) References Cited

U.S. PATENT DOCUMENTS

| | | | |
|---|---|---|---|
| 4,799,928 A | 1/1989 | Crowley | |
| 4,804,377 A | 2/1989 | Hanifl et al. | |
| 4,812,053 A | 3/1989 | Bhattacharjee | |
| 4,813,943 A | 3/1989 | Smith | |
| 4,820,297 A | 4/1989 | Kaufman et al. | |
| 4,846,818 A | 7/1989 | Keldahl et al. | |
| 4,846,909 A | 7/1989 | Klug et al. | |
| 4,865,595 A | 9/1989 | Heyden | |
| 4,880,417 A | 11/1989 | Yabrov et al. | |
| 4,882,794 A | 11/1989 | Stewart | |
| 4,883,465 A | 11/1989 | Brennan | |
| 4,886,498 A | 12/1989 | Newton | |
| 4,886,508 A * | 12/1989 | Washington | A61F 5/455 604/347 |
| 4,886,509 A | 12/1989 | Mattsson | |
| 4,889,532 A | 12/1989 | Metz et al. | |
| 4,889,533 A | 12/1989 | Beecher | |
| 4,890,691 A | 1/1990 | Ching-ho | |
| 4,903,254 A | 2/1990 | Haas | |
| 4,904,248 A | 2/1990 | Vaillancourt | |
| 4,905,692 A | 3/1990 | More | |
| 4,936,838 A | 6/1990 | Cross et al. | |
| 4,955,922 A | 9/1990 | Terauchi | |
| 4,957,487 A | 9/1990 | Gerow | |
| 4,965,460 A | 10/1990 | Tanaka et al. | |
| 4,987,849 A | 1/1991 | Sherman | |
| 5,002,541 A | 3/1991 | Conkling et al. | |
| 5,004,463 A | 4/1991 | Nigay | |
| 5,031,248 A | 7/1991 | Kemper | |
| 5,045,077 A | 9/1991 | Blake | |
| 5,045,283 A | 9/1991 | Patel | |
| 5,049,144 A * | 9/1991 | Payton | A61F 5/455 600/574 |
| 5,053,339 A | 10/1991 | Patel | |
| 5,057,092 A | 10/1991 | Webster | |
| 5,058,088 A | 10/1991 | Haas et al. | |
| 5,071,347 A | 12/1991 | McGuire | |
| 5,078,707 A | 1/1992 | Peter | |
| 5,084,037 A | 1/1992 | Barnett | |
| 5,100,396 A | 3/1992 | Zamierowski | |
| 5,112,324 A | 5/1992 | Wallace | |
| 5,147,301 A | 9/1992 | Ruvio | |
| 5,176,667 A | 1/1993 | Debring | |
| 5,195,997 A | 3/1993 | Carns | |
| 5,196,654 A | 3/1993 | Diflora et al. | |
| 5,203,699 A | 4/1993 | McGuire | |
| 5,244,458 A | 9/1993 | Takasu | |
| 5,246,454 A | 9/1993 | Peterson | |
| 5,267,988 A | 12/1993 | Farkas | |
| 5,275,307 A | 1/1994 | Freese | |
| 5,282,795 A | 2/1994 | Finney | |
| 5,294,983 A | 3/1994 | Ersoz et al. | |
| 5,295,983 A * | 3/1994 | Kubo | A61F 5/455 4/144.3 |
| 5,300,052 A | 4/1994 | Kubo | |
| 5,304,749 A | 4/1994 | Crandell | |
| 5,312,383 A | 5/1994 | Kubalak | |
| 5,318,550 A | 6/1994 | Cermak et al. | |
| 5,330,459 A | 7/1994 | Lavon et al. | |
| 5,340,840 A | 8/1994 | Park et al. | |
| 5,382,244 A | 1/1995 | Telang | |
| 5,409,014 A | 4/1995 | Napoli et al. | |
| 5,411,495 A | 5/1995 | Willingham | |
| 5,423,784 A | 6/1995 | Metz | |
| 5,456,246 A | 10/1995 | Schmieding et al. | |
| 5,466,229 A * | 11/1995 | Elson | A61M 1/78 604/323 |
| 5,478,334 A | 12/1995 | Bernstein | |
| 5,499,977 A | 3/1996 | Marx | |
| 5,543,042 A | 8/1996 | Filan et al. | |
| D373,928 S | 9/1996 | Green | |
| 5,582,604 A | 12/1996 | Ahr et al. | |
| 5,592,950 A | 1/1997 | Kopelowicz | |
| 5,605,161 A | 2/1997 | Cross | |
| 5,618,277 A | 4/1997 | Goulter | |
| 5,628,735 A | 5/1997 | Skow | |
| 5,636,643 A | 6/1997 | Argenta et al. | |
| 5,637,104 A | 6/1997 | Ball et al. | |
| 5,674,212 A * | 10/1997 | Osborn, III | A61F 13/15 604/385.16 |
| 5,678,564 A * | 10/1997 | Lawrence | A61F 5/455 600/573 |
| 5,678,654 A | 10/1997 | Uzawa | |
| 5,687,429 A | 11/1997 | Rahlff | |
| 5,695,485 A | 12/1997 | Duperret et al. | |
| 5,700,254 A | 12/1997 | Mcdowall et al. | |
| 5,701,612 A | 12/1997 | Daneshvar | |
| 5,705,777 A | 1/1998 | Flanigan et al. | |
| 5,752,944 A | 5/1998 | Dann et al. | |
| 5,772,644 A | 6/1998 | Bark et al. | |
| 5,792,132 A | 8/1998 | Garcia | |
| 5,827,243 A | 10/1998 | Palestrant | |
| 5,827,247 A | 10/1998 | Kay | |
| 5,827,250 A | 10/1998 | Fujioka et al. | |
| 5,827,257 A | 10/1998 | Fujioka et al. | |
| D401,699 S | 11/1998 | Herchenbach et al. | |
| 5,859,393 A | 1/1999 | Cummins et al. | |
| 5,865,378 A | 2/1999 | Hollinshead et al. | |
| 5,876,393 A | 3/1999 | Ahr et al. | |
| 5,887,291 A | 3/1999 | Bellizzi | |
| 5,891,125 A | 4/1999 | Plumley | |
| 5,894,608 A * | 4/1999 | Birbara | A61F 5/4556 604/319 |
| D409,303 S | 5/1999 | Oepping | |
| 5,911,222 A * | 6/1999 | Lawrence | A61F 5/455 600/573 |
| 5,957,904 A | 9/1999 | Holland | |
| 5,968,026 A | 10/1999 | Osborn et al. | |
| 5,972,505 A | 10/1999 | Phillips et al. | |
| 6,039,060 A | 3/2000 | Rower | |
| 6,050,983 A | 4/2000 | Moore et al. | |
| 6,059,762 A | 5/2000 | Boyer et al. | |
| 6,063,064 A | 5/2000 | Tuckey et al. | |
| 6,098,625 A | 8/2000 | Winkler | |
| 6,105,174 A | 8/2000 | Karlsten et al. | |
| 6,113,582 A | 9/2000 | Dwork | |
| 6,117,163 A * | 9/2000 | Bierman | A61M 25/02 606/232 |
| 6,123,398 A * | 9/2000 | Arai | B60T 8/17552 303/151 |
| 6,129,718 A | 10/2000 | Wada et al. | |
| 6,131,964 A | 10/2000 | Sareshwala | |
| 6,152,902 A | 11/2000 | Christian et al. | |
| 6,164,569 A | 12/2000 | Hollinshead et al. | |
| 6,177,606 B1 | 1/2001 | Etheredge et al. | |
| 6,209,142 B1 | 4/2001 | Mattsson et al. | |
| 6,220,050 B1 | 4/2001 | Cooksey | |
| 6,244,311 B1 | 6/2001 | Hand et al. | |
| 6,248,096 B1 | 6/2001 | Dwork et al. | |
| 6,263,887 B1 | 7/2001 | Dunn | |
| 6,283,246 B1 | 9/2001 | Nishikawa | |
| 6,311,339 B1 * | 11/2001 | Kraus | A61G 9/006 4/144.1 |
| 6,336,919 B1 | 1/2002 | Davis et al. | |
| 6,338,729 B1 | 1/2002 | Wada et al. | |
| 6,352,525 B1 | 3/2002 | Wakabayashi | |
| 6,394,988 B1 | 5/2002 | Hashimoto | |
| 6,398,742 B1 * | 6/2002 | Kim | A61F 5/4556 4/144.3 |
| 6,406,463 B1 | 6/2002 | Brown | |
| 6,409,712 B1 | 6/2002 | Dutari et al. | |
| 6,416,500 B1 | 7/2002 | Wada et al. | |
| 6,423,045 B1 | 7/2002 | Wise et al. | |
| 6,428,521 B1 | 8/2002 | Droll | |
| 6,428,522 B1 | 8/2002 | Dipalma et al. | |
| 6,446,454 B1 | 9/2002 | Lee et al. | |
| 6,475,198 B1 | 11/2002 | Lipman et al. | |
| 6,479,726 B1 | 11/2002 | Cole et al. | |
| 6,491,673 B1 | 12/2002 | Palumbo et al. | |
| 6,508,794 B1 | 1/2003 | Palumbo et al. | |
| 6,524,292 B1 | 2/2003 | Dipalma et al. | |
| 6,540,729 B1 | 4/2003 | Wada et al. | |
| 6,547,771 B2 | 4/2003 | Robertson et al. | |

(56) References Cited

U.S. PATENT DOCUMENTS

| | | | |
|---|---|---|---|
| 6,569,133 B2 | 5/2003 | Cheng et al. | |
| D476,518 S | 7/2003 | Doppelt | |
| 6,592,560 B2 | 7/2003 | Snyder et al. | |
| 6,610,038 B1 | 8/2003 | Dipalma et al. | |
| 6,618,868 B2 | 9/2003 | Minnick | |
| 6,620,142 B1 | 9/2003 | Flueckiger | |
| 6,629,651 B1 | 10/2003 | Male et al. | |
| 6,635,038 B2 | 10/2003 | Scovel | |
| 6,652,495 B1 | 11/2003 | Walker | |
| 6,666,850 B1 | 12/2003 | Ahr et al. | |
| 6,685,684 B1 | 2/2004 | Falconer | |
| 6,695,828 B1 | 2/2004 | Dipalma et al. | |
| 6,700,034 B1 | 3/2004 | Lindsay et al. | |
| 6,702,793 B1 | 3/2004 | Sweetser et al. | |
| 6,706,027 B2* | 3/2004 | Harvie | A61F 5/453 604/326 |
| 6,732,384 B2* | 5/2004 | Scott | A47K 11/12 4/144.1 |
| 6,736,977 B1 | 5/2004 | Hall et al. | |
| 6,740,066 B2* | 5/2004 | Wolff | A61F 5/451 604/323 |
| 6,764,477 B1 | 7/2004 | Chen et al. | |
| 6,783,519 B2 | 8/2004 | Samuelsson | |
| 6,796,974 B2 | 9/2004 | Palumbo et al. | |
| 6,814,547 B2 | 11/2004 | Childers et al. | |
| 6,849,065 B2 | 2/2005 | Schmidt et al. | |
| 6,857,137 B2 | 2/2005 | Otto | |
| 6,885,690 B2 | 4/2005 | Aggerstam et al. | |
| 6,888,044 B2 | 5/2005 | Fell et al. | |
| 6,893,425 B2 | 5/2005 | Dunn et al. | |
| 6,912,737 B2 | 7/2005 | Ernest et al. | |
| 6,918,899 B2* | 7/2005 | Harvie | A61F 5/451 604/326 |
| 6,979,324 B2 | 12/2005 | Bybordi et al. | |
| 7,018,366 B2* | 3/2006 | Easter | A61F 5/451 604/327 |
| 7,066,411 B2 | 6/2006 | Male et al. | |
| 7,122,023 B1 | 10/2006 | Hinoki | |
| 7,125,399 B2 | 10/2006 | Miskie | |
| 7,131,964 B2* | 11/2006 | Harvie | A61F 5/455 604/326 |
| 7,135,012 B2* | 11/2006 | Harvie | A61F 5/453 604/326 |
| 7,141,043 B2* | 11/2006 | Harvie | A61F 5/451 604/326 |
| D533,972 S | 12/2006 | La | |
| 7,160,273 B2 | 1/2007 | Greter et al. | |
| 7,171,699 B2 | 2/2007 | Ernest et al. | |
| 7,171,871 B2 | 2/2007 | Kozak | |
| 7,179,951 B2 | 2/2007 | Krishnaswamy-Mirle et al. | |
| 7,181,781 B1* | 2/2007 | Trabold | A61F 5/455 4/144.1 |
| 7,186,245 B1 | 3/2007 | Cheng et al. | |
| 7,192,424 B2 | 3/2007 | Cooper | |
| 7,219,764 B1 | 5/2007 | Forbes | |
| 7,220,250 B2* | 5/2007 | Suzuki | A61F 5/451 604/328 |
| D562,975 S | 2/2008 | Otto | |
| 7,335,189 B2* | 2/2008 | Harvie | A61F 5/451 604/326 |
| 7,358,282 B2 | 4/2008 | Krueger et al. | |
| 7,390,320 B2* | 6/2008 | Machida | A61F 5/455 4/144.1 |
| 7,438,706 B2 | 10/2008 | Koizumi et al. | |
| 7,488,310 B2 | 2/2009 | Yang | |
| 7,491,194 B1 | 2/2009 | Oliwa | |
| D591,106 S | 4/2009 | Dominique et al. | |
| 7,513,381 B2 | 4/2009 | Heng et al. | |
| 7,520,872 B2 | 4/2009 | Biggie et al. | |
| D593,801 S | 6/2009 | Wilson et al. | |
| 7,540,364 B2 | 6/2009 | Sanderson | |
| 7,549,512 B2 | 6/2009 | Newberry | |
| 7,585,293 B2 | 9/2009 | Vermaak | |
| 7,588,560 B1 | 9/2009 | Dunlop | |
| 7,665,359 B2 | 2/2010 | Barber | |
| 7,682,347 B2 | 3/2010 | Parks et al. | |
| 7,687,004 B2 | 3/2010 | Allen | |
| 7,695,459 B2 | 4/2010 | Gilbert et al. | |
| 7,695,460 B2 | 4/2010 | Wada et al. | |
| 7,699,818 B2 | 4/2010 | Gilbert | |
| 7,699,831 B2* | 4/2010 | Bengtson | A61M 27/00 604/313 |
| 7,722,584 B2 | 5/2010 | Tanaka et al. | |
| 7,727,206 B2 | 6/2010 | Gorres | |
| 7,740,620 B2 | 6/2010 | Gilbert et al. | |
| 7,749,205 B2* | 7/2010 | Tazoe | A61F 5/451 604/320 |
| 7,755,497 B2* | 7/2010 | Wada | A61F 5/451 340/604 |
| 7,766,887 B2 | 8/2010 | Burns et al. | |
| D625,407 S | 10/2010 | Koizumi et al. | |
| 7,806,879 B2 | 10/2010 | Brooks et al. | |
| 7,811,272 B2 | 10/2010 | Lindsay et al. | |
| 7,815,067 B2 | 10/2010 | Matsumoto et al. | |
| 7,833,169 B2 | 11/2010 | Hannon | |
| 7,857,806 B2 | 12/2010 | Karpowicz et al. | |
| 7,866,942 B2 | 1/2011 | Harvie | |
| 7,871,385 B2 | 1/2011 | Levinson et al. | |
| 7,875,010 B2 | 1/2011 | Frazier et al. | |
| 7,901,389 B2 | 3/2011 | Mombrinie | |
| 7,927,320 B2 | 4/2011 | Goldwasser et al. | |
| 7,927,321 B2 | 4/2011 | Marland | |
| 7,931,634 B2 | 4/2011 | Swiecicki et al. | |
| 7,939,706 B2* | 5/2011 | Okabe | A61F 5/4404 604/361 |
| 7,946,443 B2 | 5/2011 | Stull et al. | |
| 7,947,025 B2 | 5/2011 | Buglino et al. | |
| 7,963,419 B2 | 6/2011 | Burney et al. | |
| 7,976,519 B2 | 7/2011 | Bubb et al. | |
| 7,993,318 B2 | 8/2011 | Olsson et al. | |
| 8,015,627 B2 | 9/2011 | Baker et al. | |
| 8,016,071 B1 | 9/2011 | Martinus et al. | |
| 8,028,460 B2 | 10/2011 | Williams | |
| 8,047,398 B2 | 11/2011 | Dimartino et al. | |
| 8,083,094 B2 | 12/2011 | Caulfield et al. | |
| 8,128,608 B2* | 3/2012 | Thevenin | A61F 13/84 604/347 |
| 8,181,651 B2 | 5/2012 | Pinel | |
| 8,181,819 B2 | 5/2012 | Burney et al. | |
| 8,211,063 B2* | 7/2012 | Bierman | A61M 25/02 604/179 |
| 8,221,369 B2 | 7/2012 | Parks et al. | |
| 8,241,262 B2 | 8/2012 | Mahnensmith | |
| 8,277,426 B2 | 10/2012 | Wilcox et al. | |
| 8,287,508 B1* | 10/2012 | Sanchez | A61F 5/4404 604/326 |
| 8,303,554 B2 | 11/2012 | Tsai et al. | |
| 8,322,565 B2 | 12/2012 | Caulfield et al. | |
| 8,337,477 B2 | 12/2012 | Parks et al. | |
| D674,241 S | 1/2013 | Bickert et al. | |
| 8,343,122 B2 | 1/2013 | Gorres | |
| 8,343,125 B2 | 1/2013 | Kawazoe et al. | |
| 8,353,074 B2 | 1/2013 | Krebs | |
| 8,353,886 B2 | 1/2013 | Bester et al. | |
| D676,241 S | 2/2013 | Merrill | |
| 8,388,588 B2 | 3/2013 | Wada et al. | |
| D679,807 S | 4/2013 | Burgess et al. | |
| 8,425,482 B2 | 4/2013 | Khoubnazar | |
| 8,434,586 B2 | 5/2013 | Pawelski et al. | |
| 8,449,510 B2 | 5/2013 | Martini et al. | |
| D684,260 S | 6/2013 | Lund et al. | |
| 8,470,230 B2 | 6/2013 | Caulfield et al. | |
| 8,479,941 B2 | 7/2013 | Matsumoto et al. | |
| 8,479,949 B2 | 7/2013 | Henkel | |
| 8,500,719 B1 | 8/2013 | Simpson et al. | |
| 8,512,301 B2 | 8/2013 | Ma | |
| 8,529,530 B2 | 9/2013 | Koch et al. | |
| 8,535,284 B2 | 9/2013 | Joder et al. | |
| 8,546,639 B2* | 10/2013 | Wada | A61F 5/4401 604/361 |
| 8,551,075 B2* | 10/2013 | Bengtson | A61M 1/84 604/543 |

(56) References Cited

U.S. PATENT DOCUMENTS

| | | | |
|---|---|---|---|
| 8,568,376 B2 | 10/2013 | Delattre et al. | |
| D694,404 S | 11/2013 | Burgess et al. | |
| 8,585,683 B2 * | 11/2013 | Bengtson | A61M 1/985 604/543 |
| 8,652,112 B2 | 2/2014 | Johannison et al. | |
| 8,669,412 B2 | 3/2014 | Fernkvist et al. | |
| D702,973 S | 4/2014 | Norland et al. | |
| 8,703,032 B2 | 4/2014 | Menon et al. | |
| D704,330 S | 5/2014 | Cicatelli | |
| D704,510 S | 5/2014 | Mason et al. | |
| D705,423 S | 5/2014 | Walsh Cutler | |
| D705,926 S | 5/2014 | Burgess et al. | |
| 8,714,394 B2 | 5/2014 | Wulf | |
| 8,715,267 B2 | 5/2014 | Bengtson et al. | |
| 8,757,425 B2 | 6/2014 | Copeland | |
| 8,777,032 B2 | 7/2014 | Biesecker et al. | |
| 8,808,260 B2 | 8/2014 | Koch et al. | |
| 8,864,730 B2 | 10/2014 | Conway et al. | |
| 8,881,923 B2 | 11/2014 | Higginson | |
| 8,882,731 B2 | 11/2014 | Suzuki et al. | |
| 8,936,585 B2 | 1/2015 | Carson et al. | |
| D729,581 S | 5/2015 | Boroski | |
| 9,028,460 B2 * | 5/2015 | Medeiros | A61F 5/451 604/347 |
| 9,056,698 B2 | 6/2015 | Noer | |
| 9,078,792 B2 | 7/2015 | Ruiz | |
| 9,145,879 B2 | 9/2015 | Pirovano et al. | |
| 9,173,602 B2 | 11/2015 | Gilbert | |
| 9,173,799 B2 * | 11/2015 | Tanimoto | A61F 5/453 |
| 9,187,220 B2 | 11/2015 | Biesecker et al. | |
| 9,199,772 B2 | 12/2015 | Krippendorf | |
| 9,233,020 B2 * | 1/2016 | Matsumiya | A61F 5/451 |
| 9,248,058 B2 | 2/2016 | Conway et al. | |
| 9,308,118 B1 | 4/2016 | Dupree et al. | |
| 9,309,029 B2 | 4/2016 | Incorvia et al. | |
| 9,333,281 B2 | 5/2016 | Giezendanner et al. | |
| 9,381,108 B2 | 7/2016 | Longoni et al. | |
| 9,382,047 B2 | 7/2016 | Schmidtner et al. | |
| 9,402,424 B2 | 8/2016 | Roy | |
| 9,456,937 B2 | 10/2016 | Ellis | |
| 9,480,595 B2 | 11/2016 | Baham et al. | |
| 9,517,865 B2 | 12/2016 | Albers et al. | |
| D777,941 S | 1/2017 | Piramoon | |
| 9,533,806 B2 | 1/2017 | Ding et al. | |
| 9,550,611 B2 | 1/2017 | Hodge | |
| 9,555,930 B2 | 1/2017 | Campbell et al. | |
| 9,623,159 B2 | 4/2017 | Locke | |
| D789,522 S | 6/2017 | Burgess et al. | |
| 9,687,849 B2 | 6/2017 | Bruno et al. | |
| 9,694,949 B2 | 7/2017 | Hendricks et al. | |
| 9,709,048 B2 | 7/2017 | Kinjo | |
| 9,713,547 B2 | 7/2017 | Lee et al. | |
| 9,732,754 B2 | 8/2017 | Huang et al. | |
| 9,752,564 B2 | 9/2017 | Arceno et al. | |
| 9,788,992 B2 | 10/2017 | Harvie | |
| D804,907 S | 12/2017 | Sandoval | |
| 9,868,564 B2 | 1/2018 | McGirr et al. | |
| D814,239 S | 4/2018 | Arora | |
| D817,484 S | 5/2018 | Lafond | |
| 10,037,640 B2 | 7/2018 | Gordon | |
| 10,058,470 B2 | 8/2018 | Phillips | |
| 10,098,990 B2 | 10/2018 | Koch et al. | |
| D835,264 S | 12/2018 | Mozzicato et al. | |
| D835,779 S | 12/2018 | Mozzicato et al. | |
| D840,533 S | 2/2019 | Mozzicato et al. | |
| D840,534 S | 2/2019 | Mozzicato et al. | |
| 10,225,376 B2 | 3/2019 | Perez Martinez | |
| 10,226,376 B2 * | 3/2019 | Sanchez | A61F 5/455 |
| 10,258,517 B1 | 4/2019 | Maschino et al. | |
| D848,612 S | 5/2019 | Mozzicato et al. | |
| 10,307,305 B1 | 6/2019 | Hodges | |
| 10,335,121 B2 | 7/2019 | Desai | |
| D856,512 S | 8/2019 | Cowart et al. | |
| 10,376,406 B2 * | 8/2019 | Newton | A61F 5/4404 |
| 10,376,407 B2 | 8/2019 | Newton | |
| 10,390,989 B2 * | 8/2019 | Sanchez | A61F 5/453 |
| D858,144 S | 9/2019 | Fu | |
| 10,406,039 B2 | 9/2019 | Villarreal | |
| 10,407,222 B2 | 9/2019 | Allen | |
| 10,478,356 B2 | 11/2019 | Griffin | |
| 10,500,108 B1 | 12/2019 | Maschino et al. | |
| 10,538,366 B2 | 1/2020 | Pentelovitch et al. | |
| 10,569,938 B2 | 2/2020 | Zhao et al. | |
| 10,577,156 B2 | 3/2020 | Dagnelie et al. | |
| RE47,930 E | 4/2020 | Cho | |
| 10,618,721 B2 | 4/2020 | Vazin | |
| D884,390 S | 5/2020 | Wang | |
| 10,669,079 B2 | 6/2020 | Freedman et al. | |
| D892,315 S | 8/2020 | Airy | |
| 10,730,672 B2 | 8/2020 | Bertram et al. | |
| 10,737,848 B2 | 8/2020 | Philip et al. | |
| 10,765,854 B2 | 9/2020 | Law et al. | |
| 10,766,670 B2 | 9/2020 | Kittmann | |
| 10,799,386 B1 | 10/2020 | Harrison | |
| 10,806,642 B2 | 10/2020 | Tagomori et al. | |
| D901,214 S | 11/2020 | Hu | |
| 10,849,799 B2 | 12/2020 | Nishikawa et al. | |
| 10,857,025 B2 | 12/2020 | Davis et al. | |
| 10,865,017 B1 | 12/2020 | Cowart et al. | |
| 10,889,412 B2 | 1/2021 | West et al. | |
| 10,913,581 B2 | 2/2021 | Stahlecker | |
| D912,244 S | 3/2021 | Rehm et al. | |
| 10,952,889 B2 * | 3/2021 | Newton | A61F 5/4404 |
| 10,973,378 B2 | 4/2021 | Ryu et al. | |
| 10,973,678 B2 * | 4/2021 | Newton | A61M 1/71 |
| 10,974,874 B2 | 4/2021 | Ragias et al. | |
| 11,000,401 B2 | 5/2021 | Ecklund et al. | |
| D923,365 S | 6/2021 | Wang | |
| 11,026,829 B2 * | 6/2021 | Harvie | A61M 25/0017 |
| 11,027,900 B2 | 6/2021 | Liu | |
| 11,045,346 B2 | 6/2021 | Argent et al. | |
| D928,946 S * | 8/2021 | Sanchez | D24/122 |
| 11,160,695 B2 | 11/2021 | Febo et al. | |
| 11,160,697 B2 | 11/2021 | Maschino et al. | |
| 11,168,420 B2 | 11/2021 | Kinugasa et al. | |
| 11,179,506 B2 | 11/2021 | Barr et al. | |
| 11,226,376 B2 | 1/2022 | Yamauchi et al. | |
| 11,253,407 B2 | 2/2022 | Miao et al. | |
| 11,326,586 B2 | 5/2022 | Milner et al. | |
| 11,369,508 B2 | 6/2022 | Ecklund et al. | |
| 11,369,524 B2 | 6/2022 | Hubbard et al. | |
| 11,376,152 B2 * | 7/2022 | Sanchez | A61F 5/4404 |
| 11,382,786 B2 * | 7/2022 | Sanchez | A61F 5/455 |
| 11,382,788 B2 | 7/2022 | Hjorth et al. | |
| 11,389,318 B2 | 7/2022 | Radl et al. | |
| 11,395,871 B2 | 7/2022 | Radl et al. | |
| 11,399,990 B2 | 8/2022 | Suyama | |
| 11,426,303 B2 * | 8/2022 | Davis | A61F 5/455 |
| 11,504,265 B2 | 11/2022 | Godinez et al. | |
| 11,529,252 B2 * | 12/2022 | Glithero | A61F 5/453 |
| 11,547,788 B2 | 1/2023 | Radl et al. | |
| 11,806,266 B2 | 11/2023 | Sanchez et al. | |
| 11,839,567 B2 | 12/2023 | Davis et al. | |
| D1,010,109 S | 1/2024 | Ecklund et al. | |
| 11,857,716 B2 | 1/2024 | Lee et al. | |
| 11,865,030 B2 | 1/2024 | Davis et al. | |
| 11,890,221 B2 | 2/2024 | Ulreich et al. | |
| 11,925,575 B2 | 3/2024 | Newton | |
| 11,938,053 B2 | 3/2024 | Austermann et al. | |
| 11,944,740 B2 | 4/2024 | Hughett et al. | |
| 2001/0037097 A1 | 11/2001 | Cheng et al. | |
| 2001/0054426 A1 | 12/2001 | Knudson et al. | |
| 2002/0019614 A1 * | 2/2002 | Woon | A61F 13/53747 604/378 |
| 2002/0026161 A1 | 2/2002 | Grundke | |
| 2002/0087131 A1 * | 7/2002 | Wolff | A61B 5/20 604/327 |
| 2002/0091364 A1 | 7/2002 | Prabhakar | |
| 2002/0189992 A1 | 12/2002 | Schmidt et al. | |
| 2002/0193760 A1 | 12/2002 | Thompson | |
| 2003/0004436 A1 | 1/2003 | Schmidt et al. | |
| 2003/0032931 A1 | 2/2003 | Grundke et al. | |
| 2003/0032944 A1 | 2/2003 | Cawood | |
| 2003/0073964 A1 | 4/2003 | Palumbo et al. | |

(56) References Cited

U.S. PATENT DOCUMENTS

| | | |
|---|---|---|
| 2003/0120178 A1 | 6/2003 | Heki |
| 2003/0157859 A1 | 8/2003 | Ishikawa |
| 2003/0181880 A1 | 9/2003 | Schwartz |
| 2003/0195484 A1* | 10/2003 | Harvie ............... A61F 5/455 604/355 |
| 2003/0204173 A1 | 10/2003 | Burns et al. |
| 2003/0233079 A1 | 12/2003 | Parks et al. |
| 2004/0006321 A1 | 1/2004 | Cheng et al. |
| 2004/0015141 A1 | 1/2004 | Cheng et al. |
| 2004/0056122 A1 | 3/2004 | Male et al. |
| 2004/0084465 A1 | 5/2004 | Luburic |
| 2004/0127872 A1* | 7/2004 | Petryk ............... A61F 13/49 604/382 |
| 2004/0128749 A1 | 7/2004 | Scott |
| 2004/0143229 A1* | 7/2004 | Easter ............... A61F 5/451 604/322 |
| 2004/0147863 A1 | 7/2004 | Diaz et al. |
| 2004/0147894 A1 | 7/2004 | Mizutani et al. |
| 2004/0158221 A1 | 8/2004 | Mizutani et al. |
| 2004/0176731 A1 | 9/2004 | Cheng et al. |
| 2004/0176746 A1 | 9/2004 | Forral |
| 2004/0191919 A1 | 9/2004 | Unger et al. |
| 2004/0207530 A1* | 10/2004 | Nielsen ............... A61F 13/42 340/573.5 |
| 2004/0236292 A1* | 11/2004 | Tazoe ............... A61F 5/451 604/317 |
| 2004/0243075 A1 | 12/2004 | Harvie |
| 2004/0254547 A1* | 12/2004 | Okabe ............... A61F 5/455 604/317 |
| 2005/0010182 A1 | 1/2005 | Parks et al. |
| 2005/0033248 A1* | 2/2005 | Machida ............... A61F 5/455 604/327 |
| 2005/0065471 A1 | 3/2005 | Kuntz |
| 2005/0070861 A1* | 3/2005 | Okabe ............... A61F 5/4404 604/327 |
| 2005/0070862 A1* | 3/2005 | Tazoe ............... A61F 5/455 604/327 |
| 2005/0082300 A1 | 4/2005 | Modrell et al. |
| 2005/0097662 A1 | 5/2005 | Leimkuhler et al. |
| 2005/0101924 A1 | 5/2005 | Elson et al. |
| 2005/0119630 A1 | 6/2005 | Harvie |
| 2005/0137557 A1 | 6/2005 | Swiecicki et al. |
| 2005/0154360 A1 | 7/2005 | Harvie |
| 2005/0177070 A1 | 8/2005 | Levinson et al. |
| 2005/0197639 A1 | 9/2005 | Mombrinie |
| 2005/0273920 A1 | 12/2005 | Marinas |
| 2005/0277904 A1 | 12/2005 | Chase et al. |
| 2005/0279359 A1 | 12/2005 | Leblanc et al. |
| 2006/0004332 A1 | 1/2006 | Marx |
| 2006/0015080 A1 | 1/2006 | Mahnensmith |
| 2006/0015081 A1* | 1/2006 | Suzuki ............... A61F 5/451 604/329 |
| 2006/0016778 A1 | 1/2006 | Park |
| 2006/0069359 A1 | 3/2006 | Dipalma et al. |
| 2006/0079854 A1 | 4/2006 | Kay et al. |
| 2006/0111648 A1* | 5/2006 | Vermaak ............... A61B 10/007 604/355 |
| 2006/0155214 A1* | 7/2006 | Wightman ............... A61F 5/455 600/574 |
| 2006/0171997 A1 | 8/2006 | Gruenbacher et al. |
| 2006/0200102 A1 | 9/2006 | Cooper |
| 2006/0229575 A1 | 10/2006 | Boiarski |
| 2006/0229576 A1 | 10/2006 | Conway et al. |
| 2006/0231648 A1 | 10/2006 | Male et al. |
| 2006/0235266 A1 | 10/2006 | Nan |
| 2006/0235359 A1 | 10/2006 | Marland |
| 2006/0241553 A1 | 10/2006 | Harvie |
| 2006/0269439 A1 | 11/2006 | White |
| 2006/0277670 A1 | 12/2006 | Baker et al. |
| 2007/0006368 A1 | 1/2007 | Key et al. |
| 2007/0010797 A1 | 1/2007 | Nishtala et al. |
| 2007/0016152 A1 | 1/2007 | Karpowicz et al. |
| 2007/0038194 A1* | 2/2007 | Wada ............... A61F 5/451 604/347 |
| 2007/0055209 A1 | 3/2007 | Patel et al. |
| 2007/0073252 A1 | 3/2007 | Forgrave |
| 2007/0117880 A1 | 5/2007 | Elson et al. |
| 2007/0118993 A1 | 5/2007 | Bates |
| 2007/0135786 A1 | 6/2007 | Schmidt et al. |
| 2007/0137718 A1 | 6/2007 | Rushlander et al. |
| 2007/0149935 A1 | 6/2007 | Dirico |
| 2007/0191804 A1 | 8/2007 | Coley |
| 2007/0214553 A1* | 9/2007 | Carromba ............... A47K 11/12 4/144.4 |
| 2007/0225663 A1 | 9/2007 | Watt et al. |
| 2007/0225666 A1 | 9/2007 | Otto |
| 2007/0225668 A1 | 9/2007 | Otto |
| 2007/0266486 A1 | 11/2007 | Ramirez |
| 2007/0282309 A1 | 12/2007 | Bengtson et al. |
| 2008/0004576 A1 | 1/2008 | Tanaka et al. |
| 2008/0015526 A1 | 1/2008 | Reiner et al. |
| 2008/0015527 A1 | 1/2008 | House |
| 2008/0033386 A1* | 2/2008 | Okabe ............... A61F 5/4404 604/378 |
| 2008/0041869 A1 | 2/2008 | Backaert |
| 2008/0091153 A1* | 4/2008 | Harvie ............... A61F 5/451 604/318 |
| 2008/0091158 A1 | 4/2008 | Yang |
| 2008/0114327 A1 | 5/2008 | Barge |
| 2008/0167634 A1 | 7/2008 | Kouta et al. |
| 2008/0183157 A1 | 7/2008 | Walters |
| 2008/0215031 A1 | 9/2008 | Belfort et al. |
| 2008/0234642 A1 | 9/2008 | Patterson et al. |
| 2008/0269703 A1 | 10/2008 | Collins et al. |
| 2008/0281282 A1 | 11/2008 | Finger et al. |
| 2008/0287894 A1* | 11/2008 | Van Den Heuvel .... A61F 5/455 604/327 |
| 2008/0312550 A1 | 12/2008 | Nishtala et al. |
| 2009/0025717 A1 | 1/2009 | Pinel |
| 2009/0048570 A1 | 2/2009 | Jensen |
| 2009/0056003 A1 | 3/2009 | Ivie et al. |
| 2009/0069761 A1 | 3/2009 | Vogel |
| 2009/0069765 A1 | 3/2009 | Wortham |
| 2009/0192482 A1* | 7/2009 | Dodge, II ......... A61F 13/53708 524/436 |
| 2009/0234312 A1 | 9/2009 | OToole et al. |
| 2009/0251510 A1 | 10/2009 | Noro et al. |
| 2009/0264840 A1 | 10/2009 | Virginio |
| 2009/0270822 A1* | 10/2009 | Medeiros ............... A61F 5/451 604/347 |
| 2009/0281510 A1 | 11/2009 | Fisher |
| 2010/0004612 A1* | 1/2010 | Thevenin ............... A61F 13/84 4/443 |
| 2010/0058660 A1 | 3/2010 | Williams |
| 2010/0121289 A1 | 5/2010 | Parks et al. |
| 2010/0158168 A1 | 6/2010 | Murthy et al. |
| 2010/0160882 A1 | 6/2010 | Lowe |
| 2010/0174250 A1 | 7/2010 | Hu et al. |
| 2010/0185168 A1* | 7/2010 | Graauw ............... A61F 5/4556 604/347 |
| 2010/0198172 A1 | 8/2010 | Wada et al. |
| 2010/0211032 A1* | 8/2010 | Tsai ............... A61F 5/453 604/319 |
| 2010/0234820 A1 | 9/2010 | Tsai et al. |
| 2010/0241104 A1 | 9/2010 | Gilbert |
| 2010/0263113 A1 | 10/2010 | Shelton et al. |
| 2010/0310845 A1 | 12/2010 | Bond et al. |
| 2011/0028920 A1 | 2/2011 | Johannison |
| 2011/0028922 A1 | 2/2011 | Kay et al. |
| 2011/0034889 A1 | 2/2011 | Smith |
| 2011/0036837 A1 | 2/2011 | Shang |
| 2011/0040267 A1* | 2/2011 | Wada ............... A61F 5/4401 604/318 |
| 2011/0040271 A1* | 2/2011 | Rogers ............... A61F 5/4556 604/346 |
| 2011/0054426 A1 | 3/2011 | Stewart et al. |
| 2011/0060299 A1 | 3/2011 | Wada et al. |
| 2011/0060300 A1* | 3/2011 | Weig ............... A61F 5/451 604/319 |
| 2011/0077495 A1 | 3/2011 | Gilbert |
| 2011/0077606 A1 | 3/2011 | Wilcox et al. |
| 2011/0087337 A1 | 4/2011 | Forsell |

(56) References Cited

U.S. PATENT DOCUMENTS

| | | |
|---|---|---|
| 2011/0137273 A1 | 6/2011 | Muellejans et al. |
| 2011/0145993 A1 | 6/2011 | Rader et al. |
| 2011/0152802 A1 | 6/2011 | Dicamillo et al. |
| 2011/0164147 A1 | 7/2011 | Takahashi et al. |
| 2011/0172620 A1 | 7/2011 | Khambatta |
| 2011/0172625 A1* | 7/2011 | Wada ................ A61F 13/42 604/385.01 |
| 2011/0202024 A1 | 8/2011 | Cozzens |
| 2011/0238023 A1 | 9/2011 | Slayton |
| 2011/0240648 A1 | 10/2011 | Tucker |
| 2011/0251572 A1 | 10/2011 | Nishtala et al. |
| 2011/0265889 A1 | 11/2011 | Tanaka et al. |
| 2011/0276020 A1 | 11/2011 | Mitsui |
| 2012/0035577 A1 | 2/2012 | Tomes et al. |
| 2012/0041400 A1 | 2/2012 | Christensen |
| 2012/0059328 A1 | 3/2012 | Dikeman et al. |
| 2012/0066825 A1 | 3/2012 | Birbara et al. |
| 2012/0103347 A1* | 5/2012 | Wheaton ............ A61F 5/453 128/885 |
| 2012/0137420 A1 | 6/2012 | Gordon et al. |
| 2012/0165768 A1 | 6/2012 | Sekiyama et al. |
| 2012/0165786 A1 | 6/2012 | Chappa et al. |
| 2012/0210503 A1* | 8/2012 | Anzivino, Sr. ........ A61F 5/4556 4/144.3 |
| 2012/0233761 A1 | 9/2012 | Huang |
| 2012/0245541 A1 | 9/2012 | Suzuki et al. |
| 2012/0245542 A1* | 9/2012 | Suzuki ................ A61F 13/84 374/45 |
| 2012/0245547 A1 | 9/2012 | Wilcox et al. |
| 2012/0253303 A1* | 10/2012 | Suzuki ................ A61F 13/42 374/45 |
| 2012/0271259 A1 | 10/2012 | Ulert |
| 2012/0296305 A1 | 11/2012 | Barraza Khaled et al. |
| 2012/0316522 A1 | 12/2012 | Carter et al. |
| 2012/0330256 A1 | 12/2012 | Wilcox et al. |
| 2013/0006206 A1* | 1/2013 | Wada ................ A61F 13/535 604/385.01 |
| 2013/0045651 A1 | 2/2013 | Esteves et al. |
| 2013/0053804 A1 | 2/2013 | Soerensen et al. |
| 2013/0096523 A1 | 4/2013 | Chang et al. |
| 2013/0138064 A1 | 5/2013 | Stroebech et al. |
| 2013/0150813 A1 | 6/2013 | Gordon et al. |
| 2013/0245496 A1 | 9/2013 | Wells et al. |
| 2013/0245586 A1 | 9/2013 | Jha |
| 2013/0292537 A1 | 11/2013 | Dirico |
| 2013/0330501 A1 | 12/2013 | Aizenberg et al. |
| 2014/0005647 A1 | 1/2014 | Shuffler et al. |
| 2014/0031774 A1* | 1/2014 | Bengtson ............ A61M 1/90 604/319 |
| 2014/0039432 A1 | 2/2014 | Dunbar et al. |
| 2014/0157499 A1 | 6/2014 | Suzuki et al. |
| 2014/0171889 A1 | 6/2014 | Hopman et al. |
| 2014/0182051 A1* | 7/2014 | Tanimoto ............ A61G 9/006 4/144.3 |
| 2014/0196189 A1 | 7/2014 | Lee et al. |
| 2014/0276501 A1 | 9/2014 | Cisko |
| 2014/0303582 A1 | 10/2014 | Wright et al. |
| 2014/0316381 A1 | 10/2014 | Reglin |
| 2014/0325746 A1 | 11/2014 | Block |
| 2014/0348139 A1 | 11/2014 | Gomez Martinez |
| 2014/0352050 A1 | 12/2014 | Yao et al. |
| 2014/0371628 A1 | 12/2014 | Desai |
| 2015/0045757 A1 | 2/2015 | Lee et al. |
| 2015/0047114 A1 | 2/2015 | Ramirez |
| 2015/0048089 A1 | 2/2015 | Robertson |
| 2015/0135423 A1 | 5/2015 | Sharpe et al. |
| 2015/0157300 A1 | 6/2015 | Ealovega et al. |
| 2015/0209194 A1 | 7/2015 | Heyman |
| 2015/0290425 A1 | 10/2015 | Macy et al. |
| 2015/0320583 A1 | 11/2015 | Harvie |
| 2015/0329255 A1 | 11/2015 | Rzepecki |
| 2015/0342799 A1 | 12/2015 | Michiels et al. |
| 2015/0359660 A1* | 12/2015 | Harvie ................ A61F 5/441 604/351 |
| 2015/0366699 A1 | 12/2015 | Nelson |
| 2016/0029998 A1 | 2/2016 | Brister et al. |
| 2016/0030228 A1 | 2/2016 | Jones |
| 2016/0038356 A1 | 2/2016 | Yao et al. |
| 2016/0058322 A1 | 3/2016 | Brister et al. |
| 2016/0060001 A1 | 3/2016 | Wada et al. |
| 2016/0100976 A1 | 4/2016 | Conway et al. |
| 2016/0106604 A1* | 4/2016 | Timm ................ A61F 13/84 604/385.01 |
| 2016/0113809 A1 | 4/2016 | Kim |
| 2016/0183689 A1 | 6/2016 | Miner |
| 2016/0256022 A1 | 9/2016 | Le |
| 2016/0270982 A1 | 9/2016 | Raycheck et al. |
| 2016/0278662 A1 | 9/2016 | Brister et al. |
| 2016/0357400 A1 | 12/2016 | Penha et al. |
| 2016/0366699 A1 | 12/2016 | Zhang et al. |
| 2016/0367226 A1* | 12/2016 | Newton ................ A01K 23/005 |
| 2016/0367411 A1 | 12/2016 | Justiz et al. |
| 2016/0367726 A1 | 12/2016 | Gratzer |
| 2016/0374848 A1* | 12/2016 | Sanchez ................ A61F 5/453 604/319 |
| 2017/0007438 A1* | 1/2017 | Harvie ................ A61F 5/453 |
| 2017/0014560 A1 | 1/2017 | Minskoff et al. |
| 2017/0100276 A1 | 4/2017 | Joh |
| 2017/0128638 A1 | 5/2017 | Giezendanner et al. |
| 2017/0143534 A1 | 5/2017 | Sanchez |
| 2017/0165405 A1 | 6/2017 | Muser et al. |
| 2017/0189225 A1 | 7/2017 | Voorhees et al. |
| 2017/0202692 A1 | 7/2017 | Laniado |
| 2017/0216081 A1 | 8/2017 | Accosta |
| 2017/0246026 A1 | 8/2017 | Laniado |
| 2017/0252014 A1 | 9/2017 | Siller Gonzalez et al. |
| 2017/0252202 A9 | 9/2017 | Sanchez et al. |
| 2017/0266031 A1* | 9/2017 | Sanchez ................ A61F 5/4404 |
| 2017/0266658 A1 | 9/2017 | Bruno et al. |
| 2017/0281399 A1* | 10/2017 | VanMiddendorp ..... A61F 5/455 |
| 2017/0312116 A1 | 11/2017 | Laniado |
| 2017/0325788 A1 | 11/2017 | Ealovega et al. |
| 2017/0333244 A1 | 11/2017 | Laniado |
| 2017/0342748 A1 | 11/2017 | Griffin |
| 2017/0348139 A1* | 12/2017 | Newton ................ A61F 5/4404 |
| 2017/0354532 A1 | 12/2017 | Holt |
| 2017/0354551 A1 | 12/2017 | Gawley et al. |
| 2017/0367873 A1 | 12/2017 | Grannum |
| 2018/0002075 A1 | 1/2018 | Lee |
| 2018/0008451 A1 | 1/2018 | Stroebech |
| 2018/0008804 A1 | 1/2018 | Laniado |
| 2018/0021218 A1 | 1/2018 | Brosch et al. |
| 2018/0028349 A1* | 2/2018 | Newton ................ A61M 1/71 |
| 2018/0037384 A1 | 2/2018 | Archeny et al. |
| 2018/0049910 A1 | 2/2018 | Newton |
| 2018/0064572 A1 | 3/2018 | Wiltshire |
| 2018/0104131 A1 | 4/2018 | Killian |
| 2018/0127187 A1 | 5/2018 | Sewell |
| 2018/0193215 A1 | 7/2018 | Davies et al. |
| 2018/0200101 A1 | 7/2018 | Su |
| 2018/0228642 A1* | 8/2018 | Davis ................ A61F 5/451 |
| 2018/0256384 A1 | 9/2018 | Kasirye |
| 2018/0271694 A1 | 9/2018 | Fernandez et al. |
| 2018/0317892 A1 | 11/2018 | Catlin |
| 2019/0001030 A1 | 1/2019 | Braga et al. |
| 2019/0021899 A1 | 1/2019 | Vlet |
| 2019/0038451 A1* | 2/2019 | Harvie ................ A61F 5/441 |
| 2019/0046102 A1 | 2/2019 | Kushnir et al. |
| 2019/0100362 A1 | 4/2019 | Meyers et al. |
| 2019/0133814 A1 | 5/2019 | Tammen et al. |
| 2019/0142624 A1* | 5/2019 | Sanchez ................ A61F 5/453 604/319 |
| 2019/0224036 A1* | 7/2019 | Sanchez ................ A61F 5/443 |
| 2019/0247222 A1 | 8/2019 | Ecklund et al. |
| 2019/0247223 A1 | 8/2019 | Brun et al. |
| 2019/0282391 A1 | 9/2019 | Johannes et al. |
| 2019/0314189 A1 | 10/2019 | Acosta |
| 2019/0314190 A1* | 10/2019 | Sanchez ................ A61F 5/453 |
| 2019/0321587 A1 | 10/2019 | Mcmenamin et al. |
| 2019/0344934 A1 | 11/2019 | Faerber et al. |
| 2019/0365307 A1 | 12/2019 | Laing et al. |
| 2019/0365561 A1 | 12/2019 | Newton et al. |
| 2020/0008985 A1 | 1/2020 | Nguyen et al. |

(56) References Cited

U.S. PATENT DOCUMENTS

| | | |
|---|---|---|
| 2020/0016012 A1 | 1/2020 | Dutkiewicz |
| 2020/0030595 A1 | 1/2020 | Boukidjian et al. |
| 2020/0046544 A1* | 2/2020 | Godinez ............... A61F 5/451 |
| 2020/0055638 A1 | 2/2020 | Lau et al. |
| 2020/0070392 A1 | 3/2020 | Huber et al. |
| 2020/0085609 A1 | 3/2020 | Schelch et al. |
| 2020/0085610 A1 | 3/2020 | Cohn et al. |
| 2020/0086090 A1 | 3/2020 | Von Weymarn-Schärli et al. |
| 2020/0107518 A1 | 4/2020 | Hiroshima et al. |
| 2020/0129322 A1 | 4/2020 | Leuckel |
| 2020/0171217 A9 | 6/2020 | Braga et al. |
| 2020/0206039 A1 | 7/2020 | Mclain |
| 2020/0214910 A1 | 7/2020 | Varona et al. |
| 2020/0216898 A1 | 7/2020 | Hubbell |
| 2020/0216989 A1 | 7/2020 | Kinugasa et al. |
| 2020/0229964 A1 | 7/2020 | Staali et al. |
| 2020/0231343 A1 | 7/2020 | Freedman et al. |
| 2020/0232841 A1 | 7/2020 | Satish et al. |
| 2020/0246172 A1 | 8/2020 | Ho |
| 2020/0246203 A1 | 8/2020 | Tulk et al. |
| 2020/0255189 A1 | 8/2020 | Liu |
| 2020/0261280 A1 | 8/2020 | Heyman |
| 2020/0276046 A1 | 9/2020 | Staali et al. |
| 2020/0306075 A1 | 10/2020 | Newton et al. |
| 2020/0315837 A1 | 10/2020 | Radl et al. |
| 2020/0315838 A1 | 10/2020 | Eckert |
| 2020/0315872 A1 | 10/2020 | Viens et al. |
| 2020/0315874 A1 | 10/2020 | Viens et al. |
| 2020/0331672 A1 | 10/2020 | Bertram et al. |
| 2020/0345332 A1 | 11/2020 | Duval |
| 2020/0353135 A1 | 11/2020 | Gregory et al. |
| 2020/0367677 A1 | 11/2020 | Silsby et al. |
| 2020/0369444 A1 | 11/2020 | Silsby et al. |
| 2020/0375781 A1 | 12/2020 | Staali et al. |
| 2020/0375810 A1 | 12/2020 | Carlin et al. |
| 2020/0385179 A1 | 12/2020 | Mccourt |
| 2020/0390591 A1 | 12/2020 | Glithero et al. |
| 2020/0390592 A1 | 12/2020 | Merrill |
| 2020/0405521 A1 | 12/2020 | Glasroe |
| 2021/0008771 A1 | 1/2021 | Huber et al. |
| 2021/0009323 A1 | 1/2021 | Markarian et al. |
| 2021/0020072 A1 | 1/2021 | Moehring et al. |
| 2021/0059853 A1* | 3/2021 | Davis ............... A61F 5/451 |
| 2021/0061523 A1 | 3/2021 | Bytheway |
| 2021/0069005 A1* | 3/2021 | Sanchez ............... A61F 5/4404 |
| 2021/0069008 A1 | 3/2021 | Blabas et al. |
| 2021/0069009 A1 | 3/2021 | Im |
| 2021/0069030 A1 | 3/2021 | Nishikawa et al. |
| 2021/0077993 A1 | 3/2021 | Nazareth et al. |
| 2021/0113749 A1 | 4/2021 | Radl et al. |
| 2021/0121318 A1 | 4/2021 | Pinlac |
| 2021/0137724 A1 | 5/2021 | Ecklund et al. |
| 2021/0138190 A1 | 5/2021 | Erbey et al. |
| 2021/0154055 A1 | 5/2021 | Mllarreal |
| 2021/0170079 A1 | 6/2021 | Radl et al. |
| 2021/0178390 A1 | 6/2021 | Oueslati et al. |
| 2021/0186742 A1 | 6/2021 | Newton et al. |
| 2021/0212865 A1 | 7/2021 | Wallajapet et al. |
| 2021/0220162 A1 | 7/2021 | Jamison |
| 2021/0220163 A1 | 7/2021 | Mayrand |
| 2021/0228400 A1 | 7/2021 | Glithero |
| 2021/0228401 A1 | 7/2021 | Becker et al. |
| 2021/0228795 A1 | 7/2021 | Hughett et al. |
| 2021/0229877 A1 | 7/2021 | Ragias et al. |
| 2021/0236323 A1* | 8/2021 | Austermann ............ A61F 5/451 |
| 2021/0236324 A1 | 8/2021 | Sweeney |
| 2021/0251814 A1 | 8/2021 | Jönegren et al. |
| 2021/0267787 A1 | 9/2021 | Nazemi |
| 2021/0275343 A1* | 9/2021 | Sanchez ............... A61F 5/4404 |
| 2021/0290454 A1 | 9/2021 | Yamada |
| 2021/0315727 A1 | 10/2021 | Jiang |
| 2021/0353450 A1 | 11/2021 | Sharma et al. |
| 2021/0361469 A1 | 11/2021 | Liu et al. |
| 2021/0369495 A1* | 12/2021 | Cheng ............... A61F 5/4405 |
| 2021/0386925 A1 | 12/2021 | Hartwell et al. |
| 2021/0393433 A1 | 12/2021 | Godinez et al. |
| 2022/0023091 A1 | 1/2022 | Ecklund et al. |
| 2022/0031523 A1 | 2/2022 | Pierpoint |
| 2022/0039995 A1 | 2/2022 | Johannes et al. |
| 2022/0047410 A1 | 2/2022 | Walthall |
| 2022/0062027 A1 | 3/2022 | Mitchell et al. |
| 2022/0062028 A1 | 3/2022 | Mitchell et al. |
| 2022/0062029 A1* | 3/2022 | Johannes ............ A61F 5/4401 |
| 2022/0066825 A1 | 3/2022 | Saraf et al. |
| 2022/0071811 A1 | 3/2022 | Cheng et al. |
| 2022/0071826 A1 | 3/2022 | Kulkarni et al. |
| 2022/0104965 A1 | 4/2022 | Vaninetti et al. |
| 2022/0104976 A1 | 4/2022 | Hoeger et al. |
| 2022/0104981 A1 | 4/2022 | Jones |
| 2022/0117773 A1 | 4/2022 | Davis et al. |
| 2022/0117774 A1 | 4/2022 | Meyer et al. |
| 2022/0117775 A1* | 4/2022 | Jones ............... A61L 26/0009 |
| 2022/0133524 A1* | 5/2022 | Davis ............... A61M 1/80 604/319 |
| 2022/0151817 A1 | 5/2022 | Mann |
| 2022/0160949 A1 | 5/2022 | Simiele et al. |
| 2022/0168159 A1 | 6/2022 | Triado et al. |
| 2022/0193312 A1 | 6/2022 | Lee et al. |
| 2022/0211536 A1 | 7/2022 | Johannes et al. |
| 2022/0218510 A1 | 7/2022 | Metzger et al. |
| 2022/0229053 A1 | 7/2022 | Levin et al. |
| 2022/0241106 A1 | 8/2022 | Johannes et al. |
| 2022/0247407 A1 | 8/2022 | Yamamoto et al. |
| 2022/0248836 A1 | 8/2022 | Cagle et al. |
| 2022/0257407 A1* | 8/2022 | Johannes ............ A61F 5/455 |
| 2022/0265460 A1 | 8/2022 | Coker |
| 2022/0265462 A1* | 8/2022 | Alder ............... A61F 5/455 |
| 2022/0270711 A1 | 8/2022 | Feala et al. |
| 2022/0273482 A1 | 9/2022 | Johannes et al. |
| 2022/0280252 A1* | 9/2022 | Jagannathan ........... A61F 13/84 |
| 2022/0287689 A1 | 9/2022 | Johannes |
| 2022/0296408 A1 | 9/2022 | Evans et al. |
| 2022/0305191 A1 | 9/2022 | Joseph et al. |
| 2022/0313222 A1* | 10/2022 | Austermann ........... A61F 5/453 |
| 2022/0313474 A1 | 10/2022 | Kriscovich et al. |
| 2022/0331170 A1 | 10/2022 | Erdem et al. |
| 2022/0339024 A1 | 10/2022 | Johannes et al. |
| 2022/0354685 A1 | 11/2022 | Davis et al. |
| 2022/0362049 A1 | 11/2022 | Austermann et al. |
| 2022/0370231 A1 | 11/2022 | Wang et al. |
| 2022/0370234 A1* | 11/2022 | Hughett ............ A61F 5/451 |
| 2022/0370235 A1* | 11/2022 | Johannes ............ A61F 5/453 |
| 2022/0370237 A1 | 11/2022 | Parmar et al. |
| 2022/0387001 A1 | 12/2022 | Askenazi et al. |
| 2022/0395390 A1 | 12/2022 | Brooks |
| 2022/0395391 A1* | 12/2022 | Saunders ............ A61F 5/4404 |
| 2023/0018845 A1* | 1/2023 | Lee ............... A61F 13/4752 |
| 2023/0020563 A1 | 1/2023 | Sharma et al. |
| 2023/0031640 A1 | 2/2023 | Hughett et al. |
| 2023/0037159 A1* | 2/2023 | Brennan ............ A61F 5/451 |
| 2023/0052238 A1 | 2/2023 | Oluwasogo |
| 2023/0062944 A1 | 3/2023 | Vollenberg et al. |
| 2023/0062994 A1 | 3/2023 | Ecklund et al. |
| 2023/0070347 A1 | 3/2023 | Watson et al. |
| 2023/0073708 A1 | 3/2023 | Xu et al. |
| 2023/0089032 A1* | 3/2023 | Hughett ............ A61F 5/4404 |
| 2023/0099026 A1 | 3/2023 | Radl et al. |
| 2023/0099991 A1 | 3/2023 | Bianchi et al. |
| 2023/0105001 A1* | 4/2023 | Whittome ......... A61F 13/53708 604/319 |
| 2023/0110577 A1 | 4/2023 | Choi |
| 2023/0138269 A1* | 5/2023 | Abdelal ............... A61F 5/451 604/347 |
| 2023/0145365 A1 | 5/2023 | Martin et al. |
| 2023/0155253 A1 | 5/2023 | Yin et al. |
| 2023/0210504 A1 | 7/2023 | Kuroda et al. |
| 2023/0218426 A1 | 7/2023 | Hughett |
| 2023/0240884 A1 | 8/2023 | Davis et al. |
| 2023/0248562 A1 | 8/2023 | Sanchez et al. |
| 2023/0248564 A1 | 8/2023 | Mann et al. |
| 2023/0255812 A1 | 8/2023 | Sanchez et al. |
| 2023/0255813 A1 | 8/2023 | Sanchez et al. |
| 2023/0255815 A1 | 8/2023 | Newton |
| 2023/0263650 A1 | 8/2023 | Sanchez et al. |

(56) References Cited

U.S. PATENT DOCUMENTS

| | | |
|---|---|---|
| 2023/0263655 A1 | 8/2023 | Johannes et al. |
| 2023/0277362 A1* | 9/2023 | Davis .............. A61B 5/208 604/319 |
| 2023/0285178 A1 | 9/2023 | Sanchez et al. |
| 2023/0293339 A1 | 9/2023 | James |
| 2023/0301846 A1 | 9/2023 | Greenwood |
| 2023/0355423 A1 | 11/2023 | Stevenson et al. |
| 2023/0404791 A1 | 12/2023 | Ecklund et al. |
| 2024/0008444 A1 | 1/2024 | Su et al. |
| 2024/0009023 A1 | 1/2024 | Johannes et al. |
| 2024/0024170 A1 | 1/2024 | Scott |
| 2024/0041638 A1 | 2/2024 | Johannes et al. |
| 2024/0058161 A1 | 2/2024 | Ulreich et al. |
| 2024/0065881 A1 | 2/2024 | Kuroda et al. |
| 2024/0099874 A1 | 3/2024 | Sanchez et al. |
| 2024/0110318 A1 | 4/2024 | Bendt et al. |
| 2024/0123134 A1 | 4/2024 | Kharkar et al. |

FOREIGN PATENT DOCUMENTS

| | | |
|---|---|---|
| CA | 2165286 C | 9/1999 |
| CA | 2354132 A1 | 6/2000 |
| CA | 2359091 C | 9/2003 |
| CA | 2488867 C | 8/2007 |
| CA | 3050918 A1 | 8/2018 |
| CA | 3098571 A1 | 11/2019 |
| CN | 2269203 Y | 12/1997 |
| CN | 1332620 A | 1/2002 |
| CN | 1434693 A | 8/2003 |
| CN | 1533755 A | 10/2004 |
| CN | 1602825 A | 4/2005 |
| CN | 1720888 A | 1/2006 |
| CN | 2936204 Y | 8/2007 |
| CN | 101262836 A | 9/2008 |
| CN | 101522148 A | 9/2009 |
| CN | 102159159 A | 8/2011 |
| CN | 202184840 U | 4/2012 |
| CN | 102481441 A | 5/2012 |
| CN | 202463712 U | 10/2012 |
| CN | 103533968 A | 1/2014 |
| CN | 103717180 A | 4/2014 |
| CN | 204562697 U | 8/2015 |
| CN | 105411783 A | 3/2016 |
| CN | 105451693 A | 3/2016 |
| CN | 105534632 A | 5/2016 |
| CN | 205849719 U | 1/2017 |
| CN | 106726089 A | 5/2017 |
| CN | 107847384 A | 3/2018 |
| CN | 107920912 A | 4/2018 |
| CN | 209285902 U | 8/2019 |
| CN | 110381883 A | 10/2019 |
| CN | 211198839 U | 8/2020 |
| CN | 112566550 A | 3/2021 |
| CN | 112603184 A | 4/2021 |
| CN | 114007493 A | 2/2022 |
| CN | 114375187 A | 4/2022 |
| CN | 116096332 A | 5/2023 |
| DE | 79818 C | 10/1893 |
| DE | 1516466 A1 | 6/1969 |
| DE | 2721330 A1 | 11/1977 |
| DE | 2742298 A1 | 3/1978 |
| DE | 9407554.9 U1 | 5/1995 |
| DE | 4443710 A1 | 6/1995 |
| DE | 4416094 A1 | 11/1995 |
| DE | 4236097 C2 | 10/1996 |
| DE | 19619597 A1 | 11/1997 |
| DE | 102005037762 B3 | 9/2006 |
| DE | 102011103783 A1 | 12/2012 |
| DE | 202015104597 U1 | 7/2016 |
| DK | 9600118 | 11/1996 |
| EP | 0032138 A2 | 7/1981 |
| EP | 0066070 B1 | 12/1982 |
| EP | 0068712 A1 | 1/1983 |
| EP | 0140470 A1 | 5/1985 |
| EP | 0140471 B1 | 5/1988 |
| EP | 0274753 A2 | 7/1988 |
| EP | 0119143 B1 | 11/1988 |
| EP | 0483592 A1 | 5/1992 |
| EP | 0610638 A1 | 8/1994 |
| EP | 0613355 A1 | 9/1994 |
| EP | 0613355 B1 | 1/1997 |
| EP | 0787472 A1 | 8/1997 |
| EP | 0966936 A1 | 12/1999 |
| EP | 0987293 A1 | 3/2000 |
| EP | 1063953 A1 | 1/2001 |
| EP | 0653928 B1 | 10/2002 |
| EP | 1332738 A1 | 8/2003 |
| EP | 1382318 A1 | 1/2004 |
| EP | 1089684 B1 | 10/2004 |
| EP | 1616542 A1 | 1/2006 |
| EP | 1382318 B1 | 5/2006 |
| EP | 1063953 B1 | 1/2007 |
| EP | 1872752 A1 | 1/2008 |
| EP | 2180907 A1 | 5/2010 |
| EP | 2380532 A1 | 10/2011 |
| EP | 2389908 A1 | 11/2011 |
| EP | 2601916 A1 | 6/2013 |
| EP | 2676643 A1 | 12/2013 |
| EP | 2997950 A2 | 3/2016 |
| EP | 2879534 B1 | 3/2017 |
| EP | 3424471 A1 | 1/2019 |
| EP | 3169292 B1 | 11/2019 |
| EP | 3753492 A1 | 12/2020 |
| EP | 3788992 A1 | 3/2021 |
| EP | 3576689 B1 | 3/2022 |
| EP | 3752110 B1 | 3/2022 |
| EP | 3787570 B1 | 3/2022 |
| EP | 4025163 A1 | 7/2022 |
| EP | 3463180 B1 | 3/2023 |
| GB | 1011517 A | 12/1965 |
| GB | 1467144 A | 3/1977 |
| GB | 2106395 A | 4/1983 |
| GB | 2106784 A | 4/1983 |
| GB | 2148126 A | 5/1985 |
| GB | 2171315 A | 8/1986 |
| GB | 2181953 A | 5/1987 |
| GB | 2148126 B | 7/1987 |
| GB | 2191095 A | 12/1987 |
| GB | 2199750 A | 7/1988 |
| GB | 2260907 A | 5/1993 |
| GB | 2462267 A | 2/2010 |
| GB | 2469496 A | 10/2010 |
| GB | 2490327 A | 10/2012 |
| GB | 2507318 A | 4/2014 |
| GB | 2612752 A | 5/2023 |
| IT | 201800009129 A1 | 4/2020 |
| JP | S498638 U | 1/1974 |
| JP | S5410596 A | 1/1979 |
| JP | S5410596 Y2 | 5/1979 |
| JP | S55155618 A | 12/1980 |
| JP | S5888596 U | 6/1983 |
| JP | S63107780 U | 7/1988 |
| JP | H0267530 A | 3/1990 |
| JP | H02103871 A | 4/1990 |
| JP | H02131422 A | 5/1990 |
| JP | H02131422 U | 11/1990 |
| JP | H0460220 A | 2/1992 |
| JP | H05123349 A | 5/1993 |
| JP | H05123350 A | 5/1993 |
| JP | 3087938 B2 | 10/1995 |
| JP | H085630 A | 1/1996 |
| JP | H1040141 A | 2/1998 |
| JP | H10225430 A | 8/1998 |
| JP | H11113946 A | 4/1999 |
| JP | H11290365 A | 10/1999 |
| JP | 2000116690 A | 4/2000 |
| JP | 2000185068 A | 7/2000 |
| JP | 2001054531 A | 2/2001 |
| JP | 2001070331 A | 3/2001 |
| JP | 2001224616 A | 8/2001 |
| JP | 2001276107 A | 10/2001 |
| JP | 2001276108 A | 10/2001 |
| JP | 2002028173 A | 1/2002 |

(56) References Cited

FOREIGN PATENT DOCUMENTS

| | | |
|---|---|---|
| JP | 2003505152 A | 2/2003 |
| JP | 2003180722 A | 7/2003 |
| JP | 2004130056 A | 4/2004 |
| JP | 2004267530 A | 9/2004 |
| JP | 2005066011 A | 3/2005 |
| JP | 2005066325 A | 3/2005 |
| JP | 2005518237 A | 6/2005 |
| JP | 3749097 B2 | 12/2005 |
| JP | 2006026108 A | 2/2006 |
| JP | 3123547 B2 | 6/2006 |
| JP | 2006136492 A | 6/2006 |
| JP | 2006204868 A | 8/2006 |
| JP | 2007044494 A | 2/2007 |
| JP | 3132659 B2 | 5/2007 |
| JP | 4039641 B2 | 11/2007 |
| JP | 2009509570 A | 3/2009 |
| JP | 2010081981 A | 4/2010 |
| JP | 4640772 B2 | 12/2010 |
| JP | 2010536439 A | 12/2010 |
| JP | 4747166 B2 | 5/2011 |
| JP | 2011087823 A | 5/2011 |
| JP | 4801218 B1 | 8/2011 |
| JP | 2011218130 A | 11/2011 |
| JP | 2011224070 A | 11/2011 |
| JP | 2012523869 A | 10/2012 |
| JP | 2013238608 A | 11/2013 |
| JP | 2014521960 A | 8/2014 |
| JP | 2015092945 A | 5/2015 |
| JP | 3198994 B2 | 7/2015 |
| JP | 2019525811 A | 9/2019 |
| JP | 2021120686 A | 8/2021 |
| JP | 2021522009 A | 8/2021 |
| JP | 7129493 B2 | 8/2022 |
| JP | 2023532132 A | 7/2023 |
| KR | 200290061 Y1 | 9/2002 |
| KR | 20030047451 A | 6/2003 |
| KR | 20140039485 A | 4/2014 |
| KR | 101432639 B1 | 8/2014 |
| KR | 20180106659 A | 10/2018 |
| KR | 20180108774 A | 10/2018 |
| PT | 2068717 E | 6/2013 |
| WO | 8101957 A1 | 7/1981 |
| WO | 8804558 A1 | 6/1988 |
| WO | 9104714 A2 | 4/1991 |
| WO | 9104714 A3 | 6/1991 |
| WO | 9220299 A3 | 2/1993 |
| WO | 9307839 A1 | 4/1993 |
| WO | 9309736 A2 | 5/1993 |
| WO | 9309736 A3 | 6/1993 |
| WO | 9514448 A2 | 6/1995 |
| WO | 9600096 A1 | 1/1996 |
| WO | 9634636 A1 | 11/1996 |
| WO | 9817211 A1 | 4/1998 |
| WO | 9830336 A1 | 7/1998 |
| WO | 0000112 A1 | 1/2000 |
| WO | 0000113 A1 | 1/2000 |
| WO | 0025651 A1 | 5/2000 |
| WO | 0033773 A1 | 6/2000 |
| WO | 0057784 A1 | 10/2000 |
| WO | 0069377 A1 | 11/2000 |
| WO | 0079497 A1 | 12/2000 |
| WO | 0145618 A1 | 6/2001 |
| WO | 0145621 A1 | 6/2001 |
| WO | 02094160 A1 | 11/2002 |
| WO | 03013967 A1 | 2/2003 |
| WO | 03024824 A1 | 3/2003 |
| WO | 03055423 A1 | 7/2003 |
| WO | 03071931 A2 | 9/2003 |
| WO | 03079942 A1 | 10/2003 |
| WO | 03071931 A3 | 2/2004 |
| WO | 2004019836 A1 | 3/2004 |
| WO | 2004024046 A1 | 3/2004 |
| WO | 2005051252 A1 | 6/2005 |
| WO | 2005074571 A3 | 9/2005 |
| WO | 2005089687 A2 | 9/2005 |
| WO | 2005107661 A2 | 11/2005 |
| WO | 2006021220 A1 | 3/2006 |
| WO | 2006037140 A2 | 4/2006 |
| WO | 2007005851 A2 | 1/2007 |
| WO | 2007007845 A1 | 1/2007 |
| WO | 2007042823 A2 | 4/2007 |
| WO | 2007055651 A1 | 5/2007 |
| WO | 2006098950 A3 | 11/2007 |
| WO | 2007134608 A2 | 11/2007 |
| WO | 2007128156 A3 | 2/2008 |
| WO | 2008026106 A2 | 3/2008 |
| WO | 2008078117 A1 | 7/2008 |
| WO | 2008104019 A1 | 9/2008 |
| WO | 2008141471 A1 | 11/2008 |
| WO | 2009004368 A1 | 1/2009 |
| WO | 2009004369 A1 | 1/2009 |
| WO | 2009052496 A1 | 4/2009 |
| WO | 2009052502 A1 | 4/2009 |
| WO | 2009007702 A4 | 7/2009 |
| WO | 2009101738 A1 | 8/2009 |
| WO | 2010058192 A1 | 5/2010 |
| WO | 2010030122 A3 | 7/2010 |
| WO | 2010101915 A3 | 1/2011 |
| WO | 2011018132 A1 | 2/2011 |
| WO | 2011018133 A1 | 2/2011 |
| WO | 2011024864 A1 | 3/2011 |
| WO | 2011054118 A1 | 5/2011 |
| WO | 2011079132 A1 | 6/2011 |
| WO | 2011107972 A1 | 9/2011 |
| WO | 2011108972 A1 | 9/2011 |
| WO | 2011117292 A1 | 9/2011 |
| WO | 2011123219 A1 | 10/2011 |
| WO | 2011132043 A1 | 10/2011 |
| WO | 2012012908 A1 | 2/2012 |
| WO | 2012065274 A1 | 5/2012 |
| WO | 2012097462 A1 | 7/2012 |
| WO | 2012098796 A1 | 7/2012 |
| WO | 2012101288 A1 | 8/2012 |
| WO | 2012175916 A1 | 12/2012 |
| WO | 2013018435 A1 | 2/2013 |
| WO | 2013033429 A1 | 3/2013 |
| WO | 2013055434 A1 | 4/2013 |
| WO | 2013082397 A1 | 6/2013 |
| WO | 2013103291 A2 | 7/2013 |
| WO | 2013131109 A1 | 9/2013 |
| WO | 2013167478 A1 | 11/2013 |
| WO | 2013177716 A1 | 12/2013 |
| WO | 2014041534 A1 | 3/2014 |
| WO | 2014046420 A1 | 3/2014 |
| WO | 2014118518 A1 | 8/2014 |
| WO | 2014160852 A1 | 10/2014 |
| WO | 2015023599 A1 | 2/2015 |
| WO | 2015052348 A1 | 4/2015 |
| WO | 2015068384 A1 | 5/2015 |
| WO | 2015169403 A1 | 11/2015 |
| WO | 2015170307 A1 | 11/2015 |
| WO | 2015197462 A1 | 12/2015 |
| WO | 2016051385 A1 | 4/2016 |
| WO | 2016055989 A1 | 4/2016 |
| WO | 2016071894 A1 | 5/2016 |
| WO | 2016103242 A1 | 6/2016 |
| WO | 2016116915 A1 | 7/2016 |
| WO | 2016124203 A1 | 8/2016 |
| WO | 2016139448 A1 | 9/2016 |
| WO | 2016166562 A1 | 10/2016 |
| WO | 2016167535 A1 | 10/2016 |
| WO | 2016191574 A1 | 12/2016 |
| WO | 2016200088 A1 | 12/2016 |
| WO | 2016200361 A1 | 12/2016 |
| WO | 2016204731 A1 | 12/2016 |
| WO | 2017001532 A2 | 1/2017 |
| WO | 2017001846 A1 | 1/2017 |
| WO | 2017075226 A1 | 5/2017 |
| WO | 2017152198 A1 | 9/2017 |
| WO | 2017153357 A1 | 9/2017 |
| WO | 2017162559 A1 | 9/2017 |
| WO | 2017205446 A1 | 11/2017 |
| WO | 2017209779 A1 | 12/2017 |
| WO | 2017210524 A1 | 12/2017 |

(56) References Cited

FOREIGN PATENT DOCUMENTS

| | | |
|---|---|---|
| WO | 2018022414 A1 | 2/2018 |
| WO | 2018044781 A1 | 3/2018 |
| WO | 2018056953 A1 | 3/2018 |
| WO | 2018090550 A1 | 5/2018 |
| WO | 2018138513 A1 | 8/2018 |
| WO | 2018144318 A1 | 8/2018 |
| WO | 2018144463 A1 | 8/2018 |
| WO | 2018150263 A1 | 8/2018 |
| WO | 2018150268 A1 | 8/2018 |
| WO | 2018152156 A1 | 8/2018 |
| WO | 2018183791 A1 | 10/2018 |
| WO | 2018150267 A3 | 11/2018 |
| WO | 2018235026 A1 | 12/2018 |
| WO | 2018235065 A1 | 12/2018 |
| WO | 2019004404 A1 | 1/2019 |
| WO | 2019041005 A1 | 3/2019 |
| WO | 2019044217 A1 | 3/2019 |
| WO | 2019044218 A1 | 3/2019 |
| WO | 2019044219 A1 | 3/2019 |
| WO | 2019065541 A1 | 4/2019 |
| WO | 2019096845 A1 | 5/2019 |
| WO | 2019150385 A1 | 8/2019 |
| WO | 2019161094 A1 | 8/2019 |
| WO | 2019188566 A1 | 10/2019 |
| WO | 2019190593 A1 | 10/2019 |
| WO | 2019212949 A1 | 11/2019 |
| WO | 2019212950 A1 | 11/2019 |
| WO | 2019212951 A1 | 11/2019 |
| WO | 2019212952 A1 | 11/2019 |
| WO | 2019212954 A1 | 11/2019 |
| WO | 2019212955 A1 | 11/2019 |
| WO | 2019212956 A1 | 11/2019 |
| WO | 2019214787 A1 | 11/2019 |
| WO | 2019214788 A1 | 11/2019 |
| WO | 2019226826 A1 | 11/2019 |
| WO | 2019239433 A1 | 12/2019 |
| WO | 2020000994 A1 | 1/2020 |
| WO | 2020020618 A1 | 1/2020 |
| WO | 2020038822 A1 | 2/2020 |
| WO | 2020088409 A1 | 5/2020 |
| WO | 2020049394 A3 | 6/2020 |
| WO | 2020120657 A1 | 6/2020 |
| WO | 2020152575 A1 | 7/2020 |
| WO | 2020182923 A1 | 9/2020 |
| WO | 2020204967 A1 | 10/2020 |
| WO | 2020205939 A1 | 10/2020 |
| WO | 2020209898 A1 | 10/2020 |
| WO | 2020242790 A1 | 12/2020 |
| WO | 2020251893 A1 | 12/2020 |
| WO | 2020256865 A1 | 12/2020 |
| WO | 2021007144 A1 | 1/2021 |
| WO | 2021007345 A1 | 1/2021 |
| WO | 2021010844 A1 | 1/2021 |
| WO | 2021016026 A1 | 1/2021 |
| WO | 2021016300 A1 | 1/2021 |
| WO | 2021025919 A1 | 2/2021 |
| WO | 2021034886 A1 | 2/2021 |
| WO | 2021041123 A1 | 3/2021 |
| WO | 2021046501 A1 | 3/2021 |
| WO | 2021086868 A1 | 5/2021 |
| WO | 2021094352 A1 | 5/2021 |
| WO | 2021094639 A1 | 5/2021 |
| WO | 2021097067 A1 | 5/2021 |
| WO | 2021102296 A1 | 5/2021 |
| WO | 2021107025 A1 | 6/2021 |
| WO | 2021138411 A1 | 7/2021 |
| WO | 2021138414 A1 | 7/2021 |
| WO | 2021154686 A1 | 8/2021 |
| WO | 2021155206 A1 | 8/2021 |
| WO | 2021170075 A1 | 9/2021 |
| WO | 2021173436 A1 | 9/2021 |
| WO | 2021188817 A1 | 9/2021 |
| WO | 2021195384 A1 | 9/2021 |
| WO | 2021205995 A1 | 10/2021 |
| WO | 2021207621 A1 | 10/2021 |
| WO | 2021211568 A1 | 10/2021 |
| WO | 2021211801 A1 | 10/2021 |
| WO | 2021211914 A1 | 10/2021 |
| WO | 2021216419 A1 | 10/2021 |
| WO | 2021216422 A1 | 10/2021 |
| WO | 2021231532 A1 | 11/2021 |
| WO | 2021247523 A1 | 12/2021 |
| WO | 2021257202 A1 | 12/2021 |
| WO | 2022006256 A1 | 1/2022 |
| WO | 2022031943 A1 | 2/2022 |
| WO | 2022035745 A1 | 2/2022 |
| WO | 2022051360 A1 | 3/2022 |
| WO | 2022054613 A1 | 3/2022 |
| WO | 2022066704 A1 | 3/2022 |
| WO | 2022067392 A1 | 4/2022 |
| WO | 2022069950 A1 | 4/2022 |
| WO | 2022071429 A1 | 4/2022 |
| WO | 2022076322 A1 | 4/2022 |
| WO | 2022076427 A2 | 4/2022 |
| WO | 2022086898 A1 | 4/2022 |
| WO | 2022090199 A1 | 5/2022 |
| WO | 2022098536 A1 | 5/2022 |
| WO | 2022099087 A1 | 5/2022 |
| WO | 2022101999 A1 | 5/2022 |
| WO | 2022115692 A1 | 6/2022 |
| WO | 2022125685 A1 | 6/2022 |
| WO | 2022140545 A1 | 6/2022 |
| WO | 2022145231 A1 | 7/2022 |
| WO | 2022150360 A1 | 7/2022 |
| WO | 2022150463 A1 | 7/2022 |
| WO | 2022159392 A1 | 7/2022 |
| WO | 2022170182 A1 | 8/2022 |
| WO | 2022182385 A1 | 9/2022 |
| WO | 2022187152 A1 | 9/2022 |
| WO | 2022192188 A1 | 9/2022 |
| WO | 2022192347 A1 | 9/2022 |
| WO | 2022216507 A1 | 10/2022 |
| WO | 2022222030 A1 | 10/2022 |
| WO | 2023286058 A1 | 1/2023 |
| WO | 2023014639 A1 | 2/2023 |
| WO | 2023014641 A1 | 2/2023 |
| WO | 2023018475 A2 | 2/2023 |
| WO | 2023023777 A1 | 3/2023 |
| WO | 2023034453 A1 | 3/2023 |
| WO | 2023038945 A1 | 3/2023 |
| WO | 2023038950 A1 | 3/2023 |
| WO | 2023049109 A1 | 3/2023 |
| WO | 2023049175 A1 | 3/2023 |
| WO | 2023086394 A1 | 5/2023 |
| WO | 2023149884 A1 | 8/2023 |
| WO | 2023149902 A1 | 8/2023 |
| WO | 2023149903 A1 | 8/2023 |
| WO | 2023154390 A1 | 8/2023 |
| WO | 2023191764 A1 | 10/2023 |
| WO | 2023244238 A1 | 12/2023 |
| WO | 2024058788 A1 | 3/2024 |

OTHER PUBLICATIONS

Advisory Action for U.S. Appl. No. 14/722,613 dated Mar. 4, 2019.
Advisory Action for U.S. Appl. No. 14/952,591 dated Jun. 1, 2018.
Advisory Action for U.S. Appl. No. 15/238,427 dated Apr. 10, 2019.
Advisory Action for U.S. Appl. No. 16/899,956 dated Jul. 9, 2021.
Advisory Action for U.S. Appl. No. 16/904,868 dated Jul. 2, 2021.
Advisory Action for U.S. Appl. No. 16/905,400 dated Feb. 16, 2022.
Advisory Action for U.S. Appl. No. 16/905,400 dated Jun. 9, 2021.
Corrected International Search Report and Written Opinion for International Application No. PCT/US2017/043025 dated Jan. 11, 2018.
Corrected Notice of Allowability for U.S. Appl. No. 15/221,106 dated Jul. 2, 2019.
Corrected Notice of Allowability for U.S. Appl. No. 15/612,325 dated Mar. 17, 2021.
Corrected Notice of Allowability for U.S. Appl. No. 17/330,657 dated Dec. 9, 2021.
Final Office Action for U.S. Appl. No. 14/722,613 dated Nov. 29, 2018.

(56) References Cited

OTHER PUBLICATIONS

Final Office Action for U.S. Appl. No. 14/947,759 dated Apr. 8, 2016.
Final Office Action for U.S. Appl. No. 14/952,591 dated Feb. 23, 2018.
Final Office Action for U.S. Appl. No. 14/952,591 dated Nov. 1, 2019.
Final Office Action for U.S. Appl. No. 14/952,591 dated Nov. 27, 2020.
Final Office Action for U.S. Appl. No. 15/171,968 dated Feb. 14, 2020.
Final Office Action for U.S. Appl. No. 15/171,968 dated Mar. 19, 2019.
Final Office Action for U.S. Appl. No. 15/221,106 dated Jan. 23, 2019.
Final Office Action for U.S. Appl. No. 15/238,427 dated Jan. 2, 2019.
Final Office Action for U.S. Appl. No. 15/260,103 dated Feb. 14, 2019.
Final Office Action for U.S. Appl. No. 15/612,325 dated Sep. 17, 2020.
Final Office Action for U.S. Appl. No. 16/452,145 dated Mar. 25, 2022.
Final Office Action for U.S. Appl. No. 16/899,956 dated Apr. 19, 2021.
Final Office Action for U.S. Appl. No. 16/904,868 dated Mar. 10, 2022.
Final Office Action for U.S. Appl. No. 16/904,868 dated Mar. 26, 2021.
Final Office Action for U.S. Appl. No. 16/905,400 dated Apr. 6, 2021.
Final Office Action for U.S. Appl. No. 16/905,400 dated Dec. 9, 2021.
Final Office Action for U.S. Appl. No. 17/088,272 dated May 25, 2021.
Final Office Action for U.S. Appl. No. 29/624,661 dated Feb. 18, 2020.
International Search Report and Written Opinion from International Application No. PCT/US2016/049274 dated Dec. 1, 2016.
International Search Report and Written Opinion from International Application No. PCT/US2017/035625 dated Aug. 15, 2017.
International Search Report and Written Opinion from International Application No. PCT/US2017/043025 dated Oct. 18, 2017.
International Search Report and Written Opinion from International Application No. PCT/US2018/015968 dated Apr. 6, 2018.
International Search Report and Written Opinion from International Application No. PCT/US2019/029608 dated Sep. 3, 2019.
International Search Report and Written Opinion from International Application No. PCT/US2019/029609 dated Sep. 3, 2019.
International Search Report and Written Opinion from International Application No. PCT/US2019/029610 dated Sep. 3, 2019.
International Search Report and Written Opinion from International Application No. PCT/US2019/029611 dated Jul. 3, 2019.
International Search Report and Written Opinion from International Application No. PCT/US2019/029613 dated Jul. 3, 2019.
International Search Report and Written Opinion from International Application No. PCT/US2019/029614 dated Sep. 26, 2019.
International Search Report and Written Opinion from International Application No. PCT/US2019/029616 dated Aug. 30, 2019.
International Search Report and Written Opinion from International Application No. PCT/US2020/023572 dated Jul. 6, 2020.
International Search Report and Written Opinion from International Application No. PCT/US2020/033064 dated Aug. 31, 2020.
International Search Report and Written Opinion from International Application No. PCT/US2020/033122 dated Aug. 31, 2020.
International Search Report and Written Opinion from International Application No. PCT/US2020/040860 dated Oct. 2, 2020.
International Search Report and Written Opinion from International Application No. PCT/US2020/041242 dated Nov. 17, 2020.
International Search Report and Written Opinion from International Application No. PCT/US2020/041249 dated Oct. 2, 2020.
International Search Report and Written Opinion from International Application No. PCT/US2020/042262 dated Oct. 14, 2020.
International Search Report and Written Opinion from International Application No. PCT/US2020/043059 dated Oct. 6, 2020.
International Search Report and Written Opinion from International Application No. PCT/US2020/044024 dated Nov. 12, 2020.
International Search Report and Written Opinion from International Application No. PCT/US2020/046914 dated Dec. 1, 2020.
International Search Report and Written Opinion from International Application No. PCT/US2020/055680 dated Dec. 15, 2020.
International Search Report and Written Opinion from International Application No. PCT/US2020/057562 dated Jan. 27, 2021.
International Search Report and Written Opinion from International Application No. PCT/US2020/061563 dated Feb. 19, 2021.
International Search Report and Written Opinion from International Application No. PCT/US2020/065234 dated Apr. 12, 2021.
International Search Report and Written Opinion from International Application No. PCT/US2020/067451 dated Mar. 25, 2021.
International Search Report and Written Opinion from International Application No. PCT/US2020/067454 dated Mar. 29, 2021.
International Search Report and Written Opinion from International Application No. PCT/US2020/067455 dated Mar. 26, 2021.
International Search Report and Written Opinion from International Application No. PCT/US2021/015024 dated May 18, 2021.
International Search Report and Written Opinion from International Application No. PCT/US2021/015787 dated May 27, 2021.
International Search Report and Written Opinion from International Application No. PCT/US2021/023001 dated Jun. 21, 2021.
International Search Report and Written Opinion from International Application No. PCT/US2021/024162 dated Jul. 8, 2021.
International Search Report and Written Opinion from International Application No. PCT/US2021/026607 dated Jul. 29, 2021.
International Search Report and Written Opinion from International Application No. PCT/US2021/027061 dated Jul. 19, 2021.
International Search Report and Written Opinion from International Application No. PCT/US2021/027104 dated Jul. 6, 2021.
International Search Report and Written Opinion from International Application No. PCT/US2021/027314 dated Jul. 6, 2021.
International Search Report and Written Opinion from International Application No. PCT/US2021/027422 dated Aug. 12, 2021.
International Search Report and Written Opinion from International Application No. PCT/US2021/027425 dated Aug. 11, 2021.
International Search Report and Written Opinion from International Application No. PCT/US2021/027913 dated Jul. 12, 2021.
International Search Report and Written Opinion from International Application No. PCT/US2021/027917 dated Aug. 19, 2021.
International Search Report and Written Opinion from International Application No. PCT/US2021/035181 dated Sep. 16, 2021.
International Search Report and Written Opinion from International Application No. PCT/US2021/043893 dated Nov. 22, 2021.
International Search Report and Written Opinion from International Application No. PCT/US2021/044699 dated Nov. 22, 2021.
International Search Report and Written Opinion from International Application No. PCT/US2021/045188 dated Jan. 26, 2022.
International Search Report and Written Opinion from International Application No. PCT/US2021/047536 dated Dec. 23, 2021.
International Search Report and Written Opinion from International Application No. PCT/US2021/048211 dated Dec. 22, 2021.
International Search Report and Written Opinion from International Application No. PCT/US2021/048661 dated Feb. 14, 2022.
International Search Report and Written Opinion from International Application No. PCT/US2021/049404 dated Jan. 18, 2022.
International Search Report and Written Opinion from International Application No. PCT/US2021/053593 dated Apr. 11, 2022.
International Search Report and Written Opinion from International Application No. PCT/US2021/056566 dated Feb. 11, 2022.
International Search Report and Written Opinion from International Application No. PCT/US2021/060993 dated Mar. 18, 2022.
International Search Report and Written Opinion from International Application No. PCT/US2021/062440 dated Mar. 28, 2022.

(56) References Cited

OTHER PUBLICATIONS

International Search Report and Written Opinion from International Application No. PCT/US2022/011108 dated Apr. 22, 2022.
International Search Report and Written Opinion from International Application No. PCT/US2022/011281 dated Apr. 25, 2022.
Issue Notification for U.S. Appl. No. 14/952,591 dated Jul. 28, 2021.
Issue Notification for U.S. Appl. No. 15/171,968 dated Mar. 3, 2021.
Issue Notification for U.S. Appl. No. 15/221,106 dated Jul. 24, 2019.
Issue Notification for U.S. Appl. No. 15/238,427 dated Jul. 24, 2019.
Issue Notification for U.S. Appl. No. 15/260,103 dated Aug. 7, 2019.
Issue Notification for U.S. Appl. No. 15/611,587 dated Feb. 20, 2019.
Issue Notification for U.S. Appl. No. 15/612,325 dated Mar. 24, 2021.
Issue Notification for U.S. Appl. No. 29/624,661 dated Aug. 4, 2021.
Non-Final Office Action for U.S. Appl. No. 14/592,591 dated Mar. 20, 2020.
Non-Final Office Action for U.S. Appl. No. 14/722,613 dated Jun. 13, 2019.
Non-Final Office Action for U.S. Appl. No. 14/947,759 dated Mar. 17, 2016.
Non-Final Office Action for U.S. Appl. No. 14/952,591 dated Aug. 1, 2017.
Non-Final Office Action for U.S. Appl. No. 14/952,591 dated Mar. 20, 2020.
Non-Final Office Action for U.S. Appl. No. 14/952,591 dated Mar. 21, 2019.
Non-Final Office Action for U.S. Appl. No. 14/952,591 dated Sep. 28, 2018.
Non-Final Office Action for U.S. Appl. No. 15/171,968 dated May 11, 2020.
Non-Final Office Action for U.S. Appl. No. 15/171,968 dated Aug. 20, 2019.
Non-Final Office Action for U.S. Appl. No. 15/171,968 dated Jun. 12, 2018.
Non-Final Office Action for U.S. Appl. No. 15/221,106 dated Jun. 5, 2018.
Non-Final Office Action for U.S. Appl. No. 15/238,427 dated Aug. 8, 2018.
Non-Final Office Action for U.S. Appl. No. 15/260,103 dated Sep. 26, 2018.
Non-Final Office Action for U.S. Appl. No. 15/611,587 dated Dec. 29, 2017.
Non-Final Office Action for U.S. Appl. No. 15/611,587 dated Jul. 13, 2018.
Non-Final Office Action for U.S. Appl. No. 15/612,325 dated Mar. 19, 2020.
Non-Final Office Action for U.S. Appl. No. 16/245,726 dated Jan. 21, 2022.
Non-Final Office Action for U.S. Appl. No. 16/369,676 dated Mar. 31, 2022.
Non-Final Office Action for U.S. Appl. No. 16/433,773 dated Apr. 21, 2022.
Non-Final Office Action for U.S. Appl. No. 16/449,039 dated Dec. 8, 2021.
Non-Final Office Action for U.S. Appl. No. 16/452,145 dated Sep. 28, 2021.
Non-Final Office Action for U.S. Appl. No. 16/452,258 dated Sep. 28, 2021.
Non-Final Office Action for U.S. Appl. No. 16/478,180 dated Oct. 22, 2021.
Non-Final Office Action for U.S. Appl. No. 16/899,956 dated Oct. 16, 2020.
Non-Final Office Action for U.S. Appl. No. 16/899,956 dated Sep. 2, 2021.
Non-Final Office Action for U.S. Appl. No. 16/904,868 dated Nov. 25, 2020.
Non-Final Office Action for U.S. Appl. No. 16/904,868 dated Oct. 5, 2021.
Non-Final Office Action for U.S. Appl. No. 16/905,400 dated Apr. 27, 2022.
Non-Final Office Action for U.S. Appl. No. 16/905,400 dated Dec. 2, 2020.
Non-Final Office Action for U.S. Appl. No. 16/905,400 dated Jul. 22, 2021.
Non-Final Office Action for U.S. Appl. No. 17/088,272 dated Jan. 25, 2021.
Non-Final Office Action for U.S. Appl. No. 17/330,657 dated Aug. 11, 2021.
Non-Final Office Action for U.S. Appl. No. 29/624,661 dated Jul. 18, 2019.
Non-Final Office Action for U.S. Appl. No. 29/694,002 dated Jun. 24, 2020.
Non-Final Office Action for U.S. Appl. No. 29/741,751 dated Jan. 18, 2022.
Notice of Allowance for U.S. Appl. No. 14/952,591 dated Apr. 5, 2021.
Notice of Allowance for U.S. Appl. No. 14/952,591 dated Jul. 8, 2021.
Notice of Allowance for U.S. Appl. No. 15/171,968 dated Feb. 16, 2021.
Notice of Allowance for U.S. Appl. No. 15/171,968 dated Nov. 6, 2020.
Notice of Allowance for U.S. Appl. No. 15/221,106 dated May 1, 2019.
Notice of Allowance for U.S. Appl. No. 15/238,427 dated May 23, 2019.
Notice of Allowance for U.S. Appl. No. 15/260,103 dated Jun. 7, 2019.
Notice of Allowance for U.S. Appl. No. 15/611,587 dated Dec. 21, 2018.
Notice of Allowance for U.S. Appl. No. 15/612,325 dated Feb. 19, 2021.
Notice of Allowance for U.S. Appl. No. 15/612,325 dated Jan. 21, 2021.
Notice of Allowance for U.S. Appl. No. 16/899,956 dated Apr. 19, 2022.
Notice of Allowance for U.S. Appl. No. 16/899,956 dated Dec. 29, 2021.
Notice of Allowance for U.S. Appl. No. 17/088,272 dated Aug. 5, 2021.
Notice of Allowance for U.S. Appl. No. 17/088,272 dated Mar. 4, 2022.
Notice of Allowance for U.S. Appl. No. 17/088,272 dated Nov. 24, 2021.
Notice of Allowance for U.S. Appl. No. 17/330,657 dated Mar. 16, 2022.
Notice of Allowance for U.S. Appl. No. 17/330,657 dated Nov. 26, 2021.
Notice of Allowance for U.S. Appl. No. 29/624,661 datedd Apr. 28, 2021.
Notice of Allowance for U.S. Appl. No. 29/624,661 dated Jul. 10, 2020.
Notice of Allowance for U.S. Appl. No. 29/624,661 dated May 14, 2020.
Notice of Allowance for U.S. Appl. No. 29/624,661 dated Sep. 29, 2020.
Notice of Allowance for U.S. Appl. No. 29/694,002 dated Apr. 29, 2021.
Notice of Allowance for U.S. Appl. No. 29/694,002 dated Jan. 29, 2021.
Notice of Allowance for U.S. Appl. No. 29/694,002 dated Oct. 16, 2020.
Notice to File Missing Parts for U.S. Appl. No. 17/179,116 mailed Mar. 3, 2021.
Restriction Requirement for U.S. Appl. No. 16/433,773 dated Dec. 7, 2021.

(56) References Cited

OTHER PUBLICATIONS

Restriction Requirement for U.S. Appl. No. 16/478,180 dated May 25, 2021.
U.S. Appl. No. 14/625,469, filed Feb. 28, 2015.
U.S. Appl. No. 14/947,759, filed Nov. 20, 2015.
U.S. Appl. No. 14/952,591, filed Nov. 25, 2015.
U.S. Appl. No. 15/171,968, filed Jun. 2, 2016.
U.S. Appl. No. 15/221,106, filed Jul. 27, 2016.
U.S. Appl. No. 15/260,103, filed Sep. 8, 2016.
U.S. Appl. No. 15/384,196, filed Dec. 19, 2016.
U.S. Appl. No. 15/611,587, filed Jun. 1, 2017.
U.S. Appl. No. 15/612,325, filed Jun. 2, 2017.
U.S. Appl. No. 16/245,726, filed Jan. 11, 2019.
U.S. Appl. No. 16/369,676, filed Mar. 29, 2019.
U.S. Appl. No. 16/433,773, filed Jun. 6, 2019.
U.S. Appl. No. 16/449,039, filed Jun. 21, 2019.
U.S. Appl. No. 16/452,145, filed Jun. 25, 2019.
U.S. Appl. No. 16/452,258, filed Jun. 25, 2019.
U.S. Appl. No. 16/478,180, filed Jul. 16, 2019.
U.S. Appl. No. 16/904,868, filed Jun. 18, 2020.
U.S. Appl. No. 16/905,400, filed Jun. 18, 2020.
U.S. Appl. No. 17/051,550, filed Oct. 29, 2020.
U.S. Appl. No. 17/051,554, filed Oct. 29, 2020.
U.S. Appl. No. 17/051,585, filed Oct. 29, 2020.
U.S. Appl. No. 17/051,600, filed Oct. 29, 2020.
U.S. Appl. No. 17/088,272, filed Nov. 3, 2020.
U.S. Appl. No. 17/179,116, filed Feb. 18, 2021.
U.S. Appl. No. 17/330,657, filed May 26, 2021.
U.S. Appl. No. 17/378,015, filed Jul. 16, 2021.
U.S. Appl. No. 17/394,055, filed Aug. 4, 2021.
U.S. Appl. No. 17/412,864, filed Aug. 26, 2021.
U.S. Appl. No. 17/444,825, filed Aug. 10, 2021.
U.S. Appl. No. 17/446,256, filed Aug. 27, 2021.
U.S. Appl. No. 17/446,654, filed Sep. 1, 2021.
U.S. Appl. No. 17/447,123, filed Sep. 8, 2021.
U.S. Appl. No. 17/450,864, filed Oct. 14, 2021.
U.S. Appl. No. 17/451,345, filed Oct. 19, 2021.
U.S. Appl. No. 17/451,354, filed Oct. 19, 2021.
U.S. Appl. No. 17/453,260, filed Nov. 2, 2021.
U.S. Appl. No. 17/453,560, filed Nov. 4, 2021.
U.S. Appl. No. 17/461,036 mailed Aug. 30, 2021.
U.S. Appl. No. 17/494,578, filed Oct. 5, 2021.
U.S. Appl. No. 17/501,591, filed Oct. 14, 2021.
U.S. Appl. No. 17/595,747, filed Nov. 23, 2021.
U.S. Appl. No. 17/597,408, filed Jan. 5, 2022.
U.S. Appl. No. 17/597,673, filed Jan. 18, 2022.
U.S. Appl. No. 17/614,173, filed Nov. 24, 2021.
U.S. Appl. No. 17/631,619, filed Jan. 31, 2022.
U.S. Appl. No. 17/645,821, filed Dec. 23, 2021.
U.S. Appl. No. 17/646,771, filed Jan. 3, 2022.
U.S. Appl. No. 17/653,314, filed Mar. 3, 2022.
U.S. Appl. No. 17/653,920, filed Mar. 8, 2022.
U.S. Appl. No. 17/654,156, filed Mar. 9, 2022.
U.S. Appl. No. 17/655,464, filed Mar. 18, 2022.
U.S. Appl. No. 17/657,474, filed Mar. 31, 2022.
U.S. Appl. No. 17/661,090, filed Apr. 28, 2022.
U.S. Appl. No. 17/754,736, filed Apr. 11, 2022.
U.S. Appl. No. 29/741,751, filed Jul. 15, 2020.
U.S. Appl. No. 61/955,537, filed Mar. 19, 2014.
U.S. Appl. No. 62/082,279, filed Nov. 20, 2014.
U.S. Appl. No. 62/084,078, filed Nov. 25, 2014.
U.S. Appl. No. 62/414,963, filed Oct. 31, 2016.
U.S. Appl. No. 62/452,437, filed Jan. 31, 2017.
U.S. Appl. No. 62/485,578, filed Apr. 14, 2017.
U.S. Appl. No. 62/665,297, filed May 1, 2018.
U.S. Appl. No. 62/665,302, filed May 1, 2018.
U.S. Appl. No. 62/665,317, filed May 1, 2018.
U.S. Appl. No. 62/665,321, filed May 1, 2018.
U.S. Appl. No. 62/665,331, filed May 1, 2018.
U.S. Appl. No. 62/665,335, filed May 1, 2018.
U.S. Appl. No. 62/853,279, filed May 28, 2019.
U.S. Appl. No. 62/853,889, filed May 29, 2019.
U.S. Appl. No. 62/864,656, filed Jun. 21, 2019.
U.S. Appl. No. 62/873,045, filed Jul. 11, 2019.
U.S. Appl. No. 62/873,048, filed Jul. 11, 2019.
U.S. Appl. No. 62/876,500, filed Jul. 19, 2019.
U.S. Appl. No. 62/877,558, filed Jul. 23, 2019.
U.S. Appl. No. 62/883,172, filed Aug. 6, 2019.
U.S. Appl. No. 62/889,149, filed Aug. 20, 2019.
U.S. Appl. No. 62/923,279, filed Oct. 18, 2019.
U.S. Appl. No. 62/926,767, filed Oct. 28, 2019.
U.S. Appl. No. 62/935,337, filed Nov. 14, 2019.
U.S. Appl. No. 62/938,447, filed Nov. 21, 2019.
U.S. Appl. No. 62/949,187, filed Dec. 17, 2019.
U.S. Appl. No. 62/956,756, filed Jan. 3, 2020.
U.S. Appl. No. 62/956,767, filed Jan. 3, 2020.
U.S. Appl. No. 62/956,770, filed Jan. 3, 2020.
U.S. Appl. No. 62/967,977, filed Jan. 30, 2020.
U.S. Appl. No. 62/994,912, filed Mar. 26, 2020.
U.S. Appl. No. 63/008,112, filed Apr. 10, 2020.
U.S. Appl. No. 63/011,445, filed Apr. 17, 2020.
U.S. Appl. No. 63/011,487, filed Apr. 17, 2020.
U.S. Appl. No. 63/011,571, filed Apr. 17, 2020.
U.S. Appl. No. 63/011,657, filed Apr. 17, 2020.
U.S. Appl. No. 63/011,760, filed Apr. 17, 2020.
U.S. Appl. No. 63/012,347, filed Apr. 20, 2020.
U.S. Appl. No. 63/012,384, filed Apr. 20, 2020.
U.S. Appl. No. 63/030,685, filed May 27, 2020.
U.S. Appl. No. 63/033,310, filed Jun. 2, 2020.
U.S. Appl. No. 63/047,374, filed Jul. 2, 2020.
U.S. Appl. No. 63/061,241, filed Aug. 5, 2020.
U.S. Appl. No. 63/061,244, filed Aug. 5, 2020.
U.S. Appl. No. 63/061,834, filed Aug. 6, 2020.
U.S. Appl. No. 63/064,017, filed Aug. 11, 2020.
U.S. Appl. No. 63/064,126, filed Aug. 11, 2020.
U.S. Appl. No. 63/067,542, filed Aug. 19, 2020.
U.S. Appl. No. 63/071,438, filed Aug. 28, 2020.
U.S. Appl. No. 63/071,821, filed Aug. 28, 2020.
U.S. Appl. No. 63/073,545, filed Sep. 2, 2020.
U.S. Appl. No. 63/073,553, filed Sep. 2, 2020.
U.S. Appl. No. 63/074,051, filed Sep. 3, 2020.
U.S. Appl. No. 63/074,066, filed Sep. 3, 2020.
U.S. Appl. No. 63/076,032, filed Sep. 9, 2020.
U.S. Appl. No. 63/076,474, filed Sep. 10, 2020.
U.S. Appl. No. 63/076,477, filed Sep. 10, 2020.
U.S. Appl. No. 63/082,261, filed Sep. 23, 2020.
U.S. Appl. No. 63/088,506, filed Oct. 7, 2020.
U.S. Appl. No. 63/088,511, filed Oct. 7, 2020.
U.S. Appl. No. 63/088,539, filed Oct. 7, 2020.
U.S. Appl. No. 63/094,464, filed Oct. 21, 2020.
U.S. Appl. No. 63/094,498, filed Oct. 21, 2020.
U.S. Appl. No. 63/094,594, filed Oct. 21, 2020.
U.S. Appl. No. 63/094,608, filed Oct. 21, 2020.
U.S. Appl. No. 63/094,626, filed Oct. 21, 2020.
U.S. Appl. No. 63/094,646, filed Oct. 21, 2020.
U.S. Appl. No. 63/109,066, filed Nov. 3, 2020.
U.S. Appl. No. 63/109,084, filed Nov. 3, 2020.
U.S. Appl. No. 63/112,417, filed Nov. 11, 2020.
U.S. Appl. No. 63/119,161, filed Nov. 30, 2020.
U.S. Appl. No. 63/124,271, filed Dec. 11, 2020.
U.S. Appl. No. 63/133,892, filed Jan. 5, 2021.
U.S. Appl. No. 63/134,287, filed Jan. 6, 2021.
U.S. Appl. No. 63/134,450, filed Jan. 6, 2021.
U.S. Appl. No. 63/134,631, filed Jan. 7, 2021.
U.S. Appl. No. 63/134,632, filed Jan. 7, 2021.
U.S. Appl. No. 63/134,754, filed Jan. 7, 2021.
U.S. Appl. No. 63/138,878, filed Jan. 19, 2021.
U.S. Appl. No. 63/146,946, filed Feb. 8, 2021.
U.S. Appl. No. 63/147,013, filed Feb. 8, 2021.
U.S. Appl. No. 63/147,299, filed Feb. 9, 2021.
U.S. Appl. No. 63/148,723, filed Feb. 12, 2021.
U.S. Appl. No. 63/154,248, filed Feb. 26, 2021.
U.S. Appl. No. 63/155,395, filed Mar. 2, 2021.

(56) References Cited

OTHER PUBLICATIONS

U.S. Appl. No. 63/157,007, filed Mar. 5, 2021.
U.S. Appl. No. 63/157,014, filed Mar. 5, 2021.
U.S. Appl. No. 63/159,142, filed Mar. 10, 2021.
U.S. Appl. No. 63/159,186, filed Mar. 10, 2021.
U.S. Appl. No. 63/159,210, filed Mar. 10, 2021.
U.S. Appl. No. 63/159,280, filed Mar. 10, 2021.
U.S. Appl. No. 63/165,273 filed Mar. 24, 2021.
U.S. Appl. No. 63/165,384, filed Mar. 24, 2021.
U.S. Appl. No. 63/171,165, filed Apr. 6, 2021.
U.S. Appl. No. 63/172,975, filed Apr. 9, 2021.
U.S. Appl. No. 63/181,695, filed Apr. 29, 2021.
U.S. Appl. No. 63/192,274, filed May 24, 2021.
U.S. Appl. No. 63/192,289, filed May 24, 2021.
U.S. Appl. No. 63/193,235, filed May 26, 2021.
U.S. Appl. No. 63/193,406, filed May 26, 2021.
U.S. Appl. No. 63/193,891, filed May 27, 2021.
U.S. Appl. No. 63/208,262, filed Jun. 8, 2021.
U.S. Appl. No. 63/214,551, filed Jun. 24, 2021.
U.S. Appl. No. 63/214,570, filed Jun. 24, 2021.
U.S. Appl. No. 63/215,017, filed Jun. 25, 2021.
U.S. Appl. No. 63/228,244, filed Aug. 2, 2021.
U.S. Appl. No. 63/228,252, filed Aug. 2, 2021.
U.S. Appl. No. 63/228,258, filed Aug. 2, 2021.
U.S. Appl. No. 63/230,894, filed Aug. 9, 2021.
U.S. Appl. No. 63/230,897, filed Aug. 9, 2021.
U.S. Appl. No. 63/238,457, filed Aug. 30, 2021.
U.S. Appl. No. 63/238,477, filed Aug. 30, 2021.
U.S. Appl. No. 63/241,562, filed Sep. 8, 2021.
U.S. Appl. No. 63/241,564, filed Sep. 8, 2021.
U.S. Appl. No. 63/241,575, filed Sep. 8, 2021.
U.S. Appl. No. 63/246,972, filed Sep. 22, 2021.
U.S. Appl. No. 63/247,375, filed Sep. 23, 2021.
U.S. Appl. No. 63/247,478, filed Sep. 23, 2021.
U.S. Appl. No. 63/247,491, filed Sep. 23, 2021.
U.S. Appl. No. 63/299,208, filed Jan. 13, 2022.
Sage's Second Supplemental Invalidity Contentions Regarding U.S. Pat. Nos. 8,287,508, 10,226,375, 10,390,989, and 10,376,407, 292 pages.
Plaintiff's Identification of Claim Terms and Proposed Constructions, 3 pages.
Sage's Preliminary Identification of Claim Elements and Proposed Constructions for U.S. Pat. Nos. 8,287,508, 10,226,376, 10,390,989 and 10,376,407, 7 pages.
Corrected Certificate of Service, 2020, 2 pages.
Excerpts from the 508 (U.S. Pat. No. 8,278,508) Patent's Prosecution History, 2020, 99 pages.
Declaration of Diane K. Newman Curriculum Vitae, 2020, pp. 1-199.
Sage's Supplemental and Initial Invalidity Contentions Regarding U.S. Pat. Nos. 8,287,508; 10,226,375; 10,390,989 and Initial Invalidity Contentions Regarding U.S. Pat. No. 10,376,407, Aug. 21, 2020, 277 pages.
Decision Granting Institution of Inter Partes Review for U.S. Pat. No. 8,287,508, Feb. 17, 2021, 39 pages.
Memorandum Order, Feb. 2021, 14 pgs.
Boehringer CareDry System—Second Generation for Non-Invasive Urinary Management for Females, Mar. 2021, 3 pgs.
PureWick's Response to Interrogatory No. 9 in *PureWick, LLC* v. *Sage Products, LLC*, Mar. 23, 2020, 6 pages.
Sage's Initial Invalidity Contentions Regarding U.S. Pat. Nos. 8,287,508; 10,226,375; and 10,390,989, May 29, 2020, 193 pages.
Defendant and Counterclaim Plaintiff Sage Products, LLC's Answer, Defenses, and Counterclaims to Plaintiff's Amended Complaint, Nov. 1, 2019.
Plaintiff's Opening Claim Construction Brief, Oct. 16, 2020, 26 pages.
"3 Devices Take Top Honors in Dare-To-Dream Medtech Design Contest", R+D Digest, Nov. 2013, 1 page.
"Advanced Mission Extender Device (AMDX) Products", Omni Medical Systems, Inc., 15 pages.
"AMXD Control Starter Kit Brochure", https://www.omnimedicalsys.com/index.php?page=products, 8 pages.
"AMXDmax In-Flight Bladder Relief", Omni Medical; Omni Medical Systems, Inc., 2015.
"AMXDX—Advanced Mission Extender Device Brochure", Omni Medical, 2 pages.
"External Urine Management for Female Anatomy", https://www.stryker.com/us/en/sage/products/sage-primafit.html, Jul. 2020, 4 pages.
"High Absorbancy Cellulose Acetate Electrospun Nanofibers for Feminine Hygiene Application", https://www.sciencedirect.com/science/article/abs/pii/S2352940716300701?via%3Dihub, Jul. 2016, 3 pages.
"How Period Panties Work", www.shethinx.com/pages/thinx-itworks, 2020, 10 pages.
"Hydrogel properties of electrospun polyvinylpyrrolidone and polyvinylpyrrolidone/poly(acrylic acid) blend nanofibers", https://pubs.rsc.org/en/content/articlelanding/2015/ra/c5ra07514a#!divAbstract, 2015, 5 pages.
"In Flight Bladder Relief", Omni Medical, 14 pages.
"Making Women's Sanitary Products Safer and Cheaper", https://www.elsevier.com/connect/making-womens-sanitary-products-safer-and-cheaper, Sep. 2016, 10 pages.
"Novel Nanofibers Make Safe and Effective Absorbent for Sanitary Products", https://www.materialstoday.com/nanomaterials/news/nanofibers-make-safe-and-effective-absorbent/, Oct. 2016, 3 pages.
"Research and Development Work Relating to Assistive Technology 2005-06", British Department of Health, Nov. 2006, 40 pages.
"Rising Warrior Insulated Gallon Jug Cover", https://www.amazon.com/Rising-Warrior-Insulated-Sleeve, 2021, 2 pages.
"Step by Step How Ur24 WorksHome", http://medicalpatentur24.com, Aug 30, 2017, 4 pages.
"Underwear that absorbs your period", Thinx!, 7 pages.
"Urine Bag Cover-Catheter Bag Cover 2000 ml Volume-Medline Style-Multiple Sclerosis-Spine Injury-Suprapublic Catheter-Bladder Incontinence", https://www.etsy.com/listing/1142934658/urine-bag-cover-caatheter-bag-cover-2000, 2022, 1 page.
"User & Maintenance Guide", Omni Medical, 2007, 16 pages.
"Vinyl Dust Cover, Janome #741811000, Janome, Sewing Parts Online", https://www.sewingpartsonline.com/vinyl-dust-cover-janome-74181000, 2020, 2 pages.
"Winners Announced for Dare-to-Dream Medtech Design Challenge", https://www.mddionline.com/design-engineering/winners-announced-dare-dream-medtech-design-challenge, 2014, 4 pages.
Ali , "Sustainability Assessment: Seventh Generation Diapers versus gDiapers", The University of Vermont, Dec. 6, 2011, pp. 1-31.
Autumn , et al., "Frictional adhesion: a new angle on gecko attachment", The Journal of Experimental Biology, 2006, pp. 3569-3579.
Cañas , et al., "Effect of nano- and micro-roughness on adhesion of bioinspired micropatterned surfaces", Acta Biomaterialia 8, 2012, pp. 282-288.
Chaudhary , et al., "Bioinspired dry adhesive: Poly(dimethylsiloxane) grafted with poly(2-ethylhexyl acrylate) brushes", European Polymer Journal, 2015, pp. 432-440.
Dai , et al., "Non-sticky and Non-slippery Biomimetic Patterned Surfaces", Journal of Bionic Engineering, Mar. 2020, pp. 326-334.
Espinoza-Ramirez , "Nanobiodiversity and Biomimetic Adhesives Development: From Nature to Production and Application", Journal of Biomaterials and Nanobiotechnology, pp. 78-101, 2019.
Hollister , "Female Urinary and Pouch and Male Urinary Pouch Brochure", 2011, 1 page.
Hollister , "Male Urinary Pouch External Collection Device", http://www.hollister.com/en/products/Continence-Care-Products/Urine-Collectors/Urine-Collection-Accessories/Male-Urinary-Pouch-External-Collection-Device.
Hollister , "Retracted Penis Pouch by Hollister", Vitality Medical.com, 6 pages.
Hwang , et al., "Multifunctional Smart Skin Adhesive Patches for Advanced Health Care", Adv. Healthcare Mater, 2018, pp. 1-20.

(56) References Cited

OTHER PUBLICATIONS

Jagota, et al., "Adhesion, friction, and compliance of bio-mimetic and bio-inspired structured interfaces", Materials Science and Engineering, 2011, pp. 253-292.
Jeong, et al., "A nontransferring dry adhesive with hierarchical polymer nanohairs", PNAS, Apr. 7, 2009, pp. 5639-5644.
Jeong, et al., "Nanohairs and nanotubes: Efficient structural elements for gecko-inspired artificial dry adhesives", Science Direct, 2009, pp. 335-346.
Karp, et al., "Dry solution to a sticky problem", Nature., 2011, pp. 42-43.
Lee, et al., "Continuous Fabrication of Wide-Tip Microstructures for Bio-Inspired Dry Adhesives via Tip Inking Process", Journal of Chemistry, Jan. 2, 2019, pp. 1-5.
Macaulay, et al., "A Noninvasive Continence Management System: Development and Evaluation of a Novel Toileting Device for Women", The Wound, Ostomy and Continence Nurses Society, 2007, pp. 641-648.
Newman, et al., "The Urinary Incontinence Sourcebook", Petition for Interparties Review, 1997, 23 pages.
Newton, et al., "Measuring Safety, Effectiveness and Ease of Use of PureWick in the Management of Urinary Incontinence in Bedbound Women: Case Studies", Jan. 8, 2016, 11 pages.
Parmar, "10 Finalists Chosen for Dare-to-Dream Medtech Design Challenge (PureWick)", Design Services, Nov. 10, 2014, 3 pages.
Parness, et al. "A microfabricated wedge-shaped adhesive array displaying gecko-like dynamic adhesion, directionality", J.R. Soc. Interface, 2009, pp. 1223-1232.
Purewick, "Incontinence Relief for Women", Presentation, Sep. 23, 2015, 7 pages.
Pytlik, "Super Absorbent Polymers", University of Buffalo.
Sachtman, "New Relief for Pilots? It Depends", Wired, 2008, 2 pages.
Tsipenyuk, et al., "Use of biomimetic hexagonal surface texture in friction against lubricated skin", Journal of the Royal Society—Interface, 2014, pp. 1-6.
Advisory Action for U.S. Appl. No. 16/904,868 dated Jun. 15, 2022.
Final Office Action for U.S. Appl. No. 16/449,039 dated Aug. 1, 2022.
Final Office Action for U.S. Appl. No. 16/452,258 dated Jun. 14, 2022.
Final Office Action for U.S. Appl. No. 16/478,180 dated Jun. 22, 2022.
International Search Report and Written Opinion from International Application No. PCT/US2021/039866 dated Oct. 7, 2021.
International Search Report and Written Opinion from International Application No. PCT/US2021/051456 dated Jan. 19, 2022.
International Search Report and Written Opinion from International Application No. PCT/US2021/055515 dated Jan. 28, 2022.
International Search Report and Written Opinion from International Application No. PCT/US2022/011419 dated Jun. 7, 2022.
International Search Report and Written Opinion from International Application No. PCT/US2022/011421 dated Jun. 13, 2022.
International Search Report and Written Opinion from International Application No. PCT/US2022/012794 dated May 3, 2022.
International Search Report and Written Opinion from International Application No. PCT/US2022/015471 dated May 16, 2022.
International Search Report and Written Opinion from International Application No. PCT/US2022/015492 dated Apr. 26, 2022.
International Search Report and Written Opinion from International Application No. PCT/US2022/016942 dated Jun. 3, 2022.
International Search Report and Written Opinion from International Application No. PCT/US2022/018170 dated May 31, 2022.
International Search Report and Written Opinion from International Application No. PCT/US2022/019254 dated Jun. 7, 2022.
International Search Report and Written Opinion from International Application No. PCT/US2022/019480 dated Jun. 13, 2022.
International Search Report and Written Opinion from International Application No. PCT/US2022/021103 dated Jun. 23, 2022.
Issue Notification for U.S. Appl. No. 17/088,272 dated Jun. 15, 2022.
Issue Notification for U.S. Appl. No. 17/330,657 dated Jun. 22, 2022.
Notice of Allowance for U.S. Appl. No. 16/899,956 dated Aug. 10, 2022.
Notice of Allowance for U.S. Appl. No. 16/905,400 dated Aug. 17, 2022.
Notice of Allowance for U.S. Appl. No. 29/741,751 dated Jun. 9, 2022.
U.S. Appl. No. 17/663,046, filed May 12, 2022.
U.S. Appl. No. 17/664,914, filed May 25, 2022.
U.S. Appl. No. 17/749,340, filed May 20, 2022.
U.S. Appl. No. 17/756,201, filed May 19, 2022.
U.S. Appl. No. 17/758,152, filed Jun. 29, 2022.
U.S. Appl. No. 17/758,316, filed Jul. 1, 2022.
U.S. Appl. No. 17/759,697, filed Jul. 28, 2022.
U.S. Appl. No. 17/878,268, filed Aug. 1, 2022.
U.S. Appl. No. 17/929,887, filed Sep. 6, 2022.
U.S. Appl. No. 17/930,238, filed Sep. 7, 2022.
U.S. Appl. No. 62/967,158, filed Jan. 26, 2020.
U.S. Appl. No. 63/191,558, filed May 21, 2021.
U.S. Appl. No. 63/241,328, filed Sep. 7, 2021.
Advisory Action for U.S. Appl. No. 16/433,773 dated Feb. 15, 2023.
Advisory Action for U.S. Appl. No. 16/452,258 dated Oct. 26, 2022.
Advisory Action for U.S. Appl. No. 16/478,180 dated Sep. 21, 2022.
Final Office Action for U.S. Appl. No. 16/245,726 dated Nov. 25, 2022.
Final Office Action for U.S. Appl. No. 16/369,676 dated Dec. 5, 2022.
Final Office Action for U.S. Appl. No. 16/433,773 dated Oct. 25, 2022.
International Search Report and Written Opinion from International Application No. PCT/IB2021/057173 dated Nov. 5, 2021.
International Search Report and Written Opinion from International Application No. PCT/US2022/014285 dated Sep. 28, 2022.
International Search Report and Written Opinion from International Application No. PCT/US2022/014749 dated Sep. 28, 2022.
International Search Report and Written Opinion from International Application No. PCT/US2022/015026 dated Oct. 31, 2022.
International Search Report and Written Opinion from International Application No. PCT/US2022/015045 dated Sep. 9, 2022.
International Search Report and Written Opinion from International Application No. PCT/US2022/015073 dated Sep. 8, 2022.
International Search Report and Written Opinion from International Application No. PCT/US2022/015418 dated Nov. 11, 2022.
International Search Report and Written Opinion from International Application No. PCT/US2022/015420 dated Nov. 18, 2022.
International Search Report and Written Opinion from International Application No. PCT/US2022/015781 dated May 6, 2022.
International Search Report and Written Opinion from International Application No. PCT/US2022/018159 dated Dec. 12, 2022.
International Search Report and Written Opinion from International Application No. PCT/US2022/022111 dated Oct. 26, 2022.
International Search Report and Written Opinion from International Application No. PCT/US2022/023594 dated Jul. 12, 2022.
International Search Report and Written Opinion from International Application No. PCT/US2022/026667 dated Aug. 22, 2022.
International Search Report and Written Opinion from International Application No. PCT/US2022/030685 dated Oct. 31, 2022.
International Search Report and Written Opinion from International Application No. PCT/US2022/031032 dated Sep. 9, 2022.
International Search Report and Written Opinion from International Application No. PCT/US2022/032424 dated Oct. 11, 2022.
International Search Report and Written Opinion from International Application No. PCT/US2022/034457 dated Oct. 12, 2022.
International Search Report and Written Opinion from International Application No. PCT/US2022/034744 dated Dec. 9, 2022.
International Search Report and Written Opinion from International Application No. PCT/US2022/039022 dated Jan. 10, 2023.
International Search Report and Written Opinion from International Application No. PCT/US2022/039711 dated Jan. 12, 2023.

(56) References Cited

OTHER PUBLICATIONS

International Search Report and Written Opinion from International Application No. PCT/US2022/039714 dated Nov. 22, 2022.
International Search Report and Written Opinion from International Application No. PCT/US2022/042719 dated Dec. 5, 2022.
International Search Report and Written Opinion from International Application No. PCT/US2022/042725 dated Dec. 19, 2022.
International Search Report and Written Opinion from International Application No. PCT/US2022/044107 dated Dec. 23, 2022.
Issue Notification for U.S. Appl. No. 16,905,400 dated Nov. 30, 2022.
Non-Final Office Action for U.S. Appl. No. 16/478,180 dated Dec. 20, 2022.
Non-Final Office Action for U.S. Appl. No. 17/051,550 dated Dec. 15, 2022.
Non-Final Office Action for U.S. Appl. No. 17/451,345 dated Dec. 7, 2022.
Notice of Allowance for U.S. Appl. No. 16/449,039 dated Dec. 15, 2022.
Notice of Allowance for U.S. Appl. No. 16/899,956 dated Dec. 1, 2022.
Notice of Allowance for U.S. Appl. No. 17/461,036 dated Feb. 22, 2023.
Notice of Allowance for U.S. Appl. No. 17/461,036 dated Oct. 6, 2022.
Notice of Allowance for U.S. Appl. No. 17/663,046 dated Jan. 30, 2023.
U.S. Appl. No. 17/907,125, filed Sep. 23, 2022.
U.S. Appl. No. 17/912,147, filed Sep. 16, 2022.
U.S. Appl. No. 17/933,590, filed Sep. 20, 2022.
U.S. Appl. No. 17/996,064, filed Oct. 12, 2022.
U.S. Appl. No. 17/996,155, filed Oct. 13, 2022.
U.S. Appl. No. 17/996,253, filed Oct. 14, 2022.
U.S. Appl. No. 17/996,468, filed Oct. 18, 2022.
U.S. Appl. No. 17/996,556, filed Oct. 19, 2022.
U.S. Appl. No. 18/003,029, filed Dec. 22, 2022.
U.S. Appl. No. 18/006,807, filed Jan. 25, 2023.
U.S. Appl. No. 18/007,105, filed Jan. 27, 2023.
U.S. Appl. No. 18/041,109, filed Feb. 9, 2023.
U.S. Appl. No. 18/042,842, filed Feb. 24, 2023.
U.S. Appl. No. 18/164,800, filed Feb. 6, 2023.
U.S. Appl. No. 62/991,754, filed Mar. 19, 2020.
Advisory Action for U.S. Appl. No. 16/245,726 mailed Apr. 19, 2023.
Advisory Action for U.S. Appl. No. 16/369,676 mailed Mar. 24, 2023.
Final Office Action for U.S. Appl. No. 16/478,180 mailed May 31, 2023.
Final Office Action for U.S. Appl. No. 17/051,399 mailed Mar. 9, 2023.
Final Office Action for U.S. Appl. No. 17/051,550 mailed May 23, 2023.
Final Office Action for U.S. Appl. No. 17/451,345 mailed May 3, 2023.
International Search Report and Written Opinion from International Application No. PCT/US2022/039018 mailed Jan. 10, 2023.
International Search Report and Written Opinion from International Application No. PCT/US2022/041085 mailed Mar. 16, 2023.
International Search Report and Written Opinion from International Application No. PCT/US2022/041688 mailed Nov. 21, 2022.
International Search Report and Written Opinion from International Application No. PCT/US2022/043818 mailed Mar. 24, 2023.
International Search Report and Written Opinion from International Application No. PCT/US2022/044208 mailed May 8, 2023.
International Search Report and Written Opinion from International Application No. PCT/US2022/044212 mailed Jan. 20, 2023.
International Search Report and Written Opinion from International Application No. PCT/US2022/044243 mailed Feb. 24, 2023.
International Search Report and Written Opinion from International Application No. PCT/US2022/049300 mailed Jun. 6, 2023.
Issue Notification for U.S. Appl. No. 16/899,956 mailed Mar. 29, 2023.
Non-Final Office Action for U.S. Appl. No. 16/433,773 mailed Apr. 11, 2023.
Non-Final Office Action for U.S. Appl. No. 16/449,039 mailed Apr. 27, 2023.
Non-Final Office Action for U.S. Appl. No. 16/452,145 mailed Mar. 28, 2023.
Non-Final Office Action for U.S. Appl. No. 17/653,137 mailed Apr. 7, 2023.
Non-Final Office Action for U.S. Appl. No. 17/655,464 mailed Mar. 14, 2023.
Non-Final Office Action for U.S. Appl. No. 17/664,487 mailed Jun. 8, 2023.
Restriction Requirement for U.S. Appl. No. 17/326,980 mailed Mar. 20, 2023.
Restriction Requirement for U.S. Appl. No. 17/446,256 mailed Jan. 23, 2023.
Restriction Requirement for U.S. Appl. No. 17/646,771 mailed Apr. 6, 2023.
Text Messages to Lorena Eckert Re Prototype PureWick Holder dated Apr. 16, 2022.
U.S. Appl. No. 17/664,487, filed May 23, 2022.
U.S. Appl. No. 18/043,618, filed Mar. 1, 2023.
U.S. Appl. No. 18/115,444, filed Feb. 28, 2023.
U.S. Appl. No. 18/134,857, filed Apr. 14, 2023.
Non-Final Office Action for U.S. Appl. No. 16/452,258 mailed Apr. 26, 2023.
Non-Final Office Action for U.S. Appl. No. 16/904,868 mailed Mar. 15, 2023.
Non-Final Office Action for U.S. Appl. No. 17/051,585 mailed Mar. 29, 2023.
Non-Final Office Action for U.S. Appl. No. 17/179,116 mailed Mar. 24, 2023.
Non-Final Office Action for U.S. Appl. No. 17/444,792 mailed Feb. 10, 2023.
Non-Final Office Action for U.S. Appl. No. 17/446,256 mailed Apr. 13, 2023.
Non-Final Office Action for U.S. Appl. No. 17/448,811 mailed Mar. 1, 2023.
Non-Final Office Action for U.S. Appl. No. 17/450,864 mailed May 10, 2023.
Non-Final Office Action for U.S. Appl. No. 17/451,354 mailed May 3, 2023.
Non-Final Office Action for U.S. Appl. No. 17/453,260 mailed Mar. 14, 2023.
Non-Final Office Action for U.S. Appl. No. 17/501,591 mailed Apr. 25, 2023.
U.S. Appl. No. 18/140,163, filed Apr. 27, 2023.
U.S. Appl. No. 18/140,751, filed Apr. 28, 2023.
U.S. Appl. No. 18/198,464, filed May 17, 2023.
U.S. Appl. No. 18/246,121, filed Mar. 21, 2023.
U.S. Appl. No. 18/247,986, filed Apr. 5, 2023.
U.S. Appl. No. 18/265,736, filed Jun. 7, 2023.
U.S. Appl. No. 18/299,788, filed Apr. 13, 2023.
U.S. Appl. No. 18/335,579, filed Jun. 15, 2023.
U.S. Appl. No. 63/308,190, filed Feb. 9, 2022.
*PureWick Corporation* v. *Sage Products, LLC* Transcripts vol. 5, Apr. 1, 2022, 72 pages.
*PureWick Corporation* v. *Sage Products, LLC* Transcripts vol. 1, Mar. 28, 2022, 99 pages.
*PureWick Corporation* v. *Sage Products, LLC* Transcripts vol. 2, Mar. 29, 2022, 106 pages.
*PureWick Corporation* v. *Sage Products, LLC* Transcripts vol. 3, Mar. 30, 2022, 115 pages.
*PureWick Corporation* v. *Sage Products, LLC* Transcripts vol. 4, Mar. 31, 2022, 117 pages.
"AMXD Control Starter Kit", Omni Medical Systems, Inc., 1 page.
"AMXDmax Advanced Mission Extender Device User & Maintenance Guide", Omni Medical, Jan. 11, 2010, 10 pages.
"AMXDmax Development History 2002-2014", Omni Medical Systems, Inc., 2 pages.

(56) References Cited

OTHER PUBLICATIONS

"Combat Force Multiplier in Flight Bladder Relief Cockpit Essential Equipment Brochure", Omni Medical, 20 pages.
"GSA Price List", Omni Medical, Apr. 2011, 2 pages.
"How is Polypropylene Fiber Made", https:www.yarnsandfibers.com/textile-resources/synthetic-fibers/polypropylene-fiber/polypropylene-fiber-production-raw-materials/how-is-polypropylene-fiber-made/ last accessed 2020, Oct. 7, 2020, 3 pages.
"Letter to Mark Harvie of Omni Measurement Systems", Department of Veterans Affairs, Nov. 1, 2007, 11 pages.
"Revised AMXDmax Advanced Mission Extender Device User & Maintenance Guide", Omni Medical Systems, Oct. 8, 2019, 52 pages.
Pieper, et al., "An external urine-collection device for women: A clinical trial", Journal of ER Nursing, vol. 20, No. 2, Mar./Apr. 1993, pp. 51-55.
VINAS, "A Solution For An Awkward—But Serious—Subject", http://www.aero-news.net/index.cfm?do=main.textpost&id=69ae2bb1-838b-4098-a7b5-7flbb2505688 last accessed Feb. 8, 2021, 3 pages.
Advisory Action for U.S. Appl. No. 16/478,180 mailed Sep. 7, 2023.
Advisory Action for U.S. Appl. No. 17/051,550 mailed Sep. 8, 2023.
Advisory Action for U.S. Appl. No. 17/051,585 mailed Oct. 17, 2023.
Advisory Action for U.S. Appl. No. 17/444,792 mailed Aug. 25, 2023.
Advisory Action for U.S. Appl. No. 17/451,345 mailed Oct. 20, 2023.
Final Office Action for U.S. Appl. No. 16/369,676 mailed Aug. 31, 2023.
Final Office Action for U.S. Appl. No. 16/433,773 mailed Oct. 10, 2023.
Final Office Action for U.S. Appl. No. 17/051,585 mailed Jul. 27, 2023.
Final Office Action for U.S. Appl. No. 17/444,792 mailed Jun. 15, 2023.
Final Office Action for U.S. Appl. No. 17/446,256 mailed Sep. 19, 2023.
Final Office Action for U.S. Appl. No. 17/448,811 mailed Aug. 3, 2023.
Final Office Action for U.S. Appl. No. 17/453,260 mailed Oct. 5, 2023.
Final Office Action for U.S. Appl. No. 17/653,137 mailed Sep. 21, 2023.
Final Office Action for U.S. Appl. No. 17/655,464 mailed Sep. 1, 2023.
International Search Report and Written Opinion from International Application No. PCT/US2022/050909 mailed Jul. 24, 2023.
International Search Report and Written Opinion from International Application No. PCT/US2023/012696 mailed Jul. 6, 2023.
International Search Report and Written Opinion from International Application No. PCT/US2023/018474 mailed Sep. 11, 2023.
Issue Notification for U.S. Appl. No. 16/245,726 mailed Oct. 18, 2023.
Issue Notification for U.S. Appl. No. 17/461,036 mailed Oct. 11, 2023.
Non-Final Office Action for U.S. Appl. No. 17/051,399 mailed Aug. 18, 2023.
Non-Final Office Action for U.S. Appl. No. 17/326,980 mailed Jul. 11, 2023.
Non-Final Office Action for U.S. Appl. No. 17/446,654 mailed Sep. 8, 2023.
Non-Final Office Action for U.S. Appl. No. 17/453,560 mailed Oct. 16, 2023.
Non-Final Office Action for U.S. Appl. No. 17/646,771 mailed Jul. 5, 2023.
Non-Final Office Action for U.S. Appl. No. 17/657,474 mailed Sep. 12, 2023.
Non-Final Office Action for U.S. Appl. No. 17/661,090 mailed Jul. 6, 2023.
Non-Final Office Action for U.S. Appl. No. 17/663,330 mailed Jun. 29, 2023.
Non-Final Office Action for U.S. Appl. No. 18/139,523 mailed Aug. 17, 2023.
Non-Final Office Action for U.S. Appl. No. 18/140,751 mailed Sep. 14, 2023.
Notice of Allowance for U.S. Appl. No. 16/245,726 mailed Jul. 6, 2023.
Notice of Allowance for U.S. Appl. No. 17/051,554 mailed Jul. 6, 2023.
Notice of Allowance for U.S. Appl. No. 17/051,554 mailed Oct. 18, 2023.
Notice of Allowance for U.S. Appl. No. 17/461,036 mailed Jun. 30, 2023.
Notice of Allowance for U.S. Appl. No. 18/299,788 mailed Jul. 24, 2023.
Restriction Requirement for U.S. Appl. No. 17/051,600 mailed Sep. 21, 2023.
Restriction Requirement for U.S. Appl. No. 17/645,821 mailed Jul. 12, 2023.
Restriction Requirement for U.S. Appl. No. 17/657,474 mailed Jun. 30, 2023.
U.S. Appl. No. 18/259,626, filed Jun. 28, 2023.
U.S. Appl. No. 18/260,122, filed Jun. 30, 2023.
U.S. Appl. No. 18/260,391, filed Jul. 5, 2023.
U.S. Appl. No. 18/260,394, filed Jul. 5, 2023.
U.S. Appl. No. 18/263,800, filed Aug. 1, 2023.
U.S. Appl. No. 18/264,004, filed Aug. 2, 2023.
U.S. Appl. No. 18/373,424, filed Sep. 27, 2023.
U.S. Appl. No. 18/376,274, filed Oct. 3, 2023.
U.S. Appl. No. 18/548,152, filed Aug. 28, 2023.
U.S. Appl. No. 18/549,387, filed Sep. 7, 2023.
U.S. Appl. No. 18/549,658, filed Sep. 8, 2023.
U.S. Appl. No. 18/553,625, filed Oct. 2, 2023.
U.S. Appl. No. 63/150,640, filed Feb. 18, 2021.
Merriam-Webster Dictionary, "Embed Definition & Meaning", https://www.merriam-webster.com/dictionary/embed last accessed Aug. 3, 2023, 2003.
Advisory Action for U.S. Appl. No. 16/433,773 mailed Dec. 29, 2023.
Advisory Action for U.S. Appl. No. 16/449,039 mailed Jan. 25, 2024.
Advisory Action for U.S. Appl. No. 16/904,868 mailed Jan. 2, 2024.
Advisory Action for U.S. Appl. No. 17/179,116 mailed Jan. 8, 2024.
Advisory Action for U.S. Appl. No. 17/446,256 mailed Dec. 8, 2023.
Advisory Action for U.S. Appl. No. 17/448,811 mailed Nov. 15, 2023.
Advisory Action for U.S. Appl. No. 17/451,354 mailed Jan. 30, 2024.
Advisory Action for U.S. Appl. No. 17/453,260 mailed Dec. 22, 2023.
Advisory Action for U.S. Appl. No. 17/653,137 mailed Dec. 1, 2023.
Advisory Action for U.S. Appl. No. 17/655,464 mailed Dec. 13, 2023.
Advisory Action for U.S. Appl. No. 18/164,800 mailed Feb. 12, 2024.
Communication of Notice of Opposition of European Application No. 17807547.9 mailed Jan. 5, 2024.
Corrected Notice of Allowability for U.S. Appl. No. 16/369,676 mailed Dec. 7, 2023.
Corrected Notice of Allowability for U.S. Appl. No. 17/326,980 mailed Feb. 8, 2024.
Final Office Action for U.S. Appl. No. 16/449,039 mailed Nov. 21, 2023.
Final Office Action for U.S. Appl. No. 16/452,258 mailed Dec. 21, 2023.
Final Office Action for U.S. Appl. No. 16/904,868 mailed Nov. 2, 2023.
Final Office Action for U.S. Appl. No. 17/051,399 mailed Jan. 8, 2024.

(56) References Cited

OTHER PUBLICATIONS

Final Office Action for U.S. Appl. No. 17/179,116 mailed Oct. 31, 2023.
Final Office Action for U.S. Appl. No. 17/446,654 mailed Jan. 31, 2024.
Final Office Action for U.S. Appl. No. 17/450,864 mailed Dec. 28, 2023.
Final Office Action for U.S. Appl. No. 17/451,354 mailed Oct. 30, 2023.
Final Office Action for U.S. Appl. No. 17/501,591 mailed Nov. 14, 2023.
Final Office Action for U.S. Appl. No. 17/646,771 mailed Dec. 21, 2023.
Final Office Action for U.S. Appl. No. 17/661,090 mailed Dec. 11, 2023.
Final Office Action for U.S. Appl. No. 17/663,330 mailed Dec. 12, 2023.
Final Office Action for U.S. Appl. No. 17/664,487 mailed Jan. 4, 2024.
Final Office Action for U.S. Appl. No. 18/139,523 mailed Dec. 22, 2023.
Final Office Action for U.S. Appl. No. 18/140,751 mailed Jan. 17, 2024.
Final Office Action for U.S. Appl. No. 18/164,800 mailed Dec. 6, 2023.
International Search Report and Written Opinion from International Application No. PCT/US2023/024805 mailed Dec. 14, 2023.
Issue Notification for U.S. Appl. No. 17/663,046 mailed Dec. 20, 2023.
Non-Final Office Action for U.S. Appl. No. 16/452,145 mailed Nov. 2, 2023.
Non-Final Office Action for U.S. Appl. No. 16/478,180 mailed Nov. 7, 2023.
Non-Final Office Action for U.S. Appl. No. 17/051,550 mailed Oct. 24, 2023.
Non-Final Office Action for U.S. Appl. No. 17/051,585 mailed Jan. 8, 2024.
Non-Final Office Action for U.S. Appl. No. 17/051,600 mailed Jan. 17, 2024.
Non-Final Office Action for U.S. Appl. No. 17/444,792 mailed Nov. 17, 2023.
Non-Final Office Action for U.S. Appl. No. 17/446,256 mailed Feb. 13, 2024.
Non-Final Office Action for U.S. Appl. No. 17/447,123 mailed Jan. 24, 2024.
Non-Final Office Action for U.S. Appl. No. 17/448,811 mailed Jan. 17, 2024.
Non-Final Office Action for U.S. Appl. No. 17/451,345 mailed Jan. 17, 2024.
Non-Final Office Action for U.S. Appl. No. 17/645,821 mailed Oct. 25, 2023.
Non-Final Office Action for U.S. Appl. No. 17/653,137 mailed Jan. 18, 2024.
Non-Final Office Action for U.S. Appl. No. 17/664,914 mailed Jan. 31, 2024.
Non-Final Office Action for U.S. Appl. No. 17/808,354 mailed Nov. 28, 2023.
Non-Final Office Action for U.S. Appl. No. 18/134,857 mailed Jan. 25, 2024.
Non-Final Office Action for U.S. Appl. No. 18/140,163 mailed Nov. 9, 2023.
Non-Final Office Action for U.S. Appl. No. 18/198,464 mailed Dec. 7, 2023.
Notice of Allowance for U.S. Appl. No. 16/369,676 mailed Nov. 14, 2023.
Notice of Allowance for U.S. Appl. No. 17/051,550 mailed Feb. 7, 2024.
Notice of Allowance for U.S. Appl. No. 17/326,980 mailed Jan. 29, 2024.
Notice of Allowance for U.S. Appl. No. 17/453,560 mailed Jan. 31, 2024.
Notice of Allowance for U.S. Appl. No. 18/299,788 mailed Nov. 6, 2023.
Restriction Requirement for U.S. Appl. No. 18/134,857 mailed Oct. 23, 2023.
Submission in Opposition Proceedings for European Application No. 17807547.9 filed Jan. 10, 2024.
U.S. Appl. No. 17/451,719, filed Oct. 19, 2021.
U.S. Appl. No. 18/294,370, filed Feb. 1, 2024.
U.S. Appl. No. 18/294,403, filed Feb. 1, 2024.
U.S. Appl. No. 18/389,009, filed Nov. 13, 2023.
U.S. Appl. No. 18/415,080, filed Jan. 17, 2024.
U.S. Appl. No. 18/426,795, filed Jan. 30, 2024.
U.S. Appl. No. 18/556,945, filed Oct. 24, 2023.
U.S. Appl. No. 18/558,502, filed Nov. 1, 2023.
U.S. Appl. No. 18/562,626, filed Nov. 20, 2023.
U.S. Appl. No. 18/563,672, filed Nov. 22, 2023.
U.S. Appl. No. 18/569,711, filed Dec. 13, 2023.
U.S. Appl. No. 18/569,778, filed Dec. 13, 2023.
U.S. Appl. No. 18/681,987, filed Feb. 7, 2024.
U.S. Appl. No. 18/682,006, filed Feb. 7, 2024.
U.S. Appl. No. 63/596,012, filed Nov. 3, 2023.
U.S. Appl. No. 63/608,553, filed Dec. 11, 2023.
Wikipedia Article, "Zylinder (Geometrie)", https://de.wikipedia.org/w/index.php?title=Zylinder_(Geometrie)&oldid=154862081, version of Jun. 1, 2016 , 7 pages.
Advisory Action for U.S. Appl. No. 16/452,258 mailed Apr. 8, 2024.
Advisory Action for U.S. Appl. No. 17/446,654 mailed Apr. 15, 2024.
Advisory Action for U.S. Appl. No. 17/450,864 mailed Mar. 21, 2024.
Advisory Action for U.S. Appl. No. 17/501,591 mailed Feb. 22, 2024.
Advisory Action for U.S. Appl. No. 17/646,771 mailed Feb. 29, 2024.
Advisory Action for U.S. Appl. No. 17/661,090 mailed Feb. 26, 2024.
Advisory Action for U.S. Appl. No. 17/663,330 mailed Feb. 27, 2024.
Advisory Action for U.S. Appl. No. 17/664,487 mailed Mar. 13, 2024.
Advisory Action for U.S. Appl. No. 18/139,523 mailed Apr. 24, 2024.
Advisory Action for U.S. Appl. No. 18/140,751 mailed Apr. 24, 2024.
Corrected Notice of Allowability for U.S. Appl. No. 17/657,474 mailed Mar. 13, 2024.
Corrected Notice of Allowability for U.S. Appl. No. 17/657,474 mailed May 14, 2024.
Final Office Action for U.S. Appl. No. 16/478,180 mailed Feb. 28, 2024.
Final Office Action for U.S. Appl. No. 17/444,792 mailed Apr. 3, 2024.
Final Office Action for U.S. Appl. No. 17/447,123 mailed May 14, 2024.
Final Office Action for U.S. Appl. No. 17/451,345 mailed Apr. 18, 2024.
Final Office Action for U.S. Appl. No. 17/645,821 mailed Apr. 3, 2024.
Final Office Action for U.S. Appl. No. 17/808,354 mailed Apr. 10, 2024.
Final Office Action for U.S. Appl. No. 18/140,163 mailed Mar. 27, 2024.
International Search Report and Written Opinion from International Application No. PCT/US2023/025192 mailed Feb. 7, 2024.
International Search Report and Written Opinion from International Application No. PCT/US2023/025939 mailed Feb. 7, 2024.
International Search Report and Written Opinion from International Application No. PCT/US2023/030365 mailed Mar. 13, 2024.
International Search Report and Written Opinion from International Application No. PCT/US2023/030373 mailed Mar. 13, 2024.

(56) References Cited

OTHER PUBLICATIONS

International Search Report and Written Opinion from International Application No. PCT/US2023/031433 mailed Mar. 4, 2024.
International Search Report and Written Opinion from International Application No. PCT/US2023/031740 mailed Mar. 4, 2024.
Issue Notification for U.S. Appl. No. 17/051,550 mailed Mar. 13, 2024.
Issue Notification for U.S. Appl. No. 17/051,554 mailed Mar. 6, 2024.
Issue Notification for U.S. Appl. No. 18/299,788 mailed Feb. 21, 2024.
Non-Final Office Action for U.S. Appl. No. 16/369,676 mailed Feb. 29, 2024.
Non-Final Office Action for U.S. Appl. No. 16/433,773 mailed Feb. 26, 2024.
Non-Final Office Action for U.S. Appl. No. 16/904,868 mailed Mar. 12, 2024.
Non-Final Office Action for U.S. Appl. No. 17/179,116 mailed Feb. 26, 2024.
Non-Final Office Action for U.S. Appl. No. 17/451,354 mailed Apr. 4, 2024.
Non-Final Office Action for U.S. Appl. No. 17/597,673 mailed Mar. 20, 2024.
Non-Final Office Action for U.S. Appl. No. 17/646,771 mailed Apr. 24, 2024.
Non-Final Office Action for U.S. Appl. No. 17/653,920 mailed Mar. 15, 2024.
Non-Final Office Action for U.S. Appl. No. 17/655,464 mailed Mar. 26, 2024.
Non-Final Office Action for U.S. Appl. No. 17/661,090 mailed May 22, 2024.
Non-Final Office Action for U.S. Appl. No. 18/003,029 mailed Mar. 26, 2024.
Non-Final Office Action for U.S. Appl. No. 18/164,800 mailed Mar. 22, 2024.
Non-Final Office Action for U.S. Appl. No. 18/389,009 mailed May 24, 2024.
Notice of Allowance for U.S. Appl. No. 16/449,039 mailed Mar. 28, 2024.
Notice of Allowance for U.S. Appl. No. 17/326,980 mailed Apr. 5, 2024.
Notice of Allowance for U.S. Appl. No. 17/453,260 mailed Apr. 8, 2024.
Notice of Allowance for U.S. Appl. No. 17/657,474 mailed Mar. 5, 2024.
Notice of Allowance for U.S. Appl. No. 17/657,474 mailed May 2, 2024.
Notice of Allowance for U.S. Appl. No. 18/198,464 mailed Apr. 17, 2024.
Restriction Requirement for U.S. Appl. No. 17/667,097 mailed Mar. 20, 2024.
Supplemental Notice of Allowance for U.S. Appl. No. 17/051,550 mailed Feb. 21, 2024.
Supplemental Notice of Allowance for U.S. Appl. No. 17/051,554 mailed Feb. 14, 2024.
U.S. Appl. No. 17/444,792, filed Aug. 10, 2021.
U.S. Appl. No. 18/249,577, filed Oct. 19, 2021.
U.S. Appl. No. 18/584,002, filed Feb. 22, 2024.
U.S. Appl. No. 18/610,523, filed Mar. 20, 2024.
U.S. Appl. No. 18/662,216, filed May 13, 2024.
U.S. Appl. No. 18/687,117, filed Feb. 27, 2024.
U.S. Appl. No. 18/688,023, filed Feb. 29, 2024.
U.S. Appl. No. 18/693,638, filed Mar. 20, 2024.
U.S. Appl. No. 18/694,090, filed Mar. 21, 2024.
U.S. Appl. No. 63/561,893, filed Dec. 11, 2023.
Wikipedia Article, "Decibel", https://web.archive.org/web/20200415219171/https://en.wikipedia.org/wiki/Decibel last accessed Mar. 11, 2024, 21 pages.
Wikipedia Article, "Fiberglass", https://web.archive.org/web/20200309194847/https://en.wikipedia.org/wiki/Fiberglass last accessed Mar. 11, 2024.

\* cited by examiner

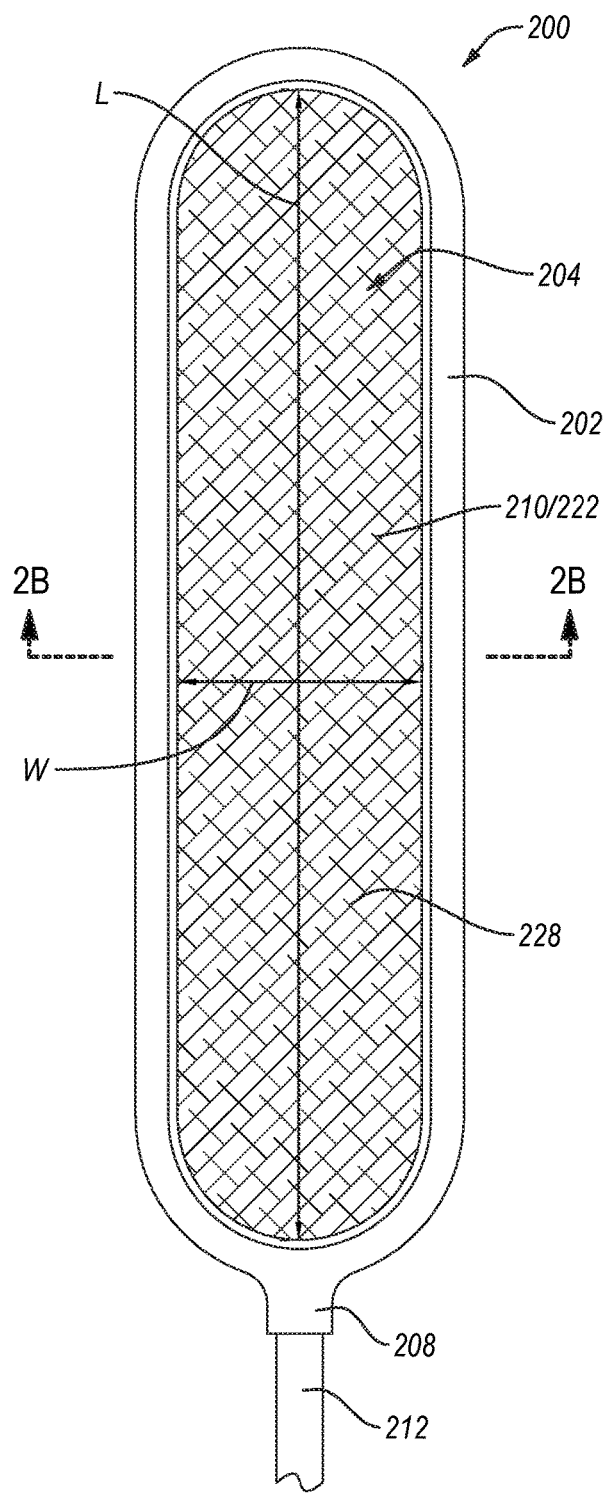
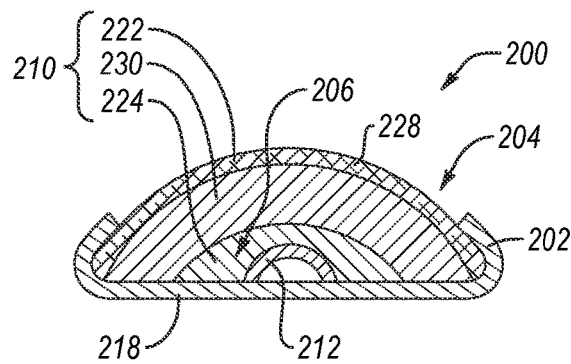
FIG. 2A
FIG. 2B

FLUID COLLECTION ASSEMBLIES INCLUDING ONE OR MORE LEAK PREVENTION FEATURES

CROSS-REFERENCE TO RELATED APPLICATIONS

This application is a continuation of PCT International Application No. PCT/US2021/026607 filed on Apr. 9, 2021, which claims priority to U.S. Provisional Application 63/008,112 filed on Apr. 10, 2020, the disclosure of each of which are incorporated herein, in its entirety, by this reference.

BACKGROUND

A person or animal may have limited or impaired mobility such that typical urination processes are challenging or impossible. For example, a person may experience or have a disability that impairs mobility. A person may have restricted travel conditions such as those experienced by pilots, drivers, and workers in hazardous areas. Additionally, sometimes bodily fluids collection is needed for monitoring purposes or clinical testing.

Urinary catheters, such as a Foley catheter, can be used to address some of these circumstances, such as incontinence. Unfortunately, urinary catheters can be uncomfortable, painful, and can lead to complications, such as infections. Additionally, bed pans, which are receptacles used for the toileting of bedridden patients are sometimes used. However, bedpans can be prone to discomfort, spills, and other hygiene issues.

SUMMARY

In an embodiment, a fluid collection assembly is disclosed. The fluid collection assembly includes a fluid impermeable barrier defining, at least one opening, a chamber in fluid communication with the at least one opening, and at least one fluid outlet. The fluid collection assembly also includes at least one porous material disposed in the chamber. Further, the fluid collection assembly includes at least one conduit attached to the at least one fluid outlet. The fluid collection assembly additionally includes one or more leak prevention features configured to at least inhibit bodily fluids leaking from the chamber Features from any of the disclosed embodiments may be used in combination with one another, without limitation. In addition, other features and advantages of the present disclosure will become apparent to those of ordinary skill in the art through consideration of the following detailed description and the accompanying drawings.

The drawings illustrate several embodiments of the present disclosure, wherein identical reference numerals refer to identical or similar elements or features in different views or embodiments shown in the drawings.

BRIEF DESCRIPTION OF THE DRAWINGS

The drawings illustrate several embodiments of the present disclosure, wherein identical reference numerals refer to identical or similar elements or features in different views or embodiments shown in the drawings.

FIG. 2A is a top plan view of a fluid collection assembly, according to an embodiment.

FIG. 2B is a cross-sectional view of the fluid impermeable barrier taken along ling 2B-2B, according to an embodiment.

DETAILED DESCRIPTION

Embodiments are directed to bodily fluids collection assemblies that include one or more leak prevention features along with systems including and methods of using such bodily fluids collection assemblies. An example fluid collection assembly includes a fluid impermeable barrier defining at least one opening, a chamber in fluid communication with the at least one opening, and at least one fluid outlet. The fluid collection assembly also includes at least one porous material (e.g., at least one wicking material) disposed in the chamber. The fluid collection assembly also includes at least one conduit attached to the fluid outlet. During operation, the fluid collection assembly may receive bodily fluids (e.g., urine) from an individual (e.g., human) through the opening and into the chamber. The porous material may receive at least some of the bodily fluids that enter the chamber. A suction applied from the conduit to the chamber may direct the bodily fluids in chamber towards the conduit. The conduit may then remove the bodily fluids from the chamber.

The fluid collection assembly includes one or more leak prevention features. The leak prevention features decrease the likelihood that the fluid collection assembly leaks compared to a substantially similar fluid collection assembly that does not include the leak prevention features. For example, the bodily fluids may leak from the fluid collection assembly when the bodily fluids flow out of the chamber through the opening or the bodily fluids fail to enter the chamber. The leaked bodily fluids may cause the individual embarrassment and an create unsanitary environment. The bodily fluids may leak from the fluid collection assembly for a variety of reasons, examples of which include movement of the individual, oversaturation of the porous material, and/or the opening of the fluid collection assembly becoming spaced from the individual. The leak prevention features of the fluid collection assembly are configured to minimize or prevent at least some of the reasons that cause the fluid collection assembly to leak.

Figures 1A, 1B:
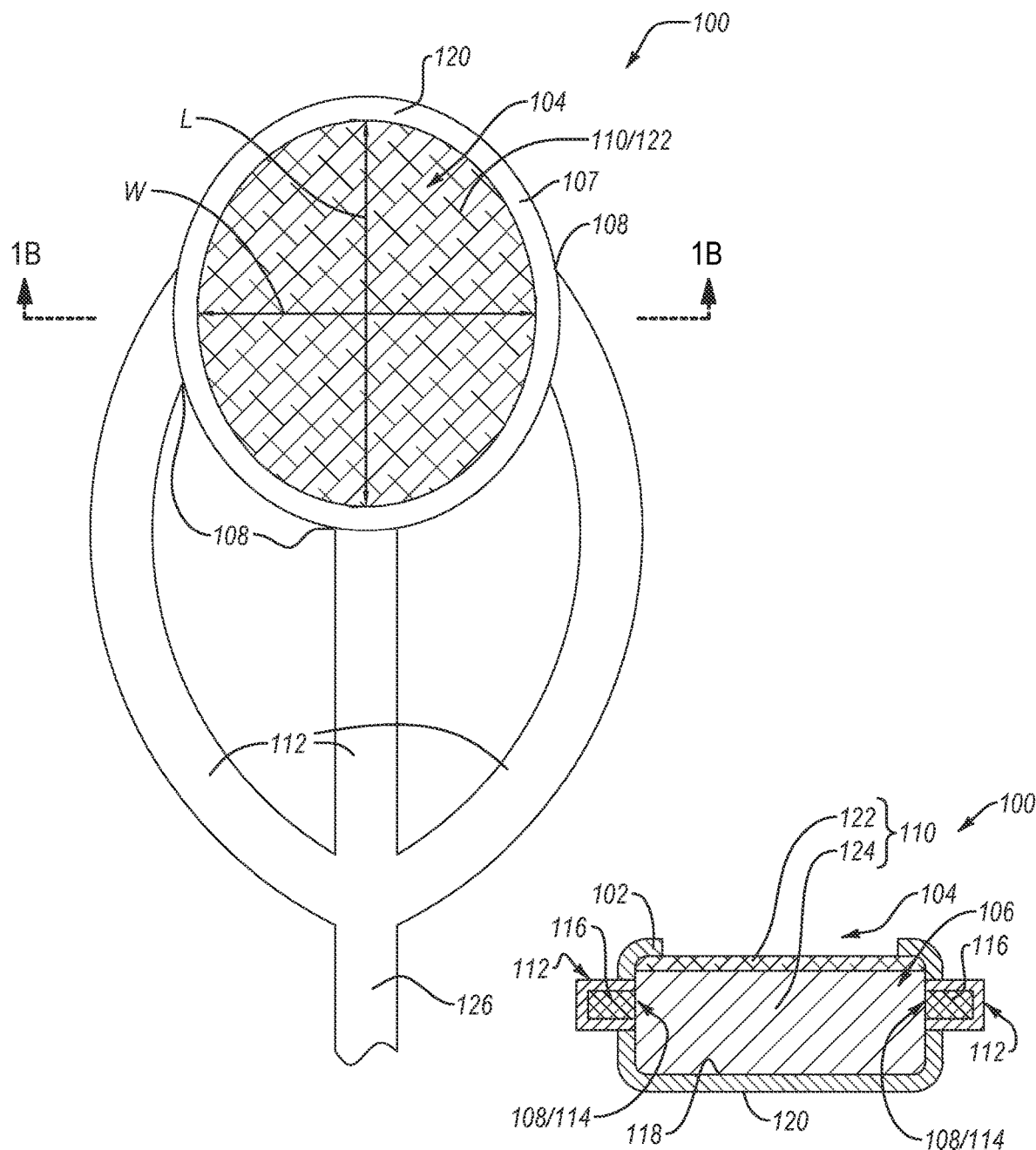
FIG. 1A is a top plan view of a fluid collection assembly that includes one or more leak prevention features, according to an embodiment.
FIG. 1B is a cross-sectional view of the fluid collection assembly taken along line 1B-1B shown in FIG. 1A, according to an embodiment.

FIG. 1A is a top plan view of a fluid collection assembly 100 that includes one or more leak prevention features, according to an embodiment. FIG. 1B is a cross-sectional view of the fluid collection assembly 100 taken along line 1B-1B shown in FIG. 1A, according to an embodiment. The fluid collection assembly 100 includes a fluid impermeable barrier 102. The fluid impermeable barrier 102 defines at least one opening 104 configured to receive bodily fluids from an individual. The fluid impermeable barrier 102 also defines a chamber 106 that is in fluid communication with the opening 104 and at least one fluid outlet 108. The fluid collection assembly 100 also include at least one porous material 110 disposed in the chamber 106 and at least one conduit 112 attached to the fluid outlet 108. The fluid collection assembly 100 also include one or more leak prevention features.

In an embodiment, the leak prevention features of the fluid collection assembly 100 includes forming the fluid collection assembly 100 to exhibit a generally non-cylindrical shape. For example, some conventional fluid collection assemblies exhibit a generally cylindrical shape (e.g., bent generally cylindrical shape). Generally, the conventional fluid collection assemblies exhibiting the generally cylindrical shape rely on the thighs of the individual contacting the sides of the conventional fluid collection assembly to maintain the conventional fluid collection assembly against the vulva. However, the thighs of thinner individuals may be unable to contact the sides of the conventional fluid collection assembly and/or separating the legs of the individual (e.g., for comfort or movement) may cause the thighs to cease contacting the sides of the conventional fluid collection assembly. When the thighs of the individual do not contact the sides of the conventional fluid collection assembly, at least a portion of the conventional fluid collection assembly may move away from the individual thereby creating a passageway through which bodily fluids may flow without entering the chamber of the conventional fluid collection assembly. As such, in the illustrated embodiment, the fluid collection assembly 100 exhibits a generally disk-like shape. The generally disk-like shape of the fluid collection assembly 100 has the technical effect of allowing the fluid collection assembly 100 to contact the thighs of the individual even when the individual is thin or is separating the thighs thereof.

The generally disk-like shape of the fluid collection assembly 100 allows the fluid collection assembly 100 to be relatively flat. In particular, the generally disk-like shape of the fluid collection assembly 100 allows the opening 104 and the portion of the porous material 110 adjacent to the opening 104 to be generally flat. The generally flat shape of the fluid collection assembly 100 allows the fluid collection assembly 100 to exhibit a relatively small thickness relative to conventional fluid collection assemblies. The thickness of the fluid collection assembly 100 is measured from an outer surface 120 of a portion of the fluid impermeable barrier 102 defining the opening 104 to an opposing portion of the outer surface 120 of the fluid impermeable barrier 102 in a direction that is perpendicular to a width W and length L of the opening 104. For example, the fluid collection assembly 100 may exhibit a thickness that is about 10 mm or less, about 7.5 mm or less, about 5 mm or less, or in ranges of about 2.5 mm to about 7.5 mm or about 5 mm to about 10 mm. Such thickness may make using the fluid collection assembly 100 more comfortable than conventional fluid collection assemblies which, for example, may exhibit a thickness greater than about 2 cm. It is noted that, in some embodiments, the fluid collection assembly 100 may exhibit a thickness that is greater than about 1 cm, such as at least about 2 cm or at least about 3 cm. The relatively flat shape of the fluid collection assembly 100 may also have the technical effect of allowing the fluid collection assembly 100 to collect bodily fluids from orifices other than a urethral opening, such as from a wound or sacral drainage. It is noted that other non-cylindrically shaped fluid collection assemblies disclosed herein other than the generally disk-like shaped fluid collection assembly 100 (e.g., the fluid collection assembly 200 of FIGS. 2A-2B) may also exhibit the relatively flat shape and the relatively small thickness.

The generally disk-like shape of the fluid collection assembly 100 allows the opening 104 to exhibit a larger width W than conventional fluid collection assemblies. For example, conventional fluid collection assemblies may exhibiting an opening exhibiting a length (e.g., maximum dimension of the opening) that is significantly greater than a width (e.g., a dimension of the opening that is measured perpendicular to the length) of the opening, such as the length of the opening being more than 2.5 times greater than the width. However, the generally disk-like shape of the fluid collection assembly 100 allows the opening 104 to exhibit a width W that is 50% (i.e., half of) to 100% (i.e., equal to) the length L. For example, the width W may be about 50% to about 70%, about 60% to about 80%, about 70% to about 90%, or about 80% to about 100% of the length L. The increased width W of the opening 104 relative to the length L may allow the fluid collection assembly 100 to receive more bodily fluid (i.e., prevent leaks) that flow in a directly that is generally parallel (e.g., ±30°) to the width W compared to convention fluid collection assemblies while receiving the same or substantially the same amount of bodily fluids that flow in a direction that is generally parallel to the length L. The increased width W of the opening 104 relative to the length L may also allow the fluid collection assembly 100 to accommodate larger displacements (e.g., caused by the individual moving) in a direction that is generally parallel to the width W without leaking than conventional fluid collection assemblies while being able to accommodate the same or substantially same displacements in a direction that is generally parallel to the length L. In other words, the larger width W of the opening 104 relative to the length L of the opening 104 is another leak prevention feature of the fluid collection assembly 100.

In an embodiment, the generally flat shape of the fluid collection assembly 100 and/or the relatively large width W of the opening 104 relative to the length L of the opening 104 allows the fluid collection assembly 100 to be secured to the individual by merely resting the fluid collection assembly 100 on the individual (e.g., resting the fluid collection assembly 100 adjacent to the urethral opening). In an embodiment, the generally flat shape of the fluid collection assembly 100 and/or the relatively large width W of the opening 104 relative to the length L of the opening 104 allows the fluid collection assembly 100 to be secured to the individual using an adhesive, straps, or underwear (e.g., the underwear includes a pocket that receives the fluid collection assembly 100 and/or the underwear is configured to press the fluid collection assembly 100 against the urethral opening).

As will be discussed in more detail below, the fluid collection assembly 100 may exhibit a shape that is not a generally disk-like shape. For example, the fluid collection assembly 100 may exhibit a generally semi-cylindrical shape (FIGS. 2A and 2B), a generally flat elongated shape, a generally cylindrical shape (FIG. 3A), or any other suitable shape.

Referring to FIG. 1B, in an embodiment, the one or more leak prevention features includes occupying substantially all of the chamber 106 with the porous material 110. For example, some fluid collection assemblies (e.g., the fluid collection assemblies 300, 400, 600, and 700 of FIGS. 3B, 4, 6 and 7) include substantially unoccupied fluid reservoir in which bodily fluids may pool before the bodily fluids are removed from the chamber. During normal operation, gravity, the suction force, and fluid dynamics (capillary action and wicking) pulls the bodily fluids from the opening towards these fluid reservoirs. However, movement of the individual using these fluid collection assemblies may cause the bodily fluids pooled in the fluid reservoirs to shift (e.g., splash) into the porous materials in sufficient quantities that gravity, the suction force, and fluid dynamics cannot prevent at least some of the bodily fluids from exiting the chamber through the opening. However, referring back to the fluid collection assembly 100, substantially occupying all of the chamber 106 with the porous material 110 prevents the bodily fluids from pooling in a single location. Instead, the bodily fluids are distributed through the chamber 106. As such, no single location in the chamber 106 may include a sufficient quantity of bodily fluids that, when the individual using the fluid collection assembly 100 moves, gravity, the suction force, and fluid dynamics does not pull the bodily fluids towards at least one inlet 114 of the conduit 112. In other words, substantially occupying the chamber 106 with the porous material 110 may decrease the likelihood that the fluid collection assembly 100 leaks fluids when the individual moves. Further, substantially occupying the chamber 106 allows the conduit 112 to remove the bodily fluids regardless of the quantity of bodily fluids that are present in the chamber 106, unlike the fluid reservoirs that must receive a certain quantity of bodily fluids before the conduit 112 may remove the bodily fluids. As such, the fluid reservoirs may cause a delay between receiving the bodily fluids and removing the bodily fluids which may increase the likelihood of leaks while substantially occupying all of the chamber 106 with the porous material 110 prevents such leaks.

In an embodiment, the one or more leak prevention features includes at least one additional porous material 116 at least partially occupying an interior of the conduit 112. As used herein, the additional porous material 116 may be integrally formed with at least a portion of the porous material 110 that is disposed in the chamber 106 (e.g., the additional porous material 116 and at least a portion of the porous material 110 exhibit single piece construction) or the additional porous material 116 may be distinct from the porous material 110. When the conduit 112 is not at least partially occupied with the additional porous material 116, the conduit 112 may require a suction force to remove bodily fluids from the chamber 106. In some embodiments, the suction force applied to the conduit 112 is not continuous since the constant air flow may dry the skin and/or the suction force may cause hickeys. As such, the suction force may not be applied to the conduit 112 when discharge of the bodily fluids (e.g., urination) is not expected. However, unexpected bodily fluid discharge may saturate the porous material 110 and cause the fluid collection assembly 100 to leak when a suction force is not applied to the conduit 112 without the additional porous material 116. However, when the conduit 112 is at least partially occupied by the additional porous material 116, the additional porous material 116 may pull the bodily fluids into the conduit 112 via capillary action, absorption, and/or wicking even when a suction force is not applied to the conduit 112. Even though the additional porous material 116 may be unable to pull the fluid completely through the conduit 112 or may pull the bodily fluids through the conduit 112 more slowly than the suction force, the additional porous material 116 may increase the quantity of bodily fluids that the fluid collection assembly 100 may receive before the porous material 110 saturates and the fluid collection assembly 100 leaks.

The additional porous material 116 extends inwardly from the inlet 114 of the conduit 112. The additional porous material 116 is positioned in the conduit 112 to contact the porous material 110 or such that any gap between the porous material 110 and the additional porous material 116 is sufficiently small that only a small quantity of bodily fluids is necessary to bridge the gap. In an embodiment, the additional porous material 116 may extend through an entirety of the conduit 112 which allows the additional porous material 116 to pull the bodily fluids a far distance into the conduit 112, such as through an entirety of the conduit 112. In an embodiment, the additional porous material 116 only extends inwardly from the inlet 114 for a distance that is less than a length of the conduit 112. Only extending the additional porous material 116 through a portion of the conduit 112 may improve fluid flow in the conduit 112. For example, the additional porous material 116 may slightly obstruct fluid flow in the portions of the conduit 112.

In an embodiment, the one or more leak prevention features includes a plurality of fluid outlets 108 and at least one conduit 112 extending from each of the fluid outlets 108. For example, the conduit 112 preferentially removes bodily fluids that are closer to the inlet 114. The plurality of fluid outlets 108 and the conduit 112 attached to each of the fluid outlets 108 allows a larger volume of the bodily fluids that are present in the chamber 106 to be preferentially removed from the chamber 106. In other words, the plurality of fluid outlets 108 and the conduit 112 decrease the amount of bodily fluids that remain in the chamber 106 thereby decreasing the likelihood that the fluid collection assembly 100 leaks. Further, the plurality of conduits 112 better distribute any pressure that is applied from the fluid collection assembly 100 to the individual thereby decreasing the likelihood that the fluid collection assembly 100 causes pressure ulcers. The conduits 112 may also be flat tubes which may make the conduits 112 more comfortable against the skin.

As previously discussed, the fluid impermeable barrier 102 at least partially defines an opening 104 and a chamber 106 (e.g., interior region). For example, at least one inner surface 118 of the fluid impermeable barrier 102 at least partially defines the chamber 106 within the fluid collection assembly 100. The fluid impermeable barrier 102 temporarily stores the bodily fluids in the chamber 106. The fluid impermeable barrier 102 may be formed of any suitable fluid impermeable material(s), such as a fluid impermeable polymer (e.g., silicone, polypropylene, polyethylene, polyethylene terephthalate, a polycarbonate, etc.), a metal film, natural rubber, another suitable material, or combinations thereof. As such, the fluid impermeable barrier 102 substantially prevents the bodily fluids from passing through the fluid impermeable barrier 102. In an example, the fluid impermeable barrier 102 may be air permeable and fluid impermeable. In such an example, the fluid impermeable barrier 102 may be formed of a hydrophobic material that defines a plurality of pores. At least one or more portions of at least an outer surface 120 of the fluid impermeable barrier 102 may be formed from a soft and/or smooth material, thereby reducing chaffing. During use, the outer surface 120 of the fluid impermeable barrier 102 may contact the wearer. The fluid impermeable barrier 102 may be sized and shaped to fit in the gluteal cleft between the legs of a female user.

Figure 3A:
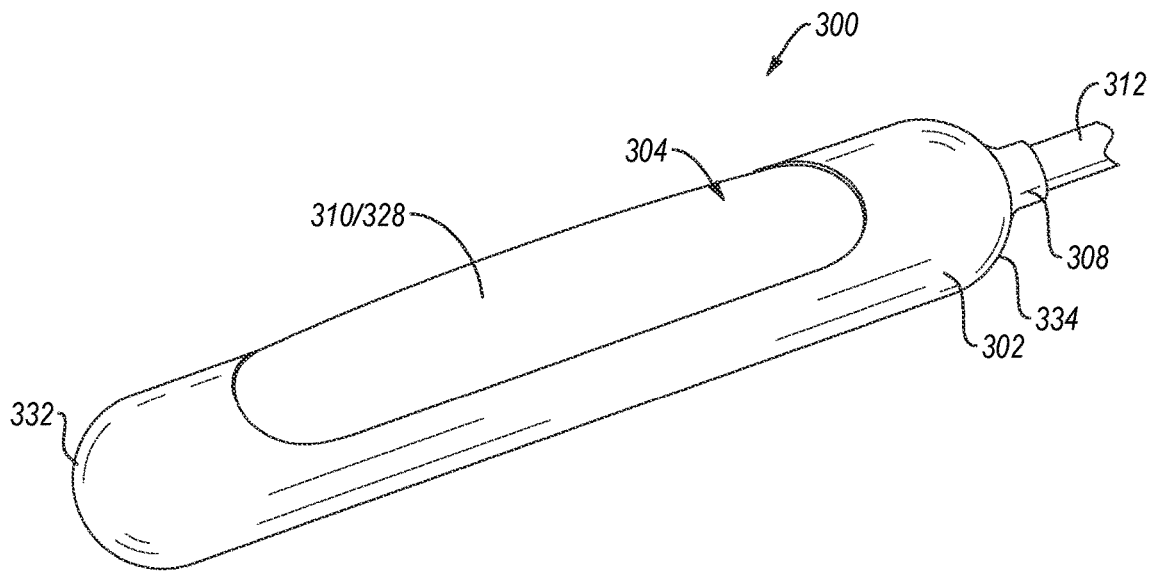
FIGS. 3A and 3B are isometric and cross-sectional views of a fluid collection assembly, respectively, according to an embodiment.

The opening 104 provides an ingress route for bodily fluids to enter the chamber 106. The opening 104 may be defined by the fluid impermeable barrier 102 such as by an inner edge of the fluid impermeable barrier 102. For example, the opening 104 is formed in and extends through the fluid impermeable barrier 102, from the outer surface 120 to the inner surface 118, thereby enabling the bodily fluids to enter the chamber 106 from outside of the fluid collection assembly 100. In an embodiment, the opening 104 may be an elongated hole (the length L is more than 50% greater than the width W, as shown in FIG. 3A) in the fluid impermeable barrier 102. For example, the opening 104 may be defined as a cut-out in the fluid impermeable barrier 102. The opening 104 may be located and shaped to be positioned adjacent to a female urethral opening.

The fluid collection assembly 100 may be positioned proximate to the female urethral opening and urine may enter the chamber 106 of the fluid collection assembly 100 via the opening 104. The fluid collection assembly 100 is configured to receive the bodily fluids into the chamber 106 via the opening 104. When in use, the opening 104 may extend from a first location above the urethral opening (e.g., at or near the top of the urethral opening or the pubic hair) to a second location below the urethral opening (e.g., at or near the anus or the vaginal opening).

In some examples, as previously discussed, the fluid impermeable barrier 102 may define an fluid outlet 108 sized to receive the conduit 112. The at least one conduit 112 may be disposed in the chamber 106 or otherwise in fluid communication with the chamber 106 via the fluid outlet 108. The fluid outlet 108 may be sized and shaped to form an at least substantially fluid tight seal against the conduit 112 or the at least one tube thereby substantially preventing the bodily fluids from escaping the chamber 106.

The fluid impermeable barrier 102 may include markings thereon, such as one or more markings to aid a user in aligning the fluid collection assembly 100 on the wearer. For example, a line on the fluid impermeable barrier 102 (e.g., opposite the opening 104) may allow a healthcare professional to align the opening 104 over the urethral opening of the individual wearing the fluid collection assembly 100. In examples, the markings may include one or more of alignment guide or an orientation indicator, such as a stripe or hashes. Such markings may be positioned to align the fluid collection assembly 100 to one or more anatomical features such as a pubic bone, etc.

As previously discussed, the fluid collection assembly 100 includes porous material 110 disposed in the chamber 106. The porous material 110 may cover at least a portion (e.g., all) of the opening 104. The porous material 110 is exposed to the environment outside of the chamber 106 through the opening 104. The permeable properties referred to herein may be wicking, capillary action, absorption, diffusion, or other similar properties or processes, and are referred to herein as "permeable" and/or "porous." The porous material 110 may also wick the bodily fluids generally towards an interior of the chamber 106, as discussed in more detail below. The porous material 110 may include one or more of a fluid permeable membrane 122 or a fluid permeable support 124.

In an embodiment, at least a portion of the porous material 110 may be a wicking material configured to wick any of the bodily fluids away from the opening 104, thereby preventing bodily fluids from escaping the chamber 106. The wicking material may not include absorption of the bodily fluids into the wicking material. Put another way, substantially no absorption of the bodily fluids into the wicking material may take place after the wicking material is exposed to the bodily fluids. While no absorption is desired, the term "substantially no absorption" may allow for nominal amounts of absorption of the bodily fluids into the wicking material (e.g., absorbency), such as less than about 30 wt % of the dry weight of the wicking material, less than 20 wt %, less than 10 wt %, less than about 7 wt %, less than about 5 wt %, less than about 3 wt %, less than about 2 wt %, less than about 1 wt %, or less than about 0.5 wt % of the dry weight of the wicking material. In an embodiment, at least a portion of the porous material 100 may include an absorbent or adsorbent material.

The fluid collection assembly 100 may include the fluid permeable membrane 122 disposed in the chamber 106. The fluid permeable membrane 122 may cover at least a portion (e.g., all) of the opening 104. The fluid permeable membrane 122 may be composed to pull/push the bodily fluids away from the opening 104, thereby preventing the bodily fluids from escaping the chamber 106.

The fluid permeable membrane 122 may include any material that may be permeable to the bodily fluids. For example, the fluid permeable membrane 122 may include fabric, such as a gauze (e.g., a silk, linen, or cotton gauze), another soft fabric, or another smooth fabric. Forming the fluid permeable membrane 122 from gauze, soft fabric, and/or smooth fabric may reduce chaffing caused by the fluid collection assembly 100.

The fluid collection assembly 100 may include the fluid permeable support 124 disposed in the chamber 106. The fluid permeable support 124 is configured to support the fluid permeable membrane 122 since the fluid permeable membrane 122 may be formed from a relatively foldable, flimsy, or otherwise easily deformable material. For example, the fluid permeable support 124 may be positioned such that the fluid permeable membrane 122 is disposed between the fluid permeable support 124 and the fluid impermeable barrier 102. As such, the fluid permeable support 124 may support and maintain the position of the fluid permeable membrane 122. The fluid permeable support 124 may include any material that may be permeable to the bodily fluids, such as any of the fluid permeable membrane materials disclosed herein above. For example, the fluid permeable membrane material(s) may be utilized in a more dense or rigid form than in the fluid permeable membrane 122 when used as the fluid permeable support 124. The fluid permeable support 124 may be formed from any fluid permeable material that is less deformable than the fluid permeable membrane 122. For example, the fluid permeable support 124 may include a porous polymer (e.g., nylon, polyester, polyurethane, polyethylene, polypropylene, etc.) structure (e.g., spun fibers, such as spun nylon fibers) or an open cell foam. In some examples, the fluid permeable support 124 may be formed from a natural material, such as cotton, wool, silk, or combinations thereof. In such examples, the material may have a coating to prevent or limit absorption of the bodily fluids into the material, such as a water repellent coating. In some examples, the fluid permeable support 124 may be formed from fabric, felt, gauze, or combinations thereof. In some examples, the fluid permeable membrane 122 may be optional. For example, the porous material 110 may include only the fluid permeable support 124. In some examples, the fluid permeable support 124 may be optionally omitted from the fluid collection assembly 100. For example, the porous material 110 may only include the fluid permeable membrane 122.

In an embodiment, the fluid permeable membrane 122 and the fluid permeable support 124 are wicking materials. In such an embodiment, the fluid permeable support 124 may have a greater ability to wick the bodily fluids than the fluid permeable membrane 122, such as to move the bodily fluids inwardly from the outer surface 120 of the fluid collection assembly 100. In some examples, the wicking ability of the fluid permeable support 124 and the fluid permeable membrane 122 may be substantially the same.

As previously discussed, the fluid permeable membrane 122 and the fluid permeable support 124 may at least substantially completely fill the portions of the chamber 106 that are not occupied by the conduit 112. In an example, not shown, the fluid permeable membrane 122 and the fluid permeable support 124 may not substantially completely fill the portions of the chamber 106 that are not occupied by the conduit 112. In such an example, the fluid collection assembly 100 includes a fluid reservoir (e.g., fluid reservoir 336 illustrated in FIG. 3B) disposed in the chamber 106.

The fluid reservoir is a substantially unoccupied portion of the chamber 106. The fluid reservoir may be defined between the fluid impermeable barrier 102 and one or both of the fluid permeable membrane 122 and fluid permeable support 124. The bodily fluids that are in the chamber 106 may flow through the fluid permeable membrane 122 and/or fluid permeable support 124 to the fluid reservoir. The fluid reservoir may retain of the bodily fluids therein. The bodily fluids that are in the chamber 106 may flow through the fluid permeable membrane 122 and/or fluid permeable support 124 and, optionally, to the fluid reservoir. The fluid impermeable barrier 102 may retain the bodily fluids in the fluid reservoir. The fluid reservoir may be located in a portion of the chamber 106 that is designed to be located in a gravimetrically low point of the fluid collection assembly when the device is worn. In some examples (not shown), the fluid collection assembly 100 may include multiple fluid reservoirs, such as fluid reservoirs that are located adjacent to each of the fluid outlets 108.

In an embodiment, not shown, the conduit 112 may be at least partially disposed in the chamber 106. The conduit 112 may be used to remove fluid form the chamber 106. The conduit 112 (e.g., a tube) includes the inlet 114 and an outlet (not shown) positioned downstream from the inlet 114. The outlet may be operably coupled to a suction source, such as a vacuum pump for withdrawing the bodily fluids form the chamber through the conduit 112. The conduit 112 fluidly couples the chamber 106 with the fluid storage container (not shown) or the vacuum source (not shown).

The conduit 112 may include a flexible material such as plastic tubing (e.g., medical tubing). Such plastic tubing may include a thermoplastic elastomer, polyvinyl chloride, ethylene vinyl acetate, polytetrafluoroethylene, etc., tubing. In some examples, the conduit 112 may include silicon or latex. In some examples, the conduit 112 may include one or more portions that are resilient, such as to by having one or more of a diameter or wall thickness that allows the conduit to be flexible. In an embodiment, the conduit 112 may include a plurality of conduits 112 extending from each of the fluid outlet 108. In such an embodiment, each of the conduits 112 may be connected to a common conduit 126 that is connected to the vacuum source or each of the conduits 112 may be connected to the same vacuum source or different vacuum sources.

In an example, the conduit 112 is configured to be at least insertable into the chamber 106. In such an example, the conduit 112 may include one or more markers (not shown) on an exterior thereof that are located to facilitate insertion of the conduit 112 into the chamber 106. For example, the conduit 112 may include one or more markings thereon that are configured to prevent over or under insertion of the conduit 112, such as when the conduit 112 defines an inlet 114 that is configured to be disposed in or adjacent to the reservoir. In another example, the conduit 112 may include one or more markings thereon that are configured to facilitate correct rotation of the conduit 112 relative to the chamber 106. The one or more markings may include a line, a dot, a sticker, or any other suitable marking.

As described in more detail below, the conduit 112 is configured to be coupled to, and at least partially extend between, one or more of the fluid storage container (Fluid storage container 1090 of FIG. 10) and the vacuum source (vacuum source 1092 of FIG. 10). In an example, the conduit 112 is configured to be directly connected to the vacuum source (not shown). In such an example, the conduit 112 may extend from the fluid impermeable barrier 102 by at least one foot, at least two feet, at least three feet, or at least six feet. In another example, the conduit 112 is configured to be indirectly connected to at least one of the fluid storage container (not shown) and the vacuum source (not shown). In some examples, the conduit 112 is secured to a wearer's skin with a catheter securement device, such as a STATLOCK® catheter securement device available from C. R. Bard, Inc., including but not limited to those disclosed in U.S. Pat. Nos. 6,117,163; 6,123,398; and 8,211,063, the disclosures of which are all incorporated herein by reference in their entirety.

The inlet 114 and the outlet of the conduit 112 are configured to fluidly couple (e.g., directly or indirectly) the vacuum source (not shown) to the chamber 106 (e.g., the reservoir). As the vacuum source (FIG. 10) applies a vacuum/suction in the conduit 112, the bodily fluids in the chamber 106 may be drawn into the inlet 114 and out of the fluid collection assembly 100 via the conduit 112. In some examples, the conduit 112 may be frosted or opaque (e.g., black) to obscure visibility of the bodily fluids therein.

FIG. 2A is a top plan view of a fluid collection assembly 200, according to an embodiment. Except as otherwise disclosed herein, the fluid collection assembly 200 is the same or substantially similar to any of the fluid collection assemblies disclosed herein. For example, the fluid collection assembly 200 includes a fluid impermeable barrier 202 defining an opening 204, a chamber 206, and at least one fluid outlet 208. The fluid collection assembly 200 also includes at least one porous material 210 disposed in the chamber 206 and a conduit 212 attached to the fluid outlet 208.

The fluid collection assembly 200 exhibits a generally elongated shape. The elongated shape of the fluid collection assembly 200 may allow the fluid collection assembly 200 to exhibit a size and shape that fits in the gluteal cleft between the legs of an individual, especially a non-thin individual. The elongated shape of the fluid collection assembly 200 allows the opening 204 to exhibit an elongated shape wherein a length L of the opening 204 is greater (e.g., at least about 1.5 times greater, at least about 2 times greater, or at least 3 times greater) than the width W of the opening 204. The opening 204 may have an elongated shape because the space between the legs of a female is relatively small when the legs of the female are closed, thereby only permitting the flow of the bodily fluids along a path that corresponds to the elongated shape of the opening 204 (e.g., longitudinally extending opening). The opening 204 in the fluid impermeable barrier 202 may exhibit a length that is measured along the longitudinal axis of the fluid collection assembly 200 that may be at least about 10% of the length of the fluid collection assembly 200, such as about 25% to about 50%, about 40% to about 60%, about 50% to about 75%, about 65% to about 85%, or about 75% to about 95% of the length of the fluid collection assembly 200.

The leak prevention feature of the fluid impermeable barrier 202 may include the cross-sectional shape of the fluid impermeable barrier 202. FIG. 2B is a cross-sectional view of the fluid impermeable barrier 202 taken along ling 2B-2B, according to an embodiment. As shown in FIG. 2B, the fluid impermeable barrier 202 may exhibit a concavely curved cross-sectional shape, such as a generally semi-circular (e.g., generally half circular) cross-sectional shape or other generally elliptical cross-sectional shape. In an embodiment, the concavely curved cross-sectional shape of the fluid impermeable barrier 202 inhibits leaks because the curved outermost surface 228 of the porous material 210 (e.g., the surface of the porous material 210 extending across the opening 204) is able to press against the labia folds of the vulva and may even cause the outermost surface 228 to extend between labia folds. Pressing the outermost surface 228 against the labia folds may cause the fluid collection assembly 200 to receive bodily fluids that would otherwise flow between the labia folds.

In an embodiment, the concavely curved cross-sectional shape of the fluid impermeable barrier 202 allows the conduit 212 to be positioned adjacent to a back surface 218 of the fluid impermeable barrier 202. Since the conduit 212 is positioned adjacent to the back surface 218, any air flow caused by a suction force applied to the conduit 212 is concentrated between the inlet of the conduit 212 and the opening 204. This concentration of the air flow may increase the amount of bodily fluids that are sucked into the conduit 212 and are removed from the chamber 206. Meanwhile, a substantially similar fluid collection assembly that includes a conduit spaced from the back surface may cause some of the air to flow between the conduit and the back surface of the fluid impermeable barrier thereby decreasing the amount of air flow between the opening and the conduit and the amount of bodily fluids received by the conduit.

The porous material 210 of the fluid impermeable barrier 202 includes a fluid permeable membrane 222 and a fluid permeable support 224. In an embodiment, the porous material 210 may include at least one absorbent layer 230 positioned between the fluid permeable membrane 222 and the fluid impermeable support 224. The absorbent layer 230 may be a leak prevention feature of the fluid impermeable barrier 202. For example, the fluid permeable membrane 222 may be a wicking material. Disposing the absorbent layer 230 downstream from the fluid permeable membrane 222 may help pull bodily fluids through the fluid permeable membrane 222. As such the absorbent layer 230 may increase the flow rate of bodily fluids through the fluid permeable membrane 222 and through the chamber 206 as a whole thereby decreasing leaking caused by oversaturation of the porous material 210. The absorbent layer 230 may include any suitable absorbent material, such as, super absorbent polymers, absorbent materials used in diapers, absorbent materials used in astronaut underwear, sponge-like material, one or more hydrophilic materials, etc.

It is noted that the fluid collection assembly 200 may exhibit shapes other than the concavely curved cross-sectional shape illustrated in FIG. 2B. In an example, the fluid collection assembly 200 may exhibit an elongated shape exhibiting a generally rectangular cross-sectional shape (e.g., a generally square cross-sectional shape or a generally rectangular cross-sectional shape with one or more curved surfaces) that exhibits some of the benefits of the fluid collection assembly 100 illustrated in FIGS. 1A and 1B. In an example, the fluid collection assembly 200 may exhibit a generally cylindrical shape.

Figure 3B:
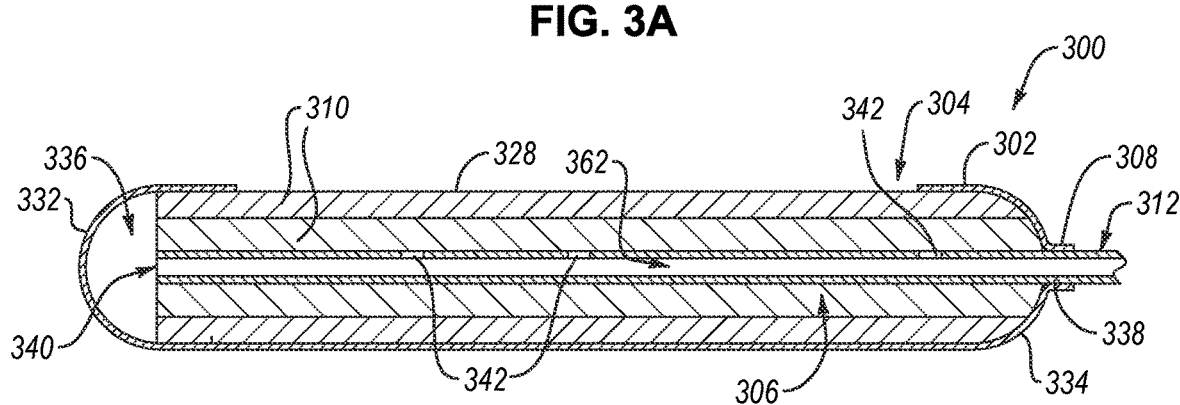

FIGS. 3A and 3B are isometric and cross-sectional views of a fluid collection assembly 300, according to an embodiment. Except as otherwise disclosed herein, the fluid collection assembly 300 may be the same or substantially to any of the fluid collection assemblies disclosed herein. For example, the fluid collection assembly 300 may include a fluid impermeable barrier 302 defining an opening 304, a chamber 306, and a fluid outlet 308. The fluid impermeable barrier 300 also includes at least one porous material 310 disposed in the chamber 306 and at least one conduit 312 secured to the fluid outlet 308.

The fluid collection assembly 300 exhibits a generally cylindrical shape. The elongated shape of the fluid collection assembly 300 may allow the fluid collection assembly 300 to exhibit a size and shape that fits in the gluteal cleft between the legs of an individual, especially a non-thin individual. The elongated shape of the fluid collection assembly 300 allows the opening 304 to exhibit an elongated shape wherein a length of the opening 304 is significantly greater than the width of the opening 304. The opening 304 may have an elongated shape because the space between the legs of a female is relatively small when the legs of the female are closed, thereby only permitting the flow of the bodily fluids along a path that corresponds to the elongated shape of the opening 304 (e.g., longitudinally extending opening). Further, the curved outermost surface of the fluid collection assembly 300, and more particularly the curved outermost surface 328 of the porous material 310, will press against the labia folders.

Referring to FIG. 3B, the fluid collection assembly 300 includes a first end 332 and a second end 334 spaced from the first end 332. The first end 332 may define a substantially unoccupied fluid reservoir 336. The second end 334 may define the fluid outlet 308. The conduit 312 may include an outlet portion 338 disposed in the fluid outlet 308. For example, the outlet portion 338 may secure the conduit 312 to the fluid outlet 308 via press fitting, an adhesive, ultrasonic welding, or any other suitable attachment technique. The conduit 312 may extend longitudinally from the fluid outlet 308, behind at least partially of the porous material 310 (e.g., through a central region of the porous material 310), to the fluid reservoir 336. For example, the conduit 312 may include an open terminal end 340 that is positioned adjacent to or within the fluid reservoir 336. The open terminal end 340 is configured to remove bodily fluids that are present in the fluid reservoir 336, for example, when a suction force is applied to the conduit 312.

The open terminal end 340 of the conduit 312 may substantially only remove bodily fluids when the bodily fluids are present in the fluid reservoir 336 in sufficient quantity that the bodily fluids contact the open terminal end 340. As such, solely relying on the open terminal end 340 to remove bodily fluids may delay removal of the bodily fluids from the chamber 306 since the bodily fluids must first flow into the fluid reservoir 336 in sufficient quantity to be removed and at least some of the bodily fluids may not be removed from the chamber 306 when the quantity of bodily fluids in the fluid reservoir 336 are insufficient to contact the open terminal end 340, both of which may increase the likelihood that the fluid collection assembly 300 leaks. As such, the one or more leak prevention features of the fluid collection assembly 300 may include at least one conduit inlet 342 formed in the conduit 312 (e.g., the conduit 312 includes a plurality of inlets, namely the open terminal end 340 and the at least one conduit inlet 342). The conduit inlet 342 includes an inlet formed in the conduit 312 between the outlet portion 338 and the open terminal end 340 that is in fluid communication with an interior 362 (e.g., passageway) of the conduit 312. As used herein, the conduit inlet 342 refer to inlets formed in the conduit 312 that are distinct from the open terminal end 340. The conduit inlet 342 allows the conduit 312 to remove bodily fluids from the chamber 306 that are spaced from the fluid reservoir 336 in addition to the bodily fluids that are present in the fluid reservoir 336. In an embodiment, not shown, the open terminal end 340 of the conduit 312 may be omitted and the conduit 312 may only include one or more conduit inlets 342.

In an embodiment, the conduit inlet 342 may include a one-way valve (not shown). The one-way valve may be configured to allow the bodily fluids to flow from an exterior (e.g., the chamber 306) of the conduit 312 into an interior 362 of the conduit 312 and restrict the flow of the bodily fluids from the interior 362 to the exterior of the conduit 312. The one-way valve may prevent bodily fluids that are received upstream from one of the conduit inlet 342 from exiting the conduit 312. Allowing the bodily fluids to exit the conduit 312 at a location downstream from where the bodily fluids were received may increase the likelihood that the fluid collection assembly 300 leaks. The one-way valve may include any suitable one-way valve. In an example, the one-way valve is a flap formed in the interior 362 of the conduit 312. The flap may be configured to open when the flow of the bodily fluids is from the exterior to the interior 362 of the conduit 312 and close when the flow of the bodily fluids is from the interior 362 to the exterior of the conduit 312. In an example, the one-way valve includes a ball valve that substantially only permits the bodily fluids to flow from the exterior to the interior 362 of the conduit 312.

Figure 3C:
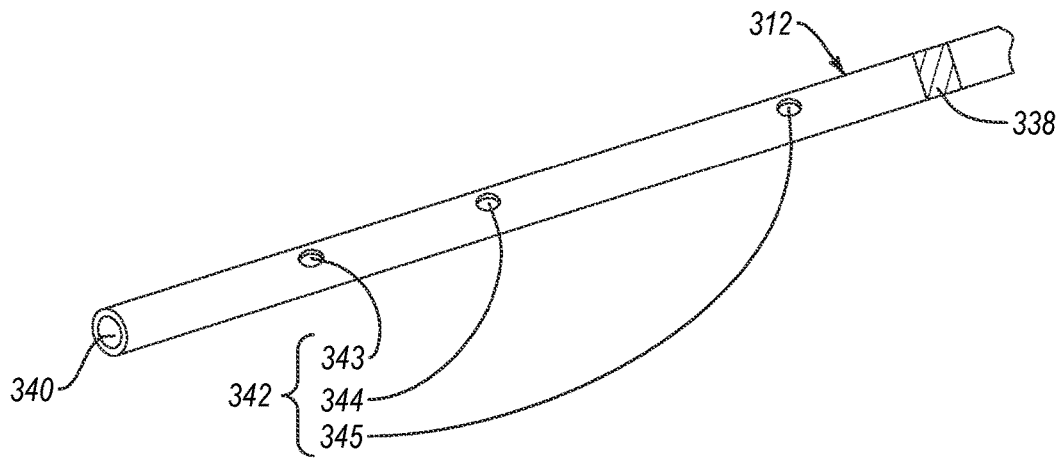
FIG. 3C is an isometric view of the conduit illustrating how the at least one conduit inlet may facilitate removing bodily fluids from the chamber when the individual using the fluid collection assembly is in a position other than lying down, according to an embodiment.

The conduit inlets 342 may also allow the fluid collection assembly 300 to be used when the individual using the fluid collection assembly 300 is in different positions. For example, when the individual is lying down, the fluid reservoir 336 is the gravimetrically lowest point of the chamber 306. As such, gravity pulls the bodily fluids towards the fluid reservoir 336 in addition to the permeability of the porous material 310 and the suction force. However, switching the position of the individual from the lying position to another position (e.g., sitting or standing position) may change the gravimetrically low point of the chamber 306. FIG. 3C is an isometric view of the conduit 312 illustrating how the at least one conduit inlet 342 may facilitate removing bodily fluids from the chamber 306 when the individual using the fluid collection assembly 300 is in a position other than lying down, according to an embodiment. For example, the conduit 312 may include one or more of the open terminal end 340 that is configured to receive bodily fluids when the individual is lying down, at least one first conduit inlet 343 that is configured to receive bodily fluids when the individual is sitting down, at least one second conduit inlet 344 that is configured to receive bodily fluids when the individual is standing up, and at least one third conduit inlet 345 that is configured to receive bodily fluids when the individual is leaning forward. In such an example, the conduit 312 may exhibit a length measured from the open terminal end 340 to the outlet portion 338 (cross-hatched for illustrative purposes). The first conduit inlet 343 may be spaced from the open terminal end 340 by about 20% to about 40% (e.g., about 20% to about 30%, about 25% to about 35%, about 30% to about 40%, or about 33%) of the length of the conduit 312 which may position the first conduit inlet 343 at or near the gravimetrically lowest point of the chamber 306 when the individual is sitting. The second conduit inlet 344 may be spaced from the open terminal end 340 by about 40% to about 60% (e.g., about 40% to about 50%, about 45% to about 55%, about 50% to about 60%, or about 50%) of the length of the conduit 312 which may position the second conduit inlet 344 at or near the gravimetrically lowest point of the chamber 306 when the individual is standing. The third conduit inlet 345 may be spaced from the open terminal end 340 by about 60% to about 99% (e.g., about 60% to about 80%, about 70% to about 90%, about 80% to about 99%) of the length of the conduit 312 which may position the third conduit inlet 345 at or near the gravimetrically lowest point of the chamber 306 when the individual is leaning forward. It is noted that the distance of the first, second, and third conduit inlets 343, 344, 345 may vary depending on the size and placement of the fluid collection assembly 300 but the values provided above are accurate for most embodiments where the fluid collection assembly 300 exhibits an elongated shape.

In an embodiment, the conduit 312 may include valve (not shown) that closes at least one of the inlets of the conduit 312 (e.g., the open terminal end 340 or one of the conduit inlets 342) when the inlet is not at or near the gravimetrically low point of the chamber 306. The valve may close the inlet when the inlet is not at or near the gravimetrically low point of the chamber 306 since the inlet is more likely to pull air into the conduit 312 when the inlet is not at or near the gravimetrically low point of the chamber 306 and decreases the overall efficiency of the conduit 312. In an example, the valve may include a ball valve that is configured to close an inlet of the conduit 312 when the inlet is not at or near the gravimetrically low point of the chamber 306 and open the inlet of the conduit 312 when the inlet is at or near the gravimetrically low point of the chamber 306. For instance, a ball of the ball valve may press against the inlet of the conduit 312 when the inlet is not at or near the gravimetrically low point of the chamber 306 and the ball of move into a recess thereby opening the inlet when the inlet is at or near the gravimetrically low point of the chamber 306.

Figure 3D:
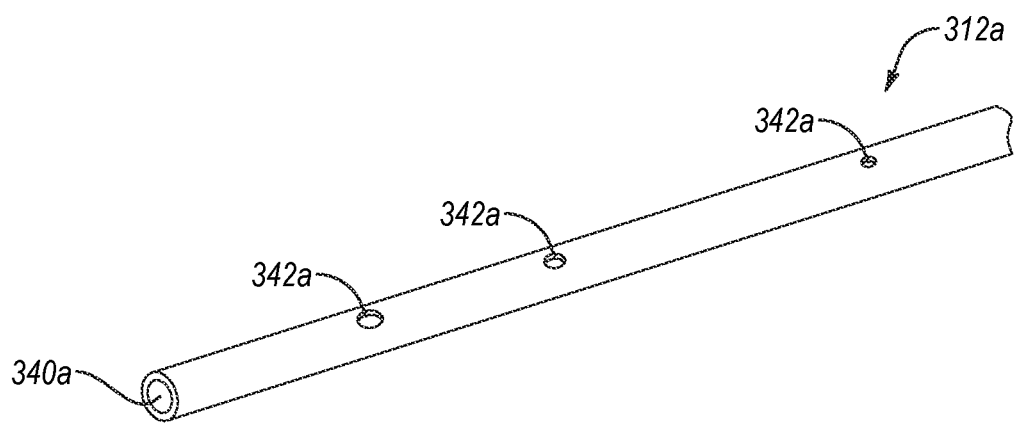
FIG. 3D is an isometric view of a conduit that may be used in any of the fluid collection assemblies disclosed herein, according to an embodiment.

FIG. 3D is an isometric view of a conduit 312*a* that may be used in any of the fluid collection assemblies disclosed herein, according to an embodiment. Except as otherwise disclosed herein, the conduit 312*a* may be the same or substantially similar to any of the conduits disclosed herein. For example, the conduit 312*a* includes an open terminal end 340*a* and at least one conduit inlet 342*a*. Generally, the open terminal end 340*a* removes more bodily fluids from a chamber (e.g., chamber 306 of FIG. 3A) than the conduit inlets 342*a* and the conduit inlets 342*a* closer to the open terminal end 340*a* remove more bodily fluids from the chamber than other conduit inlets 342*a*. Further, the inlets of the conduit 312*a* (e.g., the open terminal end 340*a* and the conduit inlets 342*a*) will remove air from the chamber preferentially over bodily fluids. In other words, if any of the inlets of the conduit 312*a* are exposed to air instead of bodily fluids, the conduit 312*a* will remove significantly less bodily fluids than if each of the inlets were exposed to the bodily fluids. As such, the inlets of the conduit 312*a* may be configured to exhibit different sizes (e.g., diameter) depending on the likelihood that the inlets will remove bodily fluids or air at any given time. For example, the open terminal end 340*a* may exhibit the largest opening (e.g., largest diameter) of the conduit 312*a* since the open terminal end 340*a* is most likely to remove the most bodily at any given time. The conduit inlets 342*a* may also exhibit different sizes, wherein the size (e.g., diameter) of the conduit inlets 342*a* progressively get smaller with increased distance from the open terminal end 340*a* since the conduit inlets 342*a* are less likely to remove bodily fluids with increased distance from the open terminal end 340*a*. The various sizes of the openings of the conduit 312*a* are leak prevention features since they decrease the amount of air pulled into the conduit 312*a* thereby increasing the amount of bodily fluids that are pulled into the conduit 312*a* and decreasing the likelihood of leaks.

Figure 3E:
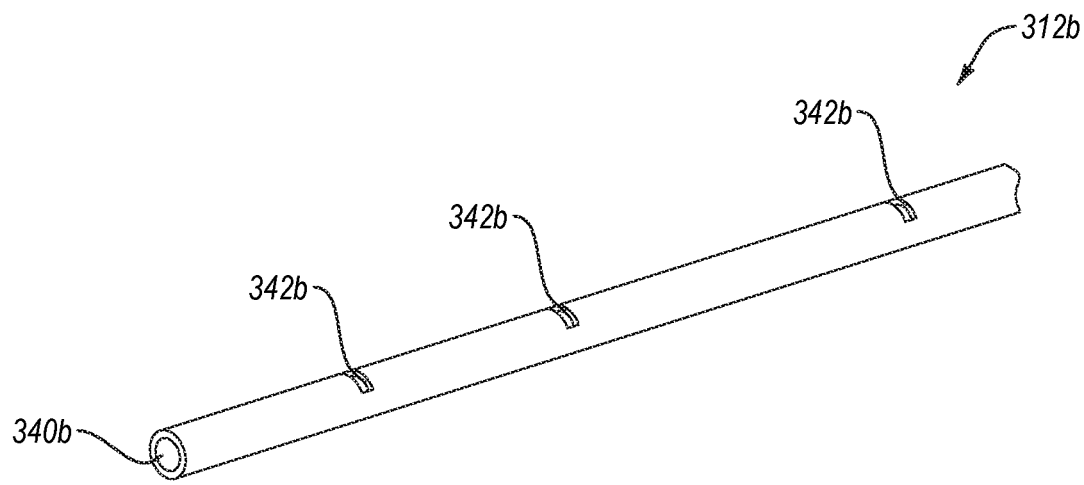
FIG. 3E is an isometric view of a conduit that may be used in any of the fluid collection assemblies disclosed herein, according to an embodiment.

The conduit inlets illustrated in FIGS. 3C and 3D exhibit a generally circular shape. However, the conduit inlets may exhibit any suitable shape. For example, FIG. 3E is an isometric view of a conduit 312*b* that may be used in any of the fluid collection assemblies disclosed herein, according to an embodiment. Except as otherwise disclosed herein, the conduit 312*b* may be the same or substantially similar to any of the conduits disclosed herein. For example, the conduit 312*b* may include an open terminal end 340*b* and at least one conduit inlet 342*b*. The conduit inlet 342*b*, in the illustrated embodiment, exhibits a slot-like shape instead of the generally circular shapes illustrated in FIGS. 3C and 3D. The slot-like shape of the conduit inlet 342*b* may increase the volume of bodily fluids that are preferentially pulled into the conduit inlet 342*b*. The slot-like shape of the conduit inlet 342*b* may also increase the flexibility of the conduit 312*b* thereby allowing the fluid collection assembly that includes the conduit 312*b* to more easily conform to the shape the individual. In other words, the slot-like shape of the conduit inlets 342*b* are leak prevention features since it may improve the amount of bodily fluids that are pulled into the conduit 312*b* and may allow the fluid collection assembly to better conform to the shape of the individual, both of which may decrease the likelihood that the fluid collection assembly leaks.

Figure 3F:
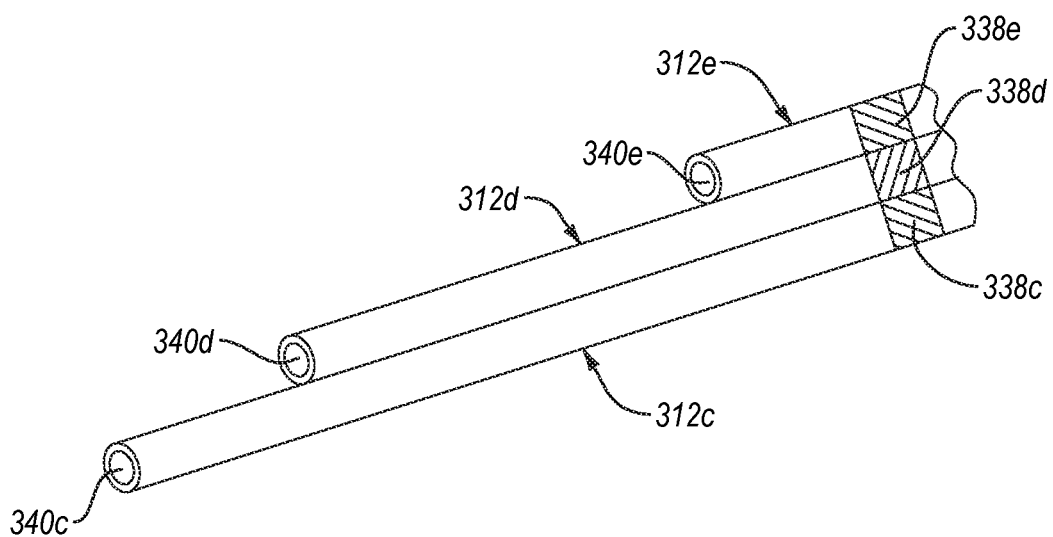
FIG. 3F is an isometric view of a plurality of conduits that may be used in any of the fluid collection assemblies disclosed herein, according to an embodiment.

FIG. 3F is an isometric view of a plurality of conduits that may be used in any of the fluid collection assemblies disclosed herein (e.g., the fluid collection assembly may include the plurality of conduits instead of a single conduits), according to an embodiment. The plurality of conduits are illustrated and discussed as having a first conduit 312*c*, a second conduit 312*d*, and a third conduit 312*e*. However, this is for illustrative purposes only and it is understood that the plurality of conduits may include two conduits or four or more conduits and that the same principles disclosed herein are applicable regardless of the number of conduits. Except as otherwise disclosed herein, each of the first, second, and third conduits 312*c*, 312*d*, 312*e* may be the same or substantially similar to any of the conduits disclosed herein. For example, each of the first, second, and third conduits 312*c*, 312*d*, 312*e* may include a first, second, and third outlet portion 338*c*, 338*d*, 338*e* (cross-hatched for illustrative purposes) and a first, second, and third open terminal end 340*c*, 340*d*, 340*e*, respectively. At least one of the first, second, or third conduits 312*c*, 312*d*, 312*e* may also include at least one conduit inlet (not shown).

The first conduit 312*c* exhibits a first length measured from the first outlet portion 338*c* to the first open terminal end 340*c*. The second conduit 312*d* exhibits a second length measured from the second outlet portion 338*d* to the second open terminal end 340*d*. The third conduit 312*e* exhibits a third length measured from the third outlet portion 338*e* to the third open terminal end 340*e*. In an embodiment, as illustrated, the first distance is greater than the second distance and the second distance is greater than the third distance. The different distances of the first, second, and third conduits 312*c*, 312*d*, 312*e* causes the first, second, and third open terminal ends 340*c*, 340*d*, 340*e* to be positioned in different locations of a chamber. Similar to the different locations of the inlets of the conduits discussed in FIGS. 3B-3E, the different locations of the first, second, and third opening terminal ends 340*c*, 340*d*, 340*e* are leak prevention features since it allows bodily fluids to be removed from a variety of different locations in the chamber. In an embodiment, at least one of the first, second, or third distances are the same which allows the a greater volume of bodily fluids to be removed from a single location of the chamber (e.g., a fluid reservoir). In an embodiment, the first open terminal end 340*c* is larger than the second open terminal end 340*d* and the second open terminal end 340*d* is larger than the third open terminal end 340*e*. In such an embodiment, the first, second, and third conduits 312*c*, 312*d*, 312*e* may operate similar to the conduit 312*b* illustrated in FIG. 3D.

Figure 3G:
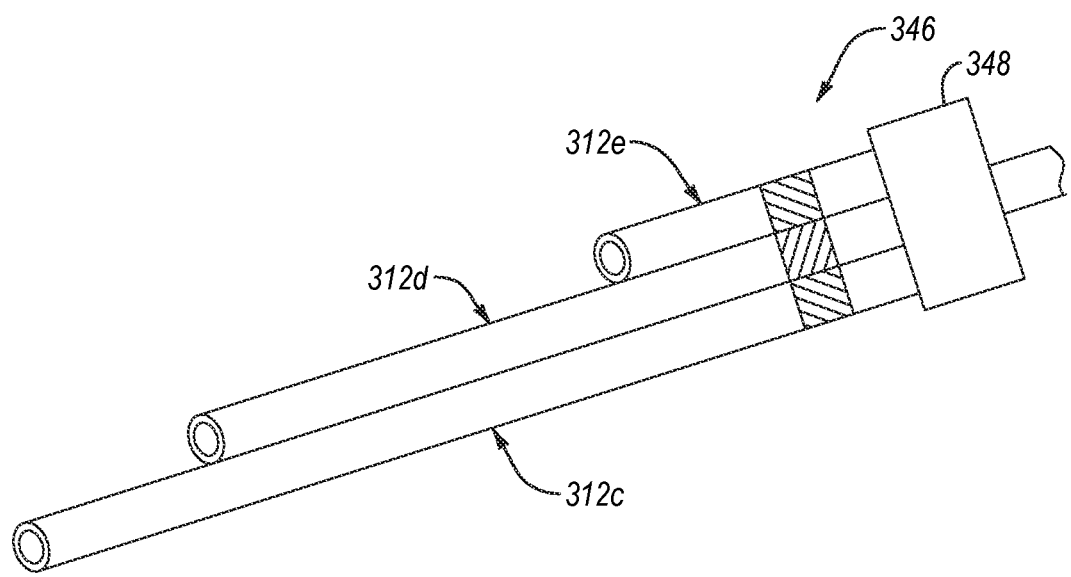
FIG. 3G is an isometric view of a system that includes the first, second, and third conduits and a suction control apparatus, according to an embodiment.

In an embodiment, the first, second, and third conduits 312*c*, 312*d*, 312*e* may intersect and form a common conduit or intersect at the fluid storage container. In such an embodiment, a suction force applied to one of the first, second, and third conduits 312*c*, 312*d*, 312*e* is also applied to the other ones of the first, second, and third conduits 312*c*, 312*d*, 312*e*. As such, each of the first, second, and third conduits 312*c*, 312*d*, 312*e* may include any of the valves discussed so that the first, second, and third conduits 312*c*, 312*d*, 312*e* to pull the bodily fluids therein and minimize the amount of air pulled therein. In an embodiment, the first, second, and third conduits 312*c*, 312*d*, 312*e* may each be connected to separate vacuum sources thereby eliminating the need for valves. However, many locations (e.g., hospitals) may not include multiple vacuum sources and/or the multiple vacuum sources may increase the cost of using a fluid collection assembly that includes the first, second, and third conduits 312c, 312d, 312e. In an embodiment, the first, second, and third conduits 312c, 312d, 312e may be connected to a suction control apparatus that controls the amount of suction that is applied to each of the first, second, and third conduits 312c, 312d, 312e. FIG. 3G is an isometric view of a system 346 that includes the first, second, and third conduits 312c, 312d, 312e and a suction control apparatus 348, according to an embodiment. The first, second, and third conduits 312c, 312d, 312e are connected to the suction control apparatus 348 and the suction control apparatus 348 is configured to control how much suction is applied to each of the first, second, and third conduits 312c, 312d, 312e. For example, the suction control apparatus 348 may include one or more sensors that detect whether the first, second, and/or third conduits 312c, 312d, 312e are removing bodily fluids or air. The sensors may include one or more moisture sensors configured to detect the presence of the bodily fluids in the conduit 312, one or more optical sensors configured to detect the presence of the bodily fluids in an at least partially transparent conduit 312, one or more acoustic sensors configured to detect the sound of bodily fluids through the conduit 312, one or more oxygen sensors configured to detect the presence of oxygen (e.g., air) in the conduit 312, or any other suitable sensor. The suction control apparatus 348 may include control circuitry that, responsive to what is sensed by the sensors, may decrease the suction force applied to which ever ones of the first, second, and/or third conduits 312c, 312d, 312e are removing air while maintaining and/or increasing the suction force applied to whichever ones of the first, second, and/or third conduits 312c, 312d, 312e are pulling bodily fluids. The suction control apparatus 348 may be a leak prevention features since the suction control apparatus 348 may cause more bodily fluids to be removed from the chamber than if the system 346 did not include the suction control apparatus 348.

Figure 4:
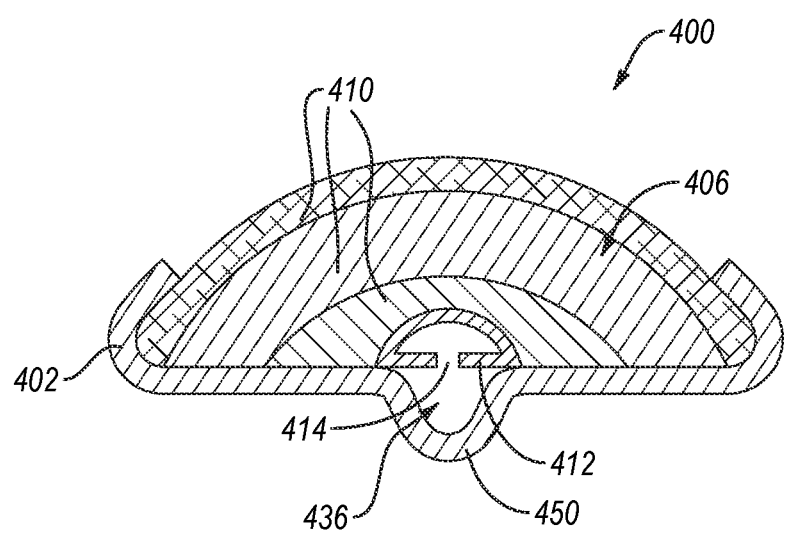
FIG. 4 is cross-sectional view of a fluid collection assembly that includes a fluid reservoir extending along the conduit, according to an embodiment.

As previously discussed, the conduits discussed with regards to FIGS. 3A-3F are configured to collect bodily fluids from a variety of locations in the chamber. However, the ability of the conduits to remove the bodily fluids are partially obstructed and slowed by the porous material. For example, as previously discussed, the porous material may obstruct flow of the bodily fluids more than unoccupied space. As such, a leak prevention feature that may be used in any of the fluid collection assemblies disclosed herein includes a substantially unoccupied fluid reservoir extending along the conduit to improve fluid flow to the different locations along the conduit. For example, FIG. 4 is a cross-sectional view of a fluid collection assembly 400 that includes a fluid reservoir 436 extending along the conduit 412, according to an embodiment. Except as otherwise disclosed herein, the fluid collection assembly 400 is the same or substantially similar to any of the fluid collection assemblies disclosed herein. For example, the fluid collection assembly 400 is illustrated as being substantially similar to the fluid collection assembly 200 and, as such, includes a fluid impermeable barrier 402 defining a chamber 406, at least partially porous material 410 disclosed in the chamber 406, and at least one conduit 412. However, it is noted that the principles discussed herein are also applicable to the other fluid collection assemblies disclosed herein.

The fluid collection assembly 400 includes at least one fluid reservoir 436 that is substantially unoccupied. As previously discussed, the fluid reservoir 436 extends at least partially along the length of the conduit 412. The fluid reservoir 436 may be a leak prevention feature since the fluid reservoir 436 may facilitate quick removal of any bodily fluids that are present in the chamber 406. For example, the conduit 412 may define a plurality of inlets 414 longitudinally spaced from each other, which allows the conduit 412 to remove bodily fluids from a plurality of different locations in the chamber 406. At least one of the plurality of inlets 414 of the conduit 412 may be adjacent to the fluid reservoir 436. The fluid reservoir 436 may allow the bodily fluids to quickly and easily flow to the plurality of inlets 414. For instance, the fluid reservoir 436 may allow the bodily fluids to accumulate adjacent to at least one of the inlets 414 when the individual is in a sitting position. The fluid reservoir 436 may then allow the bodily fluids to quickly and easily flow to another one(s) of the inlets 414 when the individual moves, such as moves from the sitting position to a standing position. Thus, the fluid reservoir 436 allows for the quick removal of bodily fluids from the chamber 406, even when the individual moves.

In the illustrated embodiment, the fluid reservoir 436 is defined by and positioned between the fluid impermeable barrier 402 and the conduit 412. For example, the fluid impermeable barrier 402 may include a bulge 450 extending outwardly from the rest of the fluid impermeable barrier 402. The bulge 450 may partially define the fluid reservoir 436. In an embodiment, the fluid reservoir 436 is defined between at least the porous material 410 and the conduit 412, between at least the fluid impermeable barrier 402 and the porous material 410, or within the porous material 410.

Figure 5A:
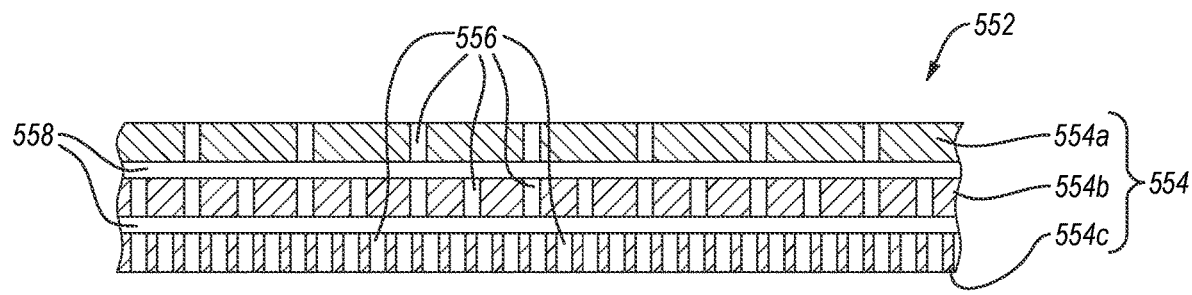
FIG. 5A is a schematic cross-sectional view of a leak prevention layer, according to an embodiment.

In an embodiment, the one or more leak prevention features of any of the fluid collection assemblies disclosed herein may include a leak prevention layer that forms a portion of the porous material. The leak prevention layer is configured to encourage flow of the bodily fluids therein in a first direction and discourage flow of the bodily fluids therein in a second direction that is opposite the first direction thereby inhibiting the bodily fluids from leaking from the chamber. FIG. 5A is a schematic cross-sectional view of a leak prevention layer 552, according to an embodiment. The leak prevention layer 552 includes a plurality of sheets 554. For example, the leak prevention layer 552 may include at least one first sheet 554a and at least one second sheet 554b positioned downstream from the first sheet 554a. As used with regards to FIGS. 5A-5C, downstream is the direction that the leak prevention layer 552 encourages the bodily fluids to flow. The downstream direction extends from the first sheet 554a towards the second sheet 554b and, during operation, generally extends from the urethral opening of the individual towards the chamber. The leak prevention layer 552 may also include one or more additional sheets positioned downstream from the second sheet 554b, such as the at least one third sheet 554c illustrated in FIG. 5A.

Each of the sheets 554 define a plurality of void spaces 556 extending therethrough. The void spaces 556 may include apertures (as shown), a plurality of interconnected pores, etc. The plurality of void spaces 556 are configured to control the flow rate of the bodily fluids flowing therethrough. Generally, the void spaces 556 are configured such that the flow rate of the bodily fluids increases the further downstream the bodily fluids flow (e.g., with further distance from the first sheet 554a and/or the urethral opening) which encourages the bodily fluids to flow in the downstream direction. The void spaces 556 also discourage the bodily fluids flowing in an upstream direction (e.g., a direction opposite the downstream direction) since the flow rate of the bodily fluids flowing in an upstream direction generally decreases. For example, referring to FIG. 5A, the leak prevention layer 552 inhibits leaks because any bodily fluids that are present in the second sheet 554b are more likely to flow to and through the third sheet 554c than the first sheet 554a (ignoring suction forces, wicking and capillary actions, and gravity). In such an example, any bodily fluids that are present in the second sheet 554b are more likely to flow to and through the third sheet 554c than the first sheet 554a since more of the bodily fluids may flow through the third sheet 554c during a given time period than the first sheet 554a.

In an embodiment, the rate at which the bodily fluids flow through each of the sheets 554 may depend on the collective cross-sectional area of the void spaces 556 (e.g., the sum of the cross-sectional area of each of the void spaces 556 along a selected plane). Generally, increasing the collective cross-sectional area of the void spaces 556 increases the flow rate of the bodily fluids and decreasing the collective cross-sectional area of the void spaces 556 decreases the flow rate of the bodily fluids. As such, the collective cross-sectional area of the void spaces 556 generally increases in the downstream direction.

In an embodiment, the collective cross-sectional area of the void spaces 556 depends on the number density of void spaces 556 that are formed in each of the sheets 554 in a selected area. In such an embodiment, the number density of void spaces 556 formed in each sheet 554 generally increases in the downstream direction. For example, as illustrated, the first sheet 554a may exhibit a first number density of the void spaces 556, the second sheet 554b may exhibit a second number density of void spaces 556 that is greater than the first number density, and the third sheet 554c may exhibit a third number density of void spaces 556 that is greater than the second number density.

In an embodiment, the collective cross-sectional area of the void spaces 556 depends on the average cross-sectional area of each of the void spaces 556 that are formed in each of the sheets 554 in a selected area. In such an embodiment, the average cross-sectional area of each of the void spaces 556 formed in each sheet 554 generally increases in the downstream direction. For example, as illustrated, each of the void spaces 556 of the first sheet 554a may exhibit a first average cross-sectional area, each of the void spaces 556 of the second sheet 554b may exhibit a second average cross-sectional area that is greater than the first average cross-sectional area, and each of the void spaces 556 of the third sheet 554c may exhibit a third average cross-sectional area that is greater than the second average cross-sectional area.

In an embodiment, each of the sheets 554 are not attached to each other or only selected portions of the sheets 554 are attached to each other. In such an embodiment, passageways 558 are allowed to form between adjacent sheets 554. For example, as illustrated, the void spaces 556 of adjacent sheets 554 may not align with each other. Without the passageways 558, the bodily fluid may be unable to flow through void spaces 556 that are not aligned with each other, especially if the sheets 554 are formed from a fluid impermeable material or a material exhibiting limited fluid permeability. Thus, without the passageways 558, the leak prevention layer 552 may be unable to encourage the bodily fluids to flow in the downstream direction.

In an embodiment, the leak prevention layer 552 may be formed from wicking materials (e.g., at least one hydrophobic material). In an embodiment, the leak prevent layer 552 may be formed from any of the same materials as the fluid permeable membranes or the fluid permeable supports disclosed herein. In an embodiment, the leak prevention layer 552 may be formed from non-wicking material, such as at least one non-polyester polymer, at least one hydrophilic material, or any other absorbent or adsorbent material.

Figure 5B:
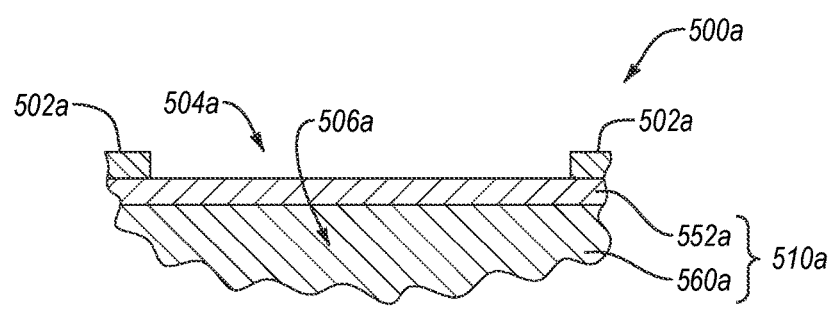
FIG. 5B is a schematic partial cross-sectional view of a portion of a fluid collection assembly that includes at least one leak prevention layer, according to an embodiment.

FIG. 5B is a schematic partial cross-sectional view of a portion of a fluid collection assembly 500a that includes at least one leak prevention layer 552a, according to an embodiment. Except as otherwise disclosed herein, the fluid collection assembly 500a is the same or substantially similar to any of the fluid collection assemblies disclosed herein. For example, the fluid collection assembly 500a may include a fluid impermeable barrier 502a defining an opening 504a and a chamber 506a. The fluid collection assembly 500a may also include at least one porous material 510a.

The porous material 510a includes the leak prevention layer 552a and at least one additional layer 560a. The additional layer 560a may include, for example, a fluid permeable membrane, a fluid permeable support, or an absorption layer. The leak prevention layer 552a extends at least partially across the opening 504a. As such, the leak prevention layer 552a may contact or otherwise be positioned proximate to the a urethral opening of the individual during operation. The additional layer 560a may be positioned downstream from the leak prevention layer 552a and support the leak prevention layer 552a.

Figure 5C:
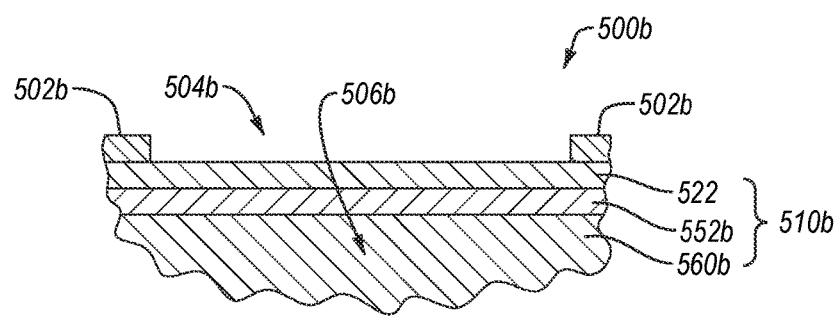
FIG. 5C is a schematic partial cross-sectional view of a portion of a fluid collection assembly that includes at least one leak prevention layer, according to an embodiment.

FIG. 5C is a schematic partial cross-sectional view of a portion of a fluid collection assembly 500b that includes at least one leak prevention layer 552b, according to an embodiment. Except as otherwise disclosed herein, the fluid collection assembly 500b is the same or substantially similar to any of the fluid collection assemblies disclosed herein. For example, the fluid collection assembly 500b may include a fluid impermeable barrier 502b defining an opening 504b and a chamber 506b. The fluid collection assembly 500b may also include at least one porous material 510b.

The porous material 510b includes the leak prevention layer 552b, a fluid permeable membrane 522, and at least one additional layer 560b. The additional layer 560b may include, for example, a fluid permeable support, or an absorption layer. The fluid permeable membrane 522 may be selected to be softer or otherwise more comfortable when contacting the vulva of an individual than the leak prevention layer 552b. As such, the fluid permeable membrane 522 extends at least partially across the opening 504b thereby preventing the leak prevention layer 552b from contacting the vulva. Instead, the fluid permeable membrane 522 may contact or otherwise be positioned proximate to the a urethral opening of the individual during operation. The leak prevention layer 552 may be positioned between the fluid permeable membrane 522 and the additional layer 560b thereby allowing the additional layer 560b to be positioned downstream from and support the leak prevention layer 552b.

Figure 6:
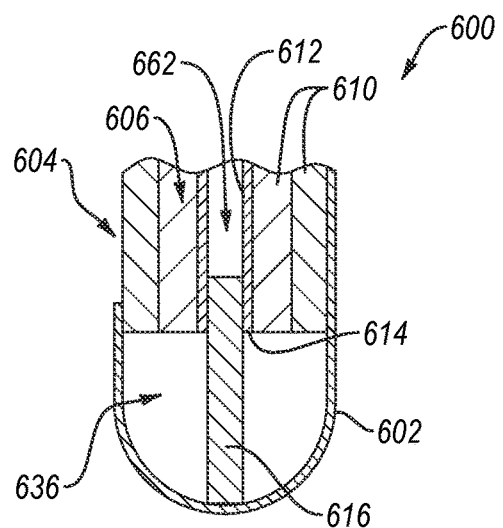
FIG. 6 is a schematic partial cross-sectional view of a portion of the fluid collection assembly, according to an embodiment.

FIG. 6 is a schematic partial cross-sectional view of a portion of the fluid collection assembly 600, according to an embodiment. Except as otherwise disclosed herein, the fluid collection assembly 600 is the same or substantially similar to any of the fluid collection assemblies disclosed herein. For example, the fluid collection assembly 600 may include a fluid impermeable barrier 602 defining an opening 604 and a chamber 606. The fluid collection assembly 600 further includes a porous material 610 and a conduit 612 disposed in the chamber 606.

The fluid collection assembly 600 also includes a fluid reservoir 636 that is substantially unoccupied. The conduit 612 includes at least one inlet 614 (e.g., open terminal end or conduit inlet) that is adjacent to or positioned in the fluid reservoir 636. The conduit 612 may not extend all the way into the fluid reservoir 636 to prevent the fluid impermeable barrier 602 from being suctioned to and completely obstructing the inlet 614. Generally, the conduit 612 is only able to remove bodily fluids that accumulate in the fluid reservoir 636 once the bodily fluids contact or are adjacent to the inlet 614, otherwise the inlet 614 merely pull air into the conduit 612. In other words, the conduit 612 may only remove bodily fluids from the fluid reservoir 636 when a certain quantity of bodily fluids are present in the fluid reservoir 636. As such, there may be a delay from when the bodily fluids enter the fluid reservoir 636 and when the conduit 612 begins to remove the bodily fluids from the fluid reservoir 636. Further, bodily fluids may remain in the fluid reservoir 636 long after the individual discharges the bodily fluids. The delay in removing the bodily fluids and leaving some bodily fluids in the fluid reservoir 636 may increase the likelihood that the fluid collection assembly 600 leaks.

The fluid collection assembly 600 may include a leak prevention feature that is configured to minimize any delay in removing the bodily fluids and minimize the amount of bodily fluids that remain the fluid reservoir 636. The leak prevention feature may include an additional porous material 616 that is partially disposed in at least a portion of an interior 662 of conduit 612. The additional porous material 616 also extends from the inlet 614 into the fluid reservoir 636, such as from the inlet 614 to the fluid impermeable barrier 602. During operation, the bodily fluids that enter the fluid reservoir 636 contact the addition porous material 616 before the bodily fluids contact or are adjacent to the inlet 614 of the conduit 612. The additional porous material 616 pulls the bodily fluids into the interior 662 of the conduit 612 via wicking, capillary action, or absorption. The conduit 612 may remove the bodily fluids that are pulled into the interior 662 of the conduit 612. Thus, the additional porous material 616 may decrease the delay between the bodily fluids entering the fluid reservoir and removing the bodily fluids from the fluid reservoir 636. Further, the additional porous material 616 may continue to pull the bodily fluids from the fluid reservoir 636 even when the individual ceases to discharge bodily fluids into the chamber 606. For example, the additional porous material 616 may remove the bodily fluids from the fluid reservoir 636 until all or substantially all of the bodily fluids are removed from the fluid reservoir 636. Thus, the additional porous material 616 decreases the likelihood that the fluid collection assembly 600 leaks the bodily fluids.

Figure 7:
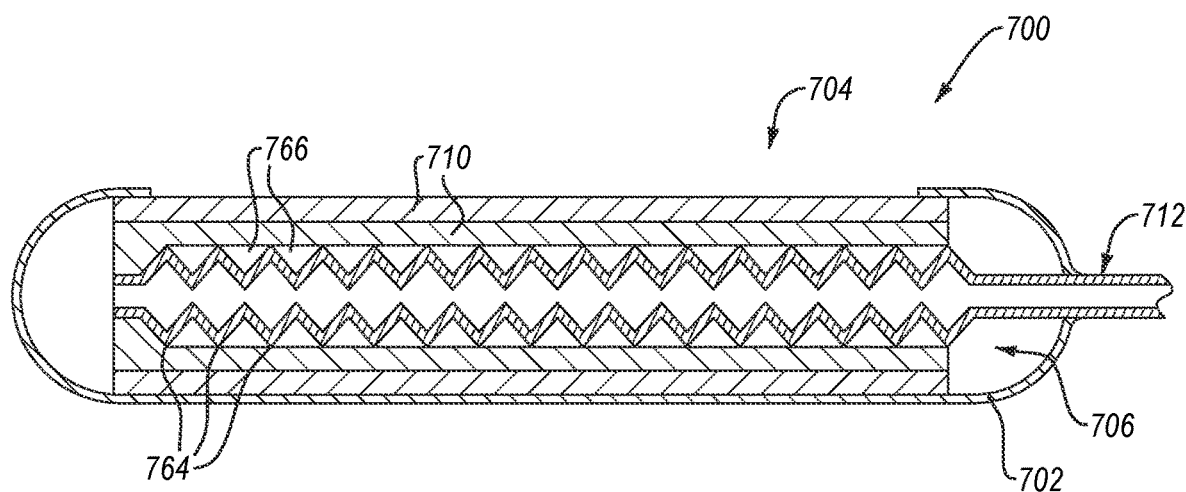
FIG. 7 is a schematic cross-sectional view of a fluid collection assembly that is configured to conform to the vulva and the region about the vulva, according to an embodiment.

In an embodiment, the one or more leak prevention features of any of the fluid collection assemblies disclosed herein include one or more features that are configured to allow the fluid collection assemblies to conform to a shape of a vulva and a region about the vulva. For example, the shape, size, and topography of the vulva and the region about the vulva may vary. These variations may cause gaps to form between the fluid collection assembly and the vulva and the region about the vulva and bodily fluids may leak through these gaps. As such, the leak prevention features may be configured to cause the fluid collection assembly to better conform to the shape, size, and topography of the vulva and the region about the vulva to eliminate or at least minimize any gaps between the fluid collection assembly and the vulva and the region about the vulva. For example, FIG. 7 is a schematic cross-sectional view of a fluid collection assembly 700 that is configured to conform to the vulva and the region about the vulva, according to an embodiment. Except as otherwise disclosed herein, the fluid collection assembly 700 may be the same or substantially similar to any of the fluid collection assemblies disclosed herein. For example, the fluid collection assembly 700 may include a fluid impermeable barrier 702 defining an opening 704 and a chamber 706. The fluid collection assembly 700 may also include at least one porous material 710 and at least one conduit 712 disposed in the chamber 706.

The conduit 712 exhibits a "crinkle" structure. For example, the conduit 712 may include one or more peaks 764 (e.g., a plurality of circumferentially extending peaks 764 or single helically extending peak 764). The conduit 712 may also include one or more valleys 766 (e.g., a plurality of circumferentially extending valleys 766 or a single helically extending valley 766) disposed between portions of the peaks 764 spaced apart along a longitudinal direction of the conduit 712. The conduit 712 may be configured to be bent. The peaks 764 and valleys 766 may allow the conduit 712 to more freely bend when an external force is applied thereto and to maintain the bent shape after the external force is removed. The bent shape of the conduit 712 also causes the rest of the fluid collection assembly 700 to bend. Thus, the conduit 712 may allow the fluid collection assembly 700 to be conformed to a shape that generally corresponds to the shape of the vulva and the region about the vulva and to maintain said shape thereby inhibiting or preventing leaks.

In an embodiment, the valleys 766 remain substantially unoccupied. For example, the porous material 710 may not extend into the valleys 766 which may prevent the porous material 710 from inhibiting the conduit 712 from bending or prevent the conduit 712 from maintaining the shape thereof after the external force is removed. Also, configuring the porous material 710 to not extend into the valleys 766 may allow the porous material 710 to be formed using an extruding process instead of other more complicated processes. In an embodiment, the valleys 766 are occupied by the porous material 710.

Figure 8:
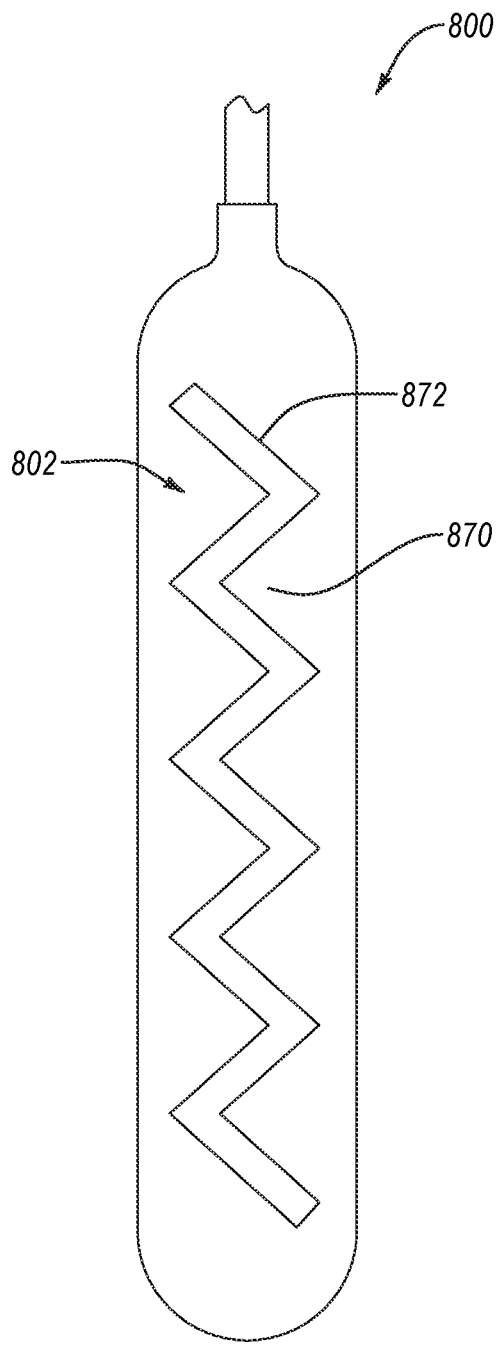
FIG. 8 is a bottom plan view of a fluid collection assembly that is configured to conform to the vulva and the region about the vulva, according to an embodiment.

FIG. 8 is a bottom plan view of a fluid collection assembly 800 that is configured to conform to the vulva and the region about the vulva, according to an embodiment. Except as otherwise disclosed herein, the fluid collection assembly 800 may be the same or substantially similar to any of the fluid collection assemblies disclosed herein. For example, the fluid collection assembly 800 may include a fluid impermeable barrier 802 defining a bottom surface 870 (e.g., the surface of the fluid impermeable barrier 802 opposite the opening defined by the fluid impermeable barrier 802).

The fluid collection assembly 800 includes a shape memory material 872. The shape memory material 872 may include a shape memory polymer or a metal (e.g., shape memory metal). Suitable shape memory materials are composed to adopt an intermediate or permanent shape in response to a stimuli. The stimuli may include an external physical force (e.g., bending force), heat, electrical bias, or a magnetic field. While the term "shape memory" is used to describe some of the "shape memory materials" herein, it should be understood that, in some examples, the material modified by the term "shape memory" may not necessarily need to return to a preselected shape upon application of a stimuli, as understood as the classical definition of the "shape memory material." Rather, at least some of the shape memory materials herein may simply hold a selected shape when bent, set, or cured into a specific shape and/or when cooled in a specific shape, regardless of the stimuli applied thereto after. The shape memory materials may be returned to the original shape or changed to a new shape by application of stimuli. For example, a metal wire bent to a first shape may be utilized as the shape memory material, whereinafter the metal wire may be modified to a second shape via physical force applied thereto or via heating. For example, the shape memory material 872 may include a shape memory alloy (e.g., nitinol), a shape memory polymer, copper, aluminum, steel, iron, or any other suitable material that is bendable and maintains its shape after being bent. In the illustrated embodiment, the shape memory material 872 is a wire exhibiting a general zig-zag shape. The generally zig-zag shape of the shape memory material 872 allows the shape memory material 872 to change the shape of a greater portion of fluid collection assembly 800 than if the shape memory material 872 was a generally straight or curved wire while exhibiting a lesser weight than if the shape memory material 872 was a plate.

In an embodiment, as illustrated, the shape memory material 872 may be attached to the bottom surface 870 of the fluid impermeable barrier 802. The shape memory material 872 may be attached to the bottom surface 870 via an adhesive or any other suitable attachment technique. When the shape memory material 872 is attached to the bottom surface 870, a coating may be applied to the shape memory material 872 to prevent the shape memory material 872 from chaffing the individual. In an embodiment, the shape memory material 872 may be disposed in the fluid impermeable barrier 802 or attached to an inner surface of the fluid impermeable barrier 802. In an embodiment, the shape memory material 872 is disposed in or attached to the at least one porous material or the conduit of the fluid collection assembly.

The composition of the shape memory material 872 and examples of different shape memory materials that may form a leak prevention feature are disclosed in International Application No. WO 2021/016026 filed on Jul. 15, 2020, the disclosure of which is incorporated herein, in its entirety, by this reference.

Some conventional fluid collection assemblies include a conduit exhibiting an outer diameter that is greater than about 1 cm that extends through substantially all of the fluid collection assembly. Such conventional fluid collection assemblies may exhibit a fluid reservoir that may hold about 10 milliliters ("ml") to about 14 ml of bodily fluids and may hold about 24 ml of bodily fluids in the chamber before leaking. Some individuals may discharge more than 24 ml of bodily fluids in the first second of urination which may cause the fluid collection assembly to leak, especially if there is any delay in removing the bodily fluids from the chamber. However, it is currently believed by the inventors that the diameter of the conduit may be decreased without decreasing the amount of bodily fluids that are removed from the chamber thereby increasing the amount of bodily fluids that may be held in the chamber. In other words, the one or more leak prevention features of any of the fluid collection assemblies disclosed herein may include using a conduit exhibiting a diameter that is about 5 mm to about 9 mm, such as in ranges of about 5 mm to about 6 mm, about 5.5 mm to about 6.5 mm, about 6 mm to about 7 mm, about 6.5 mm to about 7.5 mm, about 7 mm to about 8 mm, about 7.5 mm to about 8.5 mm, or about 8 mm to about 9 mm. In an example, a fluid collection assembly including a conduit exhibiting an outer diameter of about 9 mm may hold about 2% more bodily fluids before leaking than a substantially similar fluid collection assembly including a conduit exhibiting an outer diameter of about 1 cm (this number inherently depends on the length, diameter, and shape of the fluid collection assembly and the porosity of the porous material). The 2% increase in the amount of bodily fluids that are held in the chamber may be sufficient to prevent the fluid collection assembly from leaking. In an example, a fluid collection assembly including a conduit exhibiting an outer diameter of about 7.5 mm may hold about 5% more bodily fluids before leaking than a substantially similar fluid collection assembly including a conduit exhibiting an outer diameter of about 1 cm. The 5% increase in the amount of bodily fluids that are held in the chamber may be sufficient to prevent the fluid collection assembly from leaking. In an example, a fluid collection assembly including a conduit exhibiting an outer diameter of about 5 mm may hold about 9% more bodily fluids before leaking than a substantially similar fluid collection assembly including a conduit exhibiting an outer diameter of about 1 cm. The 9% increase in the amount of bodily fluids that are held in the chamber may be sufficient to prevent the fluid collection assembly from leaking.

In an embodiment, the one or more leak prevention features used in any of the fluid collection assemblies disclosed herein may include pre-moistening the at least one porous material before the fluid collection assemblies receive bodily fluids. Pre-moistening the porous material may include moistening the porous material with a non-bodily fluid, such as water, saline, or another suitable liquid. Pre-moistening the porous material may improve flow of the bodily fluids through the porous material. For example, the flow of the bodily fluids through a dry porous material may be slower than the flow of the bodily fluids through a moistened porous material (e.g., a pre-moistened porous material or a previously used porous material).

The fluid collection assemblies shown in FIGS. 1A-8 are examples of female fluid collection assemblies that are configured to collect bodily fluids from females. However, the fluid collection assemblies, systems, and method disclosed herein may include male fluid collection assemblies shaped, sized, and otherwise configured to collection bodily fluids from males (e.g., collect urine from a male urethral opening).

Figure 9A:
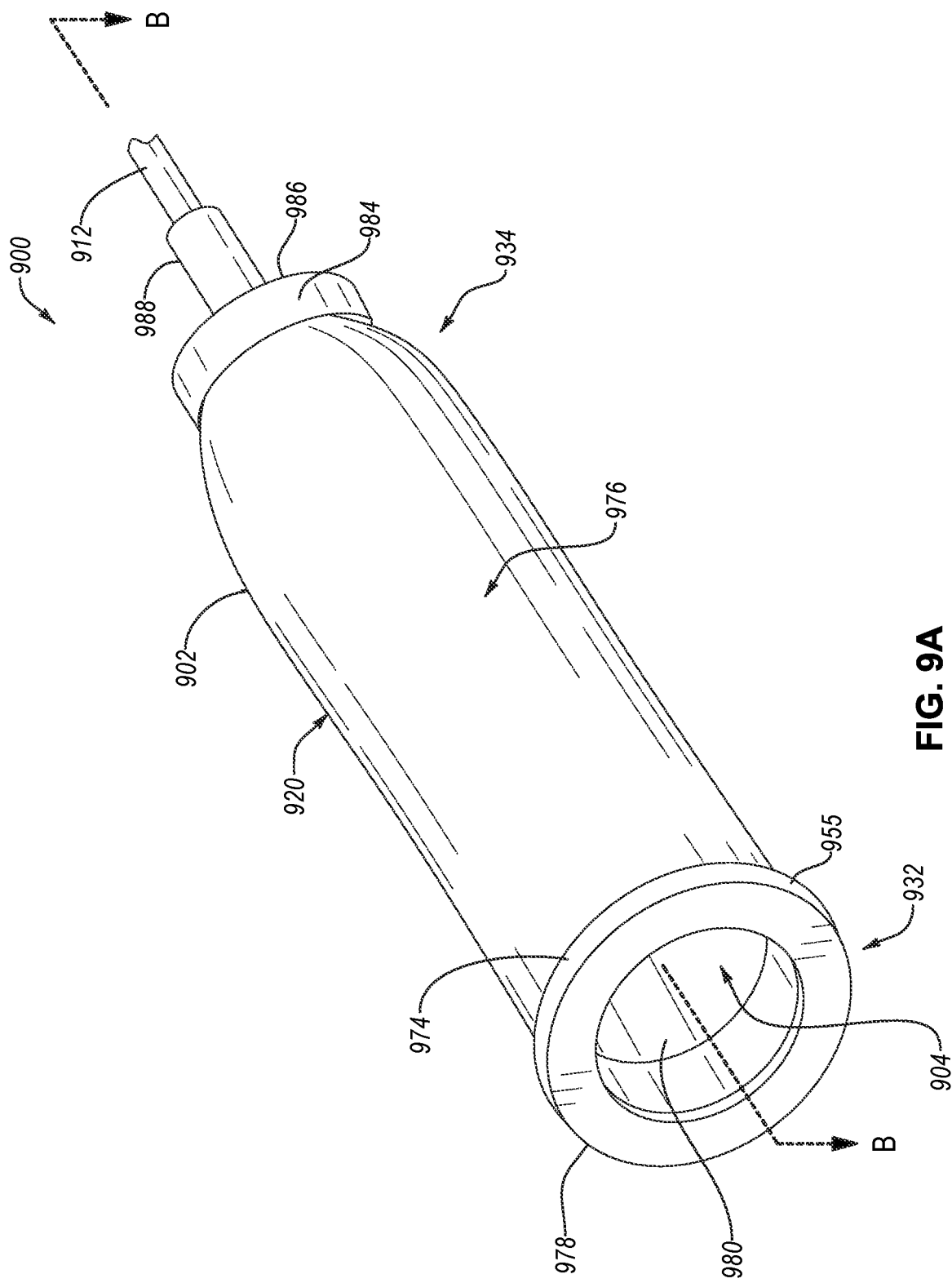
FIG. 9A is an isometric view of a fluid collection assembly according to an embodiment.
Figure 9B:
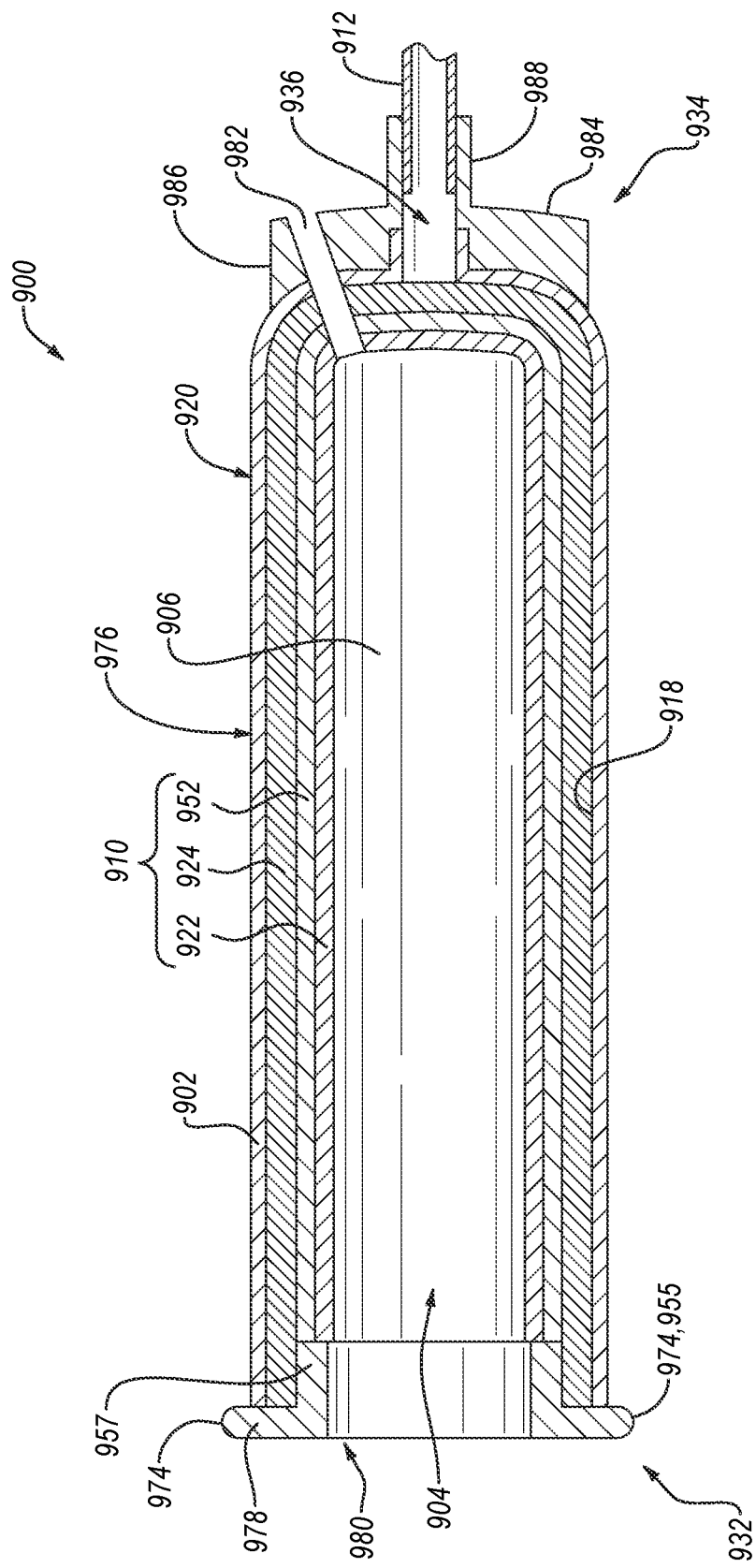
FIG. 9B is a cross-sectional view of the fluid collection assembly of FIG. 9A taken along the plane B-B of FIG. 9A, according to an embodiment.

FIG. 9A is an isometric view of a fluid collection assembly 900 according to an embodiment. FIG. 9B is a cross-sectional view of the fluid collection assembly 900 of FIG. 9A taken along the plane B-B of FIG. 9A, according to an embodiment. Referring to FIG. 9A and FIG. 9B, the fluid collection assembly 900 includes a receptacle 974 and a sheath 976. The receptacle 974 is sized, shaped, and made of a material to be coupled to skin that surrounds the male urethra and have the male urethra positioned therethrough. For example, the receptacle 974 may include an annular base 978 that defines an opening 980 in the receptacle 974. The annular base 978 is sized and shaped to be positioned around the male urethra (e.g., positioned around and/or over the penis) and the opening 980 may be configured to have the male urethra positioned therethrough. The annular base 978 may also be sized, shaped, made of a material, or otherwise configured to be coupled (e.g., adhesively attached, such as with a hydrogel adhesive) to the skin around the male urethral opening (e.g., around the penis). In an example, the annular base 978 may exhibit the general shape or contours of the skin surface that the annular base 978 is selected to be coupled with. The annular base 978 may be flexible thereby allowing the annular base 978 to conform to any shape of the skin surface. The annular base 978 may include a laterally extending flange 955. The receptacle 974 also defines a hollowed region that is configured to receive (e.g., seal against) the sheath 976. For example, the receptacle 974 may include a longitudinally extending flange 957 that extends upwardly from the annular base 978. The longitudinally extending flange 957 may be tall enough to prevent the sheath 976 from being accidentally removed from the receptacle 974 (e.g., at least 0.25 cm tall, 1 cm tall, at least 9 cm tall, or at least 5 cm tall). The receptacle 974 is located at a proximal region 932 (with respect to a wearer) of the fluid collection assembly 900.

The sheath 976 includes (e.g., may be formed from) a fluid impermeable barrier 902 that is sized and shaped to fit into the hollowed region of the receptacle 974. For example, the sheath 976 may be generally tubular or cup-shaped, as shown. The generally tubular or cup-shaped fluid impermeable barrier 902 may at least partially define the outer surface 920 of the sheath 976. The fluid impermeable barrier 902 may be similar or identical to any of the fluid impermeable barriers disclosed herein, in one or more aspects. For example, the fluid impermeable barrier 902 may be constructed of any of the materials disclosed herein for the fluid impermeable barrier 102. The fluid impermeable barrier 902 at least partially defines the chamber 906. For example, the inner surface 918 of the fluid impermeable barrier 902 at least partially defines the perimeter of the chamber 906. The chamber 906 may be similar or identical to any of the chambers disclosed herein in one or more aspects. For example, the chamber 906 may at least temporarily retain bodily fluids therein. As shown, the fluid collection assembly 900 may include at least one porous material 910 therein. The porous material 910 may be similar or identical to any of the porous materials disclosed herein in one or more aspects. For example, the porous material 910 may include one or more of a fluid permeable membrane 922, a fluid permeable support 924, an absorbent layer (not shown), or a leak prevention layer (not shown). The fluid impermeable barrier 902 may also define an opening 904 extending through the fluid impermeable barrier 902 that is configured to have a male urethral opening (e.g., penis) positioned therethrough.

The sheath 976 and fluid impermeable barrier 902 may also include at least one vacuum relief hole 982 that allows the chamber 906 to remain substantially at atmospheric pressure. The vacuum relief hole 982 may be located at any point on the sheath 976, such as near or nearer the opening 980. In some examples (not shown), the vacuum relief hole 982 may extend through the cap 984 or be disposed beneath the cap 984. In some examples, the fluid collection assembly 900 may not include the vacuum relief hole 982, such as when a more complete seal as desired for the chamber 906.

The sheath 976 also includes at least a portion of the conduit 912 therein, such as at least partially disposed in the chamber 906 of the conduit 912 only disposed in the fluid outlet 908. For example, the conduit 912 may extend from the sheath 976 at the distal region 934 to a proximal region 932 at least proximate to the opening 980. The proximal region 932 may be disposed near or on the skin around the male urethral opening (e.g., on the penis or pubic area therearound). Accordingly, when a patient lays on their back, bodily fluids (e.g., urine) may aggregate near the opening 980 against the skin of the subject. The bodily fluids may be removed from the chamber 906 via the conduit 912.

In some examples, the fluid impermeable barrier 902 may be constructed of a material and/or have a thickness that allows the sheath 976 to collapse when placed under vacuum, such as to remove air around a penis in the fluid collection assembly 900 during use. In such examples, the conduit 912 may extend only to or into the distal region 934 in the chamber 906 (e.g., not through to the area adjacent the opening).

In an example, portions of the chamber 906 may be substantially empty due to the varying sizes and rigidity of the male penis. However, in some examples, the outermost regions of the chamber 906 (e.g., periphery of the interior regions of the sheath 976) may include porous material 910 (e.g., one or more of the fluid permeable membrane 922 and fluid permeable support 924). For example, the porous material 910 may be bonded to the inner surface 918 of the fluid impermeable barrier 902. The porous material 910 may be positioned (e.g., at the distal end of the chamber 906) to blunt a stream of urine from the male urethral opening thereby limiting splashing and/or to direct the bodily fluids to a selected region of the chamber 906. Since the chamber 906 is substantially empty (e.g., substantially all of the chamber 906 forms a reservoir), the bodily fluids are likely to pool at a gravimetrically low point of the chamber 906. The gravimetrically low point of the chamber 906 may be at an intersection of the skin of an individual and the fluid collection assembly 900, a corner formed in the sheath 976, or another suitable location depending on the orientation of the wearer.

The porous material 910 may include one or more of the fluid permeable membrane 922 or the fluid permeable support 924. The fluid permeable membrane 922 and the fluid permeable support 924 may be similar or identical to any of the fluid permeable membranes or fluid permeable supports as respectively disclosed herein, in one or more aspects such as material make-up or wicking ability. One or more of the fluid permeable membrane 922 or the fluid permeable support 924 may be disposed between the fluid impermeable barrier 902 and a penis inserted into the chamber 906. The fluid permeable membrane 922 may be positioned between the fluid impermeable barrier 902 and a penis inserted into the chamber 906, such as between the fluid permeable support 924 and penis of a wearer as shown. The fluid permeable support 924 may be positioned between the fluid permeable membrane 922 and the fluid impermeable barrier 902. The inner surface 918, optionally including the end of the chamber 906 substantially opposite the opening 904, may be covered with one or both the fluid permeable membrane 922 or the fluid permeable support 924. The fluid permeable support 924 or the fluid permeable membrane 922 may be affixed (e.g., adhered) to the fluid impermeable barrier 902. The fluid permeable support 924 or the fluid permeable membrane 922 may be affixed to each other. In some examples, the porous material 910 only includes the fluid permeable membrane 922 or the fluid permeable support 924.

In some examples, the fluid collection assembly 900 includes a cap 984 at a distal region 934. The cap 984 defines an interior channel through which the bodily fluids may be removed from the fluid collection assembly 900. The interior channel is in fluid communication with the chamber 906. The cap 984 may be disposed over at least a portion of the distal region 934 of one or more of the fluid impermeable barrier 902 or the porous material 910. The cap 984 may be made of a polymer, rubber, or any other fluid impermeable material. The cap 984 may be attached to one or more of the fluid impermeable barrier 902, the porous material 910, or the conduit 912. The cap 984 may have a laterally extending flange 986 and a longitudinally extending flange 988. The laterally extending flange 986 may cover at least a portion of the distal region 934 of the fluid collection assembly 900. The longitudinally extending flange 988 may laterally extend a distance from the sheath 976. The longitudinally extending flange 972 is sized and configured to receive and fluidly seal against the conduit 912, such as within the interior channel. The conduit 912 may extend a distance within or through the cap 984, such as to the porous material 910, through the porous material 910, or to a point set-off from the porous material 910. In the latter example, as depicted in FIG. 9B, the interior channel of the cap 984 may define a reservoir 936 therein.

The reservoir 936 is an unoccupied portion of device such as in the cap 984 and is void of other material. In some examples, the reservoir 936 is defined at least partially by the porous material 910 and the cap 984. During use, the bodily fluids that are in the chamber 906 may flow through the porous material 910 to the reservoir 936. The reservoir 936 may store at least some of the bodily fluids therein and/or position the bodily fluids for removal by the conduit 912. In some examples, at least a portion of the porous material 910 may extend continuously between at least a portion of the opening of the interior channel and chamber 906 to move any bodily fluid from the opening directly to the reservoir 936.

In some examples (not shown), the fluid impermeable barrier 902 may be disposed on or over the cap 984, such as enclosing the cap 984 within the chamber 906.

In some examples, the sheath 976 may include at least a portion of the conduit 912 therein, such as at least partially disposed in the chamber 906. For example, the conduit 912 may extend from the sheath 976 to a region at least proximate to the opening 980. The inlet of the conduit 912 may be positioned adjacent to the annular base 978. The inlet of the conduit 912 may be positioned to be adjacent or proximate to the gravimetrically low point of the chamber 906, such as adjacent to the annular base 978. For example, the inlet may be co-extensive with or offset from the opening 980. In examples, the inlet may be positioned adjacent to the distal region 944 of the sheath 976.

The proximal region 932 may be disposed near or on the skin around the male urethral opening (e.g., around the penis) and the inlet of the conduit 912 may be positioned in the proximal region 932. The outlet of the conduit 912 may be directly or indirectly coupled to a vacuum source. Accordingly, the bodily fluids may be removed from the proximal region 932 of the chamber 906 via the conduit 912.

The receptacle 974, the sheath 976, the cap 984, and the conduit 912 may be attached together using any suitable method. For example, at least two of the receptacle 974, the sheath 976, the cap 984, or the conduit 912 may be attached together using at least one of an interference fit, an adhesive, stitching, welding (e.g., ultrasonic welding), tape, any other suitable method, or combinations thereof.

In some examples (not shown), the fluid collection assembly 900 may have a one piece design, with one or more of the sheath 976, the receptacle 974, and the cap 984 being a single, integrally formed piece.

Also as shown, the conduit 912 may be at least partially disposed with the chamber 906 of a fluid collection assembly 900. The conduit 912 may extend from the distal region 944 to the proximal region 932. For example, the conduit 912 may extend through the cap 984 to a point adjacent to the receptacle 974. The conduit 912 is sized and positioned to be coupled to a fluid storage container or the vacuum source (FIG. 10. An outlet of the conduit 912 may be operably coupled to the vacuum source, directly or indirectly. The inlet 914 (e.g., open terminal end) of the conduit 912 may be positioned within or adjacent to the chamber 906 such as at a location expected to be at the gravimetrically low point of the fluid collection assembly 900 during use. By positioning the inlet 914 in a location expected to be at the gravimetrically low point of the fluid collection assembly 900 when worn by the user, the bodily fluids introduced into the chamber 906 may be removed via the conduit 912 to prevent pooling or stagnation of the fluid within the chamber 906.

The fluid collection assembly 900 may include any of the leak prevention features disclosed herein. In an example, as shown, the one or more leak prevent features of the fluid collection assembly 900 may include the porous material 910 having least one additional layer 1052. The additional layer 1052 may be an absorbent layer similar to the absorbent layer 230 of FIG. 2B or a leak prevention layer similar to the leak prevention layer 552 of FIGS. 5A-5C. In an example, the one or more leak prevent features of the fluid collection assembly 900 may include the chamber 906 completely filled with porous material 910 (except for the portion configured to receive the male penis) such that the chamber 906 does not include a fluid reservoir. In an example, the one or more leak prevent features of the fluid collection assembly 900 may include the conduit 912 at least partially occupied with an additional porous material and, optionally, the additional porous material may extend from the conduit 912 into the fluid reservoir 936. In an example, the one or more leak prevent features of the fluid collection assembly 900 may include the conduit 912 exhibiting a "crinkle" structure or the fluid collection assembly 900 including at least one shape memory material.

Further examples of fluid collection assemblies that are configured to collect bodily fluids from males are disclosed in U.S. patent application Ser. No. 16/433,773 filed on Jun. 6, 2019, the disclosure of which is incorporated herein, in its entirety, by this reference.

In some examples, the vacuum source may be remotely located from the fluid collection assembly 900. In such examples, the conduit 912 may be fluidly connected to the fluid storage container, which may be disposed between the vacuum source and the fluid collection assembly 900.

During operation, a male using the fluid collection assembly 900 may discharge bodily fluids into the chamber 906. The bodily fluids may pool or otherwise be collected in the chamber 906. At least some of the bodily fluids may be pulled through the interior of the conduit 912 via the inlet. The bodily fluids may be drawn out of the fluid collection assembly 900 via the vacuum/suction provided by the vacuum source. During operation, the aperture 962 may substantially maintain the pressure in the chamber 906 at atmospheric pressure even though the bodily fluids are introduced into and subsequently removed from the chamber 906.

Figure 10:
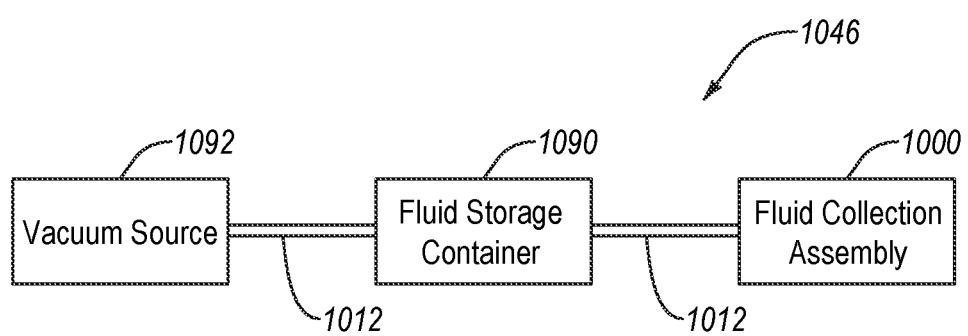
FIG. 10 is a block diagram of a system for fluid collection, according to an embodiment.

FIG. 10 is a block diagram of a system 1046 for fluid collection, according to an embodiment. The system 1046 includes a fluid collection assembly 1000, a fluid storage container 1090, and a vacuum source 1092. The fluid collection assembly 1000, the fluid storage container 1090, and the vacuum source 1092 may be fluidly coupled to each other via one or more conduits 112. For example, fluid collection assembly 1000 may be operably coupled to one or more of the fluid storage container 1090 or the vacuum source 1092 via the conduit 1012. The bodily fluids collected in the fluid collection assembly 1000 may be removed from the fluid collection assembly 1000 via the conduit 1012 which protrudes into the fluid collection assembly 1000. For example, an inlet of the conduit 1012 may extend into the fluid collection assembly 1000, such as to a reservoir therein. The outlet of the conduit 1012 may extend into the fluid collection assembly 1000 or the vacuum source 1092. Suction force may be introduced into the chamber of the fluid collection assembly 1000 via the inlet of the conduit 1012 responsive to suction (e.g., vacuum) force applied at the outlet of the conduit 1012.

The suction force may be applied to the outlet of the conduit 1012 by the vacuum source 1092 either directly or indirectly. The suction force may be applied indirectly via the fluid storage container 1090. For example, the outlet of the conduit 1012 may be disposed within the fluid storage container 1090 and an additional conduit 1012 may extend from the fluid storage container 1090 to the vacuum source 1092. Accordingly, the vacuum source 1092 may apply suction to the fluid collection assembly 1000 via the fluid storage container 1090. The suction force may be applied directly via the vacuum source 1092. For example, the outlet of the conduit 1012 may be disposed within the vacuum source 1092. An additional conduit 1012 may extend from the vacuum source 1092 to a point outside of the fluid collection assembly 1000, such as to the fluid storage container 1090. In such examples, the vacuum source 1092 may be disposed between the fluid collection assembly 1000 and the fluid storage container 1090.

The fluid collection assemblies 1000 may be similar or identical to any of the fluid collection assemblies disclosed herein in one or more aspects. The fluid collection assembly 1000 may be shaped and sized to be positioned adjacent to a female urethral opening or have a male urethral opening positioned therethrough (e.g., receive a penis therein). For example, the fluid collection assembly 1000 may include a fluid impermeable barrier at least partially defining a chamber (e.g., interior region) of the fluid collection assembly 1000. The fluid impermeable barrier also defines an opening extending therethrough from the external environment. The opening may be positioned adjacent to a female urethral opening or have a male urethral opening positioned therethrough. The fluid collection assembly 1000 may include a fluid permeable membrane disposed within the fluid impermeable barrier. The fluid collection assembly 1000 may include at least one porous material disposed in the chamber such as one or more of a fluid permeable support and a fluid permeable membrane. The fluid collection assembly 1000 includes the shape memory material on or incorporated in one or more components thereof. The shape memory material is sized, shaped, and positioned to retain a selected geometric configuration as disclosed herein. The conduit 1012 may extend into the fluid collection assembly 1000 at a first end (e.g., proximal) region, through one or more of the fluid impermeable barrier, fluid permeable membrane, or the fluid permeable support to a second end (e.g., distal) region of the fluid collection assembly 1000. The conduit 1012 includes an inlet and an outlet, the outlet being fluidly coupled to the fluid storage container and the inlet being positioned in a portion of the chamber selected to be at a gravimetrically low point of the fluid collection assembly 1000 when worn.

The fluid storage container 1090 is sized and shaped to retain the bodily fluids therein. The fluid storage container 1090 may include a bag (e.g., drainage bag), a bottle or cup (e.g., collection jar), or any other enclosed container for storing bodily fluids such as urine. In some examples, the conduit 1012 may extend from the fluid collection assembly 1000 and attach to the fluid storage container 1090 at a first point therein. An additional conduit 1012 may attach to the fluid storage container 1090 at a second point thereon and may extend and attach to the vacuum source 1092. Accordingly, a vacuum (e.g., suction) may be drawn through fluid collection assembly 1000 via the fluid storage container 1090. The bodily fluids, such as urine, may be drained from the fluid collection assembly 1000 using the vacuum source 1092.

The vacuum source 1092 may include one or more of a manual vacuum pump, and electric vacuum pump, a diaphragm pump, a centrifugal pump, a displacement pump, a magnetically driven pump, a peristaltic pump, or any pump configured to produce a vacuum. The vacuum source 1092 may provide a vacuum or suction to remove the bodily fluids from the fluid collection assembly 1000. In some examples, the vacuum source 1092 may be powered by one or more of a power cord (e.g., connected to a power socket), one or more batteries, or even manual power (e.g., a hand operated vacuum pump). In some examples, the vacuum source 1092 may be sized and shaped to fit outside of, on, or within the fluid collection assembly 1000. For example, the vacuum source 1092 may include one or more miniaturized pumps or one or more micro pumps. The vacuum sources 1092 disclosed herein may include one or more of a switch, a button, a plug, a remote, or any other device suitable to activate the vacuum source 1092.

While various aspects and embodiments have been disclosed herein, other aspects and embodiments are contemplated. The various aspects and embodiments disclosed herein are for purposes of illustration and are not intended to be limiting.

Terms of degree (e.g., "about," "substantially," "generally," etc.) indicate structurally or functionally insignificant variations. In an example, when the term of degree is included with a term indicating quantity, the term of degree is interpreted to mean ±10%, ±5%, ±2% or 0% of the term indicating quantity. In an example, when the term of degree is used to modify a shape, the term of degree indicates that the shape being modified by the term of degree has the appearance of the disclosed shape. For instance, the term of degree may be used to indicate that the shape may have rounded corners instead of sharp corners, curved edges instead of straight edges, one or more protrusions extending therefrom, is oblong, is the same as the disclosed shape, etc.

We claim:

1. A fluid collection assembly for capturing one or more bodily fluids from an individual, comprising:
    a fluid impermeable barrier defining:
        at least one opening;
        a chamber in fluid communication with the at least one opening; and
        at least one fluid outlet;
    at least one porous material disposed in the chamber; and
    at least one conduit attached to the at least one fluid outlet, the at least one conduit including one or more walls, the one or more walls of the conduit defining and extending between an open terminal end and an outlet portion, the open terminal end disposed in the chamber and the outlet portion disposed in the at least one fluid outlet, the one or more walls defining one or more conduit inlets, the one or more conduit inlets located between the open terminal end and the outlet portion, at least a region of the one or more walls defining the open terminal end and the one or more conduit inlets exhibits single piece construction, wherein the open terminal end of the conduit has an opening that is larger than the one or more conduit inlets.

2. The fluid collection assembly of claim 1, wherein the fluid impermeable barrier exhibits a concavely curved cross-sectional shape.

3. The fluid collection assembly of claim 1, wherein the chamber being substantially completely filled with the at least one porous material.

4. The fluid collection assembly of claim 1, further including at least one additional porous material disposed in the at least one conduit.

5. The fluid collection assembly of claim 4, wherein:
the chamber includes a substantially unoccupied fluid reservoir;
the at least one conduit extends from the at least one fluid outlet to or near the fluid reservoir; and
the at least one additional porous material is disposed in the at least one conduit and extends from the at least one conduit into the fluid reservoir.

6. The fluid collection assembly of claim 1, wherein the at least one porous material includes a fluid permeable membrane, a fluid permeable support, and at least one absorbent material disposed between the fluid permeable membrane and the fluid permeable support.

7. The fluid collection assembly of claim 1, wherein at least one of the one or more conduit inlets includes a one-way valve that is configured to allow the bodily fluids to enter an interior of the at least one conduit and substantially prevent the bodily fluids to exiting the interior of the at least one conduit.

8. The fluid collection assembly of claim 1, wherein the at least one conduit exhibits a length measured from the open terminal end to the outlet portion, and wherein the one or more conduit inlets are spaced from the open terminal end by about 25% to about 40% of the length of the at least one conduit.

9. The fluid collection assembly of claim 1, further comprising at least one additional conduit disposed in the chamber, a length of the at least one additional conduit is different from the length of the at least one conduit.

10. The fluid collection assembly of claim 1, further comprising a leak prevention material disposed in the at least one porous material, wherein:
the leak prevention material includes at least one first layer and at least one second layer positioned downstream from the at least one first layer, each of the at least one first layer and the at least one second layer defining a plurality of void spaces;
wherein at least one of:
the at least one first layer exhibits a first number density of the plurality of void spaces and the at least one second layer exhibits a second number density of the plurality of void spaces that is greater than the first number density; and/or
each of the plurality of void spaces of the at least one first layer exhibits a first average cross-sectional area and each of the plurality of void spaces of the at least one second layer exhibits a second average cross-sectional area that is greater than the first average cross-sectional area of each of the void space.

11. The fluid collection assembly of claim 1, wherein the at least one conduit includes one or more peaks and one or more valleys.

12. The fluid collection assembly of claim 1, wherein the at least one conduit exhibits an outer diameter that is about 5 mm to about 9 mm.

13. The fluid collection assembly of claim 1, further including the at least one porous material having at least one non-bodily fluid disposed therein.

14. The fluid collection assembly of claim 1, wherein a size of the at least one fluid outlet is smaller than a size of the open terminal end.

15. A fluid collection assembly for capturing one or more bodily fluids from an individual, the fluid collection assembly comprising:
a fluid impermeable barrier defining:
at least one opening;
a chamber in fluid communication with the at least one opening; and
at least one fluid outlet;
at least one porous material disposed in the chamber, the at least one porous material including at least one first layer and at least one second layer positioned downstream from the at least one first layer, each of the at least one first layer and the at least one second layer defining a plurality of void spaces, each of the plurality of void spaces of the at least one first layer exhibits a first average cross-sectional area and each of the plurality of void spaces of the at least one second layer exhibits a second average cross-sectional area that is greater than the first average cross-sectional area of each of the void space;
at least one first conduit attached to the at least one fluid outlet, the at least one first conduit including one or more walls, the one or more walls of the conduit defining and extending between an open terminal end and an outlet portion, the open terminal end disposed in the chamber and the outlet portion disposed in the at least one fluid outlet, one or more walls defining one or more conduit inlets, the one or more conduit inlets located between the open terminal end and the outlet portion, at least a region of the one or more walls defining the open terminal end and the one or more conduit inlets exhibits single piece construction, wherein the open terminal end of the conduit has an opening that is larger than the one or more conduit inlets; and
at least one second conduit disposed in the chamber, a length of the at least one second conduit is different the length of the at least one first conduit.

16. A fluid collection assembly for capturing one or more bodily fluids from an individual, the fluid collection comprising:
a fluid impermeable barrier defining:
at least one opening;
a chamber in fluid communication with the at least one opening; and
at least one fluid outlet;
at least one porous material disposed in the chamber, the at least one porous material including at least one first layer and at least one second layer positioned downstream from the at least one first layer, each of the at least one first layer and the at least one second layer defining a plurality of void spaces, each of the plurality of void spaces of the at least one first layer exhibits a first average cross-sectional area and each of the plurality of void spaces of the at least one second layer exhibits a second average cross-sectional area that is greater than the first average cross-sectional area of each of the void space;
at least one first conduit attached to the at least one fluid outlet, the at least one first conduit including one or more walls exhibiting single piece construction, the one or more walls of the conduit defining and extending between an open terminal end and an outlet portion, the open terminal end disposed in the chamber and the outlet portion disposed in the at least one fluid outlet, one or more wall defining one or more conduit inlets, the one or more conduit inlets located between the open terminal end and the outlet portion, a size of the at least one fluid outlet is smaller than a size of the open terminal end, the at least one first conduit exhibiting an outer diameter that is about 5 mm to about 9 mm, at least a region of the one or more walls defining the open terminal end and the one or more conduit inlets exhibits single piece construction, wherein the open terminal end of the conduit has an opening that is larger than the one or more conduit inlets; and at least one second conduit disposed in the chamber, a length of the at least one second conduit is different the length of the at least one first conduit, the at least one second conduit includes one or more peaks and one or more valleys.

17. The fluid collection assembly of claim 1, wherein the fluid impermeable barrier exhibits a generally flat disk-like shape.

18. The fluid collection assembly of claim 1, wherein the fluid impermeable barrier exhibits a generally flat elongated shape.

19. The fluid collection assembly of claim 1, wherein the at least one conduit exhibits a length measured from the open terminal end to the outlet portion, and wherein the one or more conduit inlets are spaced from the open terminal end by about 40% to about 60% of the length of the at least one conduit.

20. The fluid collection assembly of claim 1, wherein the at least one conduit exhibits a length measured from the open terminal end to the outlet portion, and wherein the one or more conduit inlets are spaced from the open terminal end by about 60% to about 99% of the length of the at least one conduit.

* * * * *